United States Patent
Jeon et al.

(10) Patent No.: US 11,370,758 B2
(45) Date of Patent: Jun. 28, 2022

(54) IDO-TDO DUAL INHIBITOR AND RELATED METHODS OF USE

(71) Applicants: CMG PHARMACEUTICAL CO., LTD., Seoul (KR); SUNGKWANG MEDICAL FOUNDATION, Seoul (KR)

(72) Inventors: Hong Jae Jeon, Seongnam-si (KR); Chan Kim, Yongin-si (KR); Na Keum Lee, Seongnam-si (KR); Jin Sung Kim, Seongnam-si (KR); Hye Sun Jeon, Yongin-si (KR); Young Eun Kwon, Yongin-si (KR); Ju Hui Jeong, Seongnam-si (KR)

(73) Assignees: CMG PHARMACEUTICAL CO., LTD., Seoul (KR); SUNGKWANG MEDICAL FOUNDATION, Seoul (KR)

( * ) Notice: Subject to any disclaimer, the term of this patent is extended or adjusted under 35 U.S.C. 154(b) by 17 days.

(21) Appl. No.: 16/361,908

(22) Filed: Mar. 22, 2019

(65) Prior Publication Data

US 2019/0292150 A1     Sep. 26, 2019

Related U.S. Application Data

(60) Provisional application No. 62/647,483, filed on Mar. 23, 2018.

(51) Int. Cl.
| | |
|---|---|
| *C07D 413/12* | (2006.01) |
| *C07D 209/42* | (2006.01) |
| *A61P 35/00* | (2006.01) |
| *C07D 487/04* | (2006.01) |
| *C07D 471/04* | (2006.01) |

(52) U.S. Cl.
CPC ............ *C07D 209/42* (2013.01); *A61P 35/00* (2018.01); *C07D 413/12* (2013.01); *C07D 471/04* (2013.01); *C07D 487/04* (2013.01)

(58) Field of Classification Search
CPC .. C07D 413/12; C07D 471/04; C07D 487/04; A61P 35/00
See application file for complete search history.

(56) References Cited

U.S. PATENT DOCUMENTS

2015/0329540 A1* 11/2015 Yamashita ........... C07D 471/04
                                                                544/362

OTHER PUBLICATIONS

Acute Leukemia, Merck Manual (Online Edition) 6 pages, pp. 1-6 (2013).*
Damasio, Alzheimer's Disease and related dementias, Cecil Textbook of Medicine, 20th Edition, vol. 2, pp. 1992-1996, 1996.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Layzer, Degenerative diseases of the nervous system, Cecil Textbook of Medicine, 20th Edition, vol. 2, pp. 2050-2057, 1996.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-1010, 1996.*

* cited by examiner

*Primary Examiner* — Deepak R Rao
(74) *Attorney, Agent, or Firm* — Leydig, Voit & Mayer, Ltd.

(57) ABSTRACT

Provided is an inhibitor of an indoleamine 2,3-dioxygenase (IDO) and/or tryptophan 2,3-dioxygenase (TDO) of formula (I) or a pharmaceutically acceptable salt thereof:

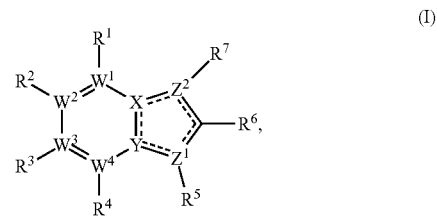

(I)

in which $W^1$, $W^2$, $W^3$, and $W^4$, X, Y, $Z^1$, $Z^2$, and $R^{1-7}$ are described herein. Further provided is a method of treating or preventing a IDO and/or TDO-mediated disease using an effective amount of the compound of formula (I) or a pharmaceutically acceptable salt thereof.

19 Claims, 5 Drawing Sheets

IDO-TDO DUAL INHIBITOR AND RELATED METHODS OF USE

CROSS-REFERENCE TO A RELATED APPLICATION

This patent application claims the benefit of U.S. Provisional Patent Application No. 62/647,483, filed Mar. 23, 2018, which is incorporated by reference.

BACKGROUND OF THE INVENTION

As researchers continue to explore immune checkpoints as targets for anticancer and other treatment therapies, the indoleamine 2,3-dioxygenase (IDO) pathway has emerged as a contender to yield the next batch of new drugs in the field. The IDO protein, or indoleamine 2,3-dioxygenase, has been identified as a checkpoint protein involved in generating the immunosuppressive tumor microenvironment that supports tumor growth. The enzyme has two isoforms, IDO1 and IDO2, which act as the first step in the metabolic pathway that breaks down the essential amino acid tryptophan. Tryptophan 2,3-dioxygenase (TDO) is a biologically significant enzyme that catalyzes the first and committing step of L-Trp degradation in the kynurenine pathway. The kynurenine pathway constitutes the major route of de novo biosynthesis of nicotinamide adenine dinucleotide (NAD), which is one of the essential redox cofactors in all living systems. Excessive accumulation of many of the intermediate metabolites of this pathway can lead to numerous physiological and pathological conditions, including cataract formation, cerebral malaria, Alzheimer's disease, HIV infection, Huntington's disease, depression, and ischemic brain injury. Both IDO and TDO triggered by the immune challenge can catalzye L-tryptophan to kynurenine and then start the kynurenine pathway.

Thus, there remains a need to provide new inhibitors of IDO and/or TDO to treat IDO- and TDO-mediated disease, including chemo-resistant cancer and diseases of the brain.

BRIEF SUMMARY OF THE INVENTION

The invention provides a compound of formula (I) or a pharmaceutically acceptable salt thereof:

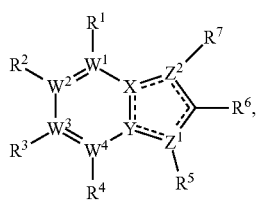

(I)

in which $W^1$, $W^2$, $W^3$, and $W^4$, X, Y, $Z^1$, $Z^2$, and $R^{1-7}$ are described herein. It is envisioned that a compound of formula (I) is desirable for treating diseases associated with the enzymes IDO and/or TDO, such as cancer, due at least in part, because of the compound's ability to inhibit one or preferably both of these enzymes Thus, the invention further provides a method of treating an IDO- and/or TDO-mediated disease in a subject, such as cancer, a neurological and/or brain disorder, an eye disorder, or HIV infection. The method comprises administering to a subject in need of such treatment a pharmaceutically effective amount of a compound of formula (I) or a pharmaceutically acceptable salt thereof.

Also provided is a method of inhibiting an IDO and/or TDO enzyme in a cell comprising contacting an effective amount of a compound of formula (I) or a pharmaceutically acceptable salt thereof to a cell in need of such inhibition.

DETAILED DESCRIPTION OF THE INVENTION

Figure 1:
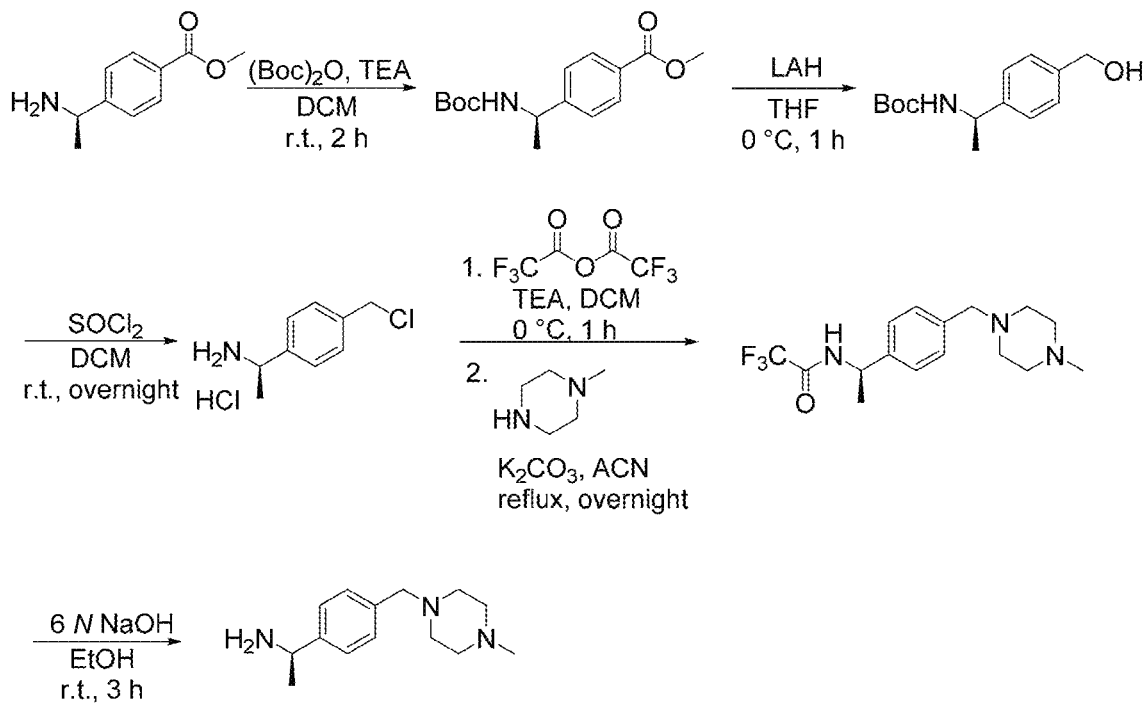
FIG. 1 is a chemical scheme depicting the synthesis of (R)-1-(4-((4-methylpiperazin-1-yl)methyl)phenyl)ethanamine (intermediate 1).

The present invention provides compound of formula (I):

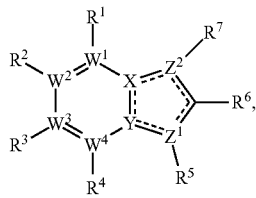
(I)

wherein
$W^1$, $W^2$, $W^3$, and $W^4$ are each independently CH or N;
$R^1$, $R^2$, $R^3$, and $R^4$ are each independently H, alkyl, haloalkyl, halogen, or CN;
X, Y, $Z^1$, and $Z^2$ are independently C or N;
$R^5$ and $R^7$ are independently absent, H, $C_1$-$C_6$ alkyl, or cycloalkyl;
$R^6$ is a group selected from one of the following:

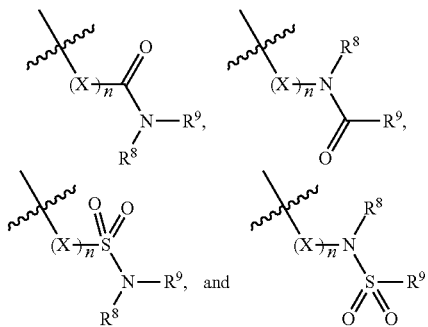

wherein
$R^8$ is selected from H and a substituted or unsubstituted organic group;
$R^9$ is selected from H and a substituted or unsubstituted organic group;
X is selected from $C(R^{10})_2$ and $NR^{11}$;
each $R^{10}$ is selected from a group consisting of H, alkyl, and cycloalkyl;
$R^{11}$ is selected from H and a substituted or unsubstituted organic group; and
n is 0 or 1 if X is $NR^{11}$; or n is 0, 1, or 2 if X is $C(R^{10})_2$, wherein each dashed line is a single bond or double bond as valences permit,
or a pharmaceutically acceptable salt thereof.

In some embodiments of the compound of formula (I) or a salt thereof, $R^9$ is a residue of the formula

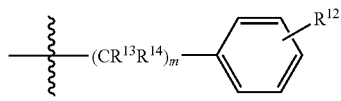

wherein
$R^{12}$ is selected from a group consisting of H, $(CH_2)_o NR^{15}R^{16}$, and $(CH_2)_o C(=O)NR^{15}R^{16}$,
$R^{13}$ and $R^{14}$ are the same or different and are each H or alkyl, $R^{15}$ and $R^{16}$ are the same or different and are each H, alkyl, or combine, along with the N to which they are bonded, to form an optionally substituted heterocyclic ring containing N and optionally one or more additional heteroatoms selected from nitrogen, oxygen, and sulfur,
m is 0 to 6, and
o is 0 to 4.

In certain compounds of formula (I) or a salt thereof, (i) $R^{13}$ and $R^{14}$ are each H, (ii) $R^{13}$ and $R^{14}$ are each alkyl (e.g., methyl), or (iii) $R^{13}$ is H and $R^{14}$ is alkyl (e.g., methyl).

In any of the foregoing embodiments, m is preferably 1 or 2 and/or o is preferably 0 or 1.

Preferably, $R^{15}$ and $R^{16}$ combine, along with the N to which they are bonded, to form a heterocyclic ring (e.g., morpholinyl, piperazinyl, piperidinyl, or pyrrolyl) that is optionally substituted with one or more substituents. The substituents include moieties, such as at least one alkyl, alkylcarbonyl (e.g., acetyl), and sulfonyl moiety (e.g., methylsulfonyl).

In any of the foregoing embodiments of compounds of formula (I) or a salt thereof, (i) one of $R^1$, $R^2$, $R^3$, and $R^4$ is alkyl, haloalkyl, halogen, or CN and the remaining three substituents are H, or (ii) each of $R^1$, $R^2$, $R^3$, and $R^4$ is H.

Preferably, (i) $W^1$, $W^2$, $W^3$, and $W^4$ are each CH, or (ii) one of $W^1$, $W^2$, $W^3$, and $W^4$ is N, and the remaining three substituents are each CH.

In certain embodiments of the compound of formula (I) or a salt thereof, X and $Z^1$ are nitrogen, and Y and $Z^2$ are carbon. In such instance, the compound of formula (I) can be a compound of formula (Ia)

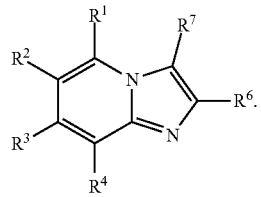
(Ia)

Exemplary compounds of formula (I), including compounds of formula (Ia), include

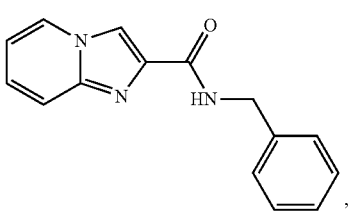
(CB516)

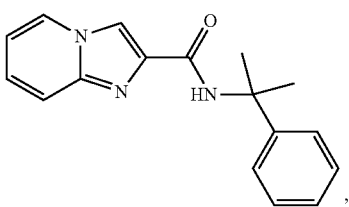
(CB517)

(CB518)
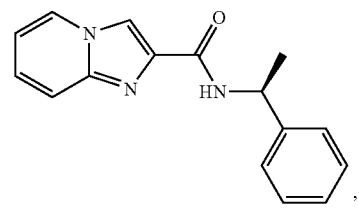
(CB512)
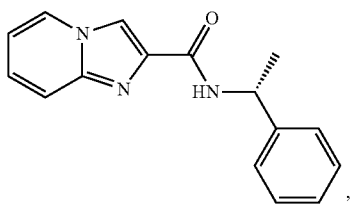
(CB539)
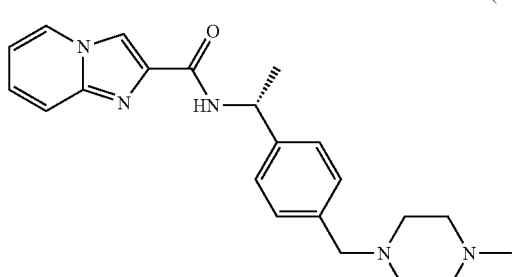
(CB540)
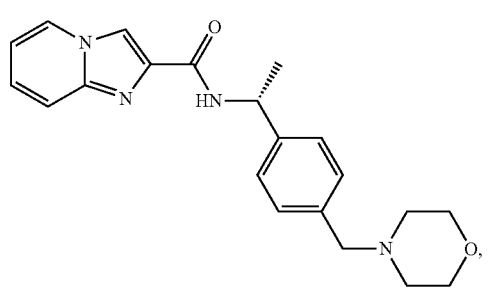
(CB533)
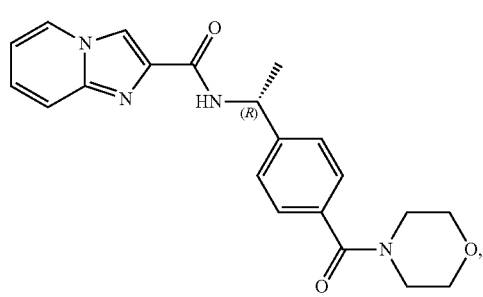
(CB532)
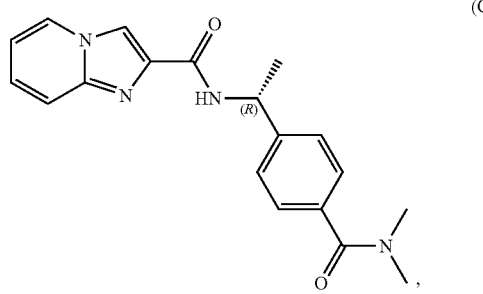
(CB534)
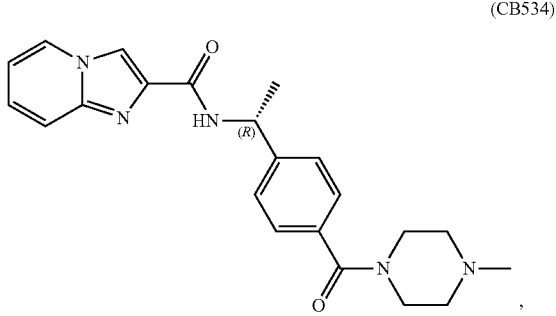
(CB548)
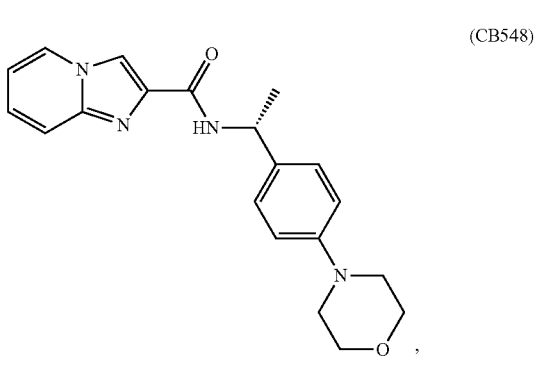
(CB549)
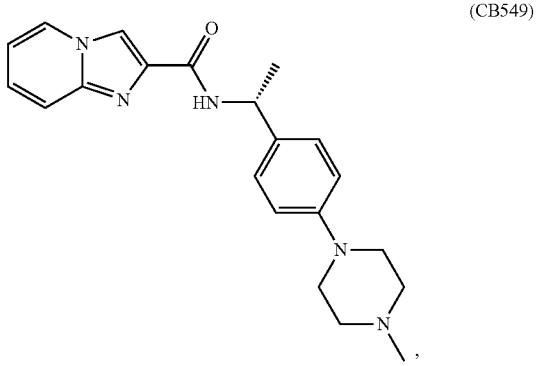
(CB550)
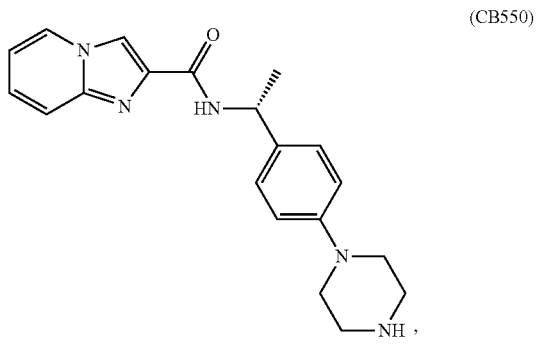
(CB556)
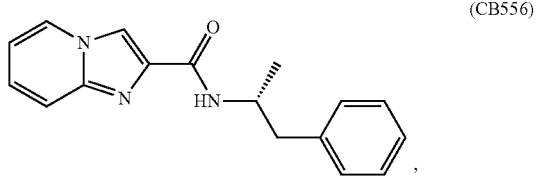

-continued (CB581)

(CB582)

(CB583)

(CB584)

(CB585)

(CB586)

(CB590)

(CB595)

-continued
(CB596)
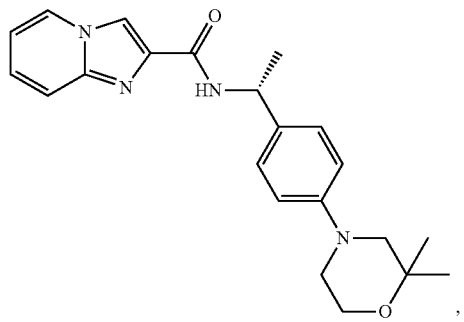
(CB597)
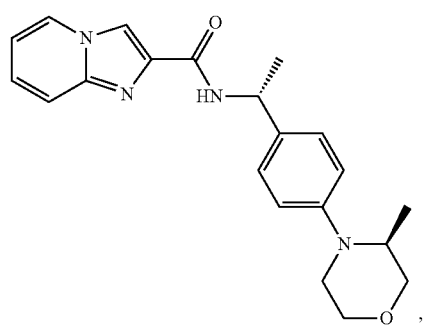
(CB598)
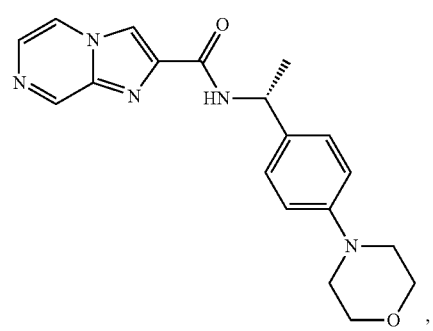
and
(CB599)
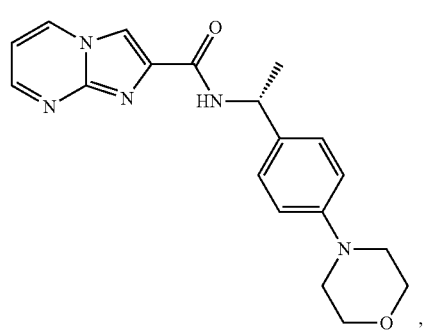
or a pharmaceutically acceptable salt thereof.
In other embodiments of the compound of formula (I) or salt thereof, X and $Z^2$ are carbon, and Y and $Z^1$ are nitrogen. Accordingly, such compounds of formula (I) can be a compound of formula (Ib)
(Ib)
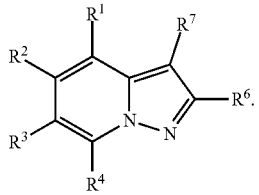
Exemplary compounds of formula (I), including compounds of formula (Ib), include:
(CB511)
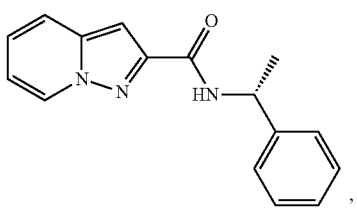
(CB570)
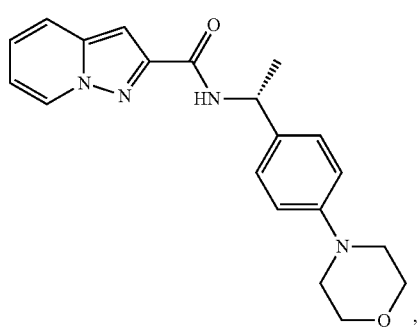
(CB571)
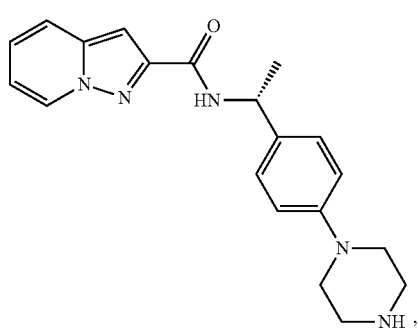
(CB569)
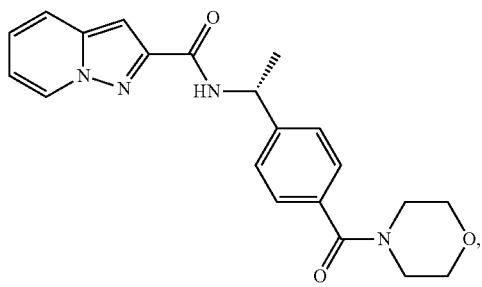

-continued

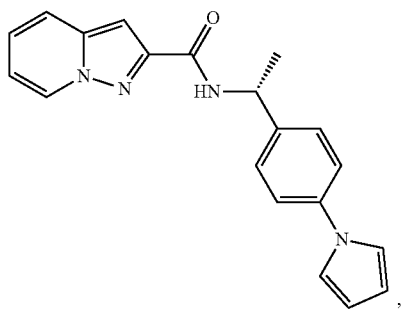
(CB629)

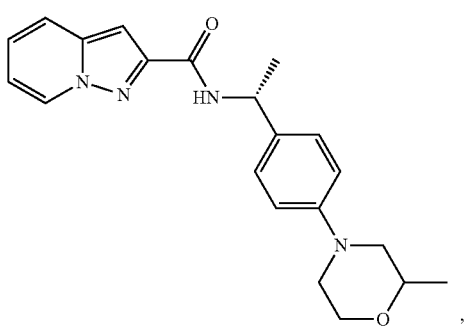
(CB630)

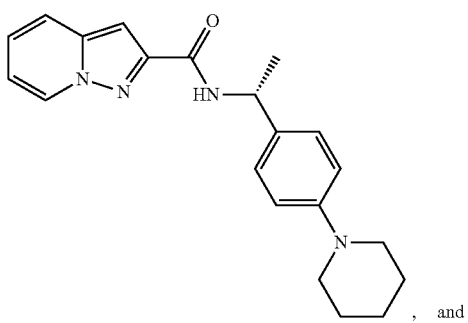
(CB633)
, and

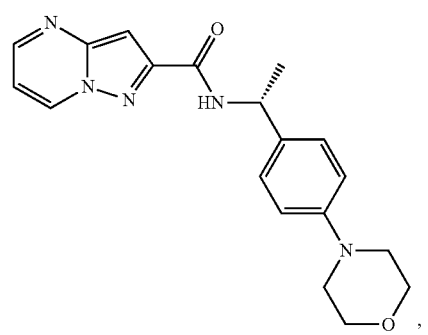
(CB600)

or a pharmaceutically acceptable salt thereof.

In other preferred embodiments of the compound of formula (I) or a salt thereof, X and Y are carbon, and $Z^1$ and $Z^2$ are nitrogen. In such instance, the compound of formula (I) can be a compound of formula (Ic)

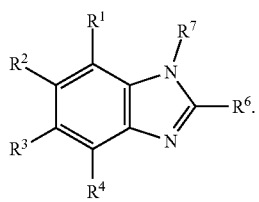
(Ic)

An exemplary compound of formula (Ic) is

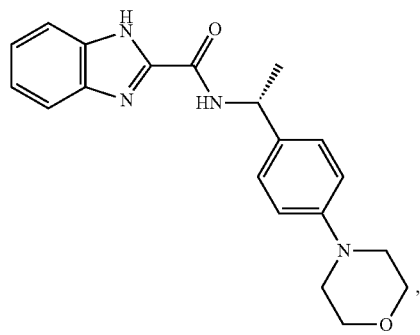
(CB631)

or a pharmaceutically acceptable salt thereof.

In some aspects, the compound of formula (I) is formula (Id)

(Id)

wherein
$R^1$, $R^2$, $R^3$, and $R^4$ are each independently H, F, Br, or Cl;
X and Y are independently C or N;
$R^5$ is absent or H;
$R^{12}$ is selected from a group consisting of H, $(CH_2)_o$ $NR^{15}R^{16}$, and $(CH_2)_oC(=O)NR^{15}R^{16}$,
$R^{13}$ and $R^{14}$ are the same or different and are each H or alkyl,
$R^{15}$ and $R^{16}$ are the same or different and are both alkyl (e.g., methyl), or combine, along with the N to which they are bonded, to form heterocyclic ring containing N and optionally one or more additional heteroatoms selected from nitrogen, oxygen, and sulfur that is optionally substituted with a $C_1$-$C_6$ alkyl,
m is 0 to 6, and
o is 0 or 1,
wherein each dashed line is a single bond or double bond as valences permit,
or a pharmaceutically acceptable salt thereof.

As used herein, the term "alkyl" means a straight or branched, saturated aliphatic radical having a chain containing from, for example, from about 1 to about 10 carbon atoms, e.g., from about 1 to about 8 carbon atoms. $C_x$ alkyl and $C_x$-$C_y$ alkyl are typically used where X and Y indicate the number of carbon atoms in the chain (e.g., $C_1$-$C_{10}$ alkyl, $C_1$-$C_8$ alkyl, $C_1$-$C_6$ alkyl, or $C_1$-$C_4$ alkyl). For example, $C_1$-$C_6$ alkyl includes alkyls that have a chain of between 1 and 6 carbons (e.g., methyl, ethyl, propyl, isopropyl, butyl, sec-butyl, isobutyl, tert-butyl, pentyl, neopentyl, hexyl, and the like). Alkyl represented along with another radical (e.g., as in arylalkyl) means a straight or branched, saturated alkyl divalent radical having the number of atoms indicated or when no atoms are indicated means a bond, e.g., ($C_6$-$C_{10}$) aryl($C_0$-$C_3$)alkyl includes phenyl, benzyl, phenethyl, 1-phenylethyl 3-phenylpropyl, and the like. The backbone of the alkyl can be optionally inserted with one or more heteroatoms, such as N, O, or S.

Unless the number of carbons is otherwise specified, "lower alkyl" as used herein means an alkyl group, as defined above, but having from 1 to 10 carbons, more preferably from 1 to 6 carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

As used herein, the term "alkenyl" refers to unsaturated straight-chain, branched-chain or cyclic hydrocarbon radicals having at least one carbon-carbon double bond and containing from, for example, about 2 to about 8 carbon atoms (branched alkenyls are about 3 to about 8 carbons atoms), e.g., from about 3 to about 6 carbon atoms (branched alkenyls are about 3 to about 6 carbons atoms). $C_x$ alkenyl and $C_x$-$C_y$alkenyl are typically used where X and Y indicate the number of carbon atoms in the chain (e.g., $C_2$-$C_{10}$ alkenyl, $C_2$-$C_8$ alkenyl, $C_2$-$C_6$ alkenyl, or $C_2$-$C_4$ alkenyl). For example, $C_2$-$C_6$ alkenyl includes alkenyls that have a chain of between 2 and 6 carbons and at least one double bond, e.g., vinyl, allyl, propenyl, isopropenyl, 1-butenyl, 2-butenyl, 3-butenyl, 2-methylallyl, 1-hexenyl, 2-hexenyl, 3-hexenyl, and the like). Alkenyl represented along with another radical (e.g., as in arylalkenyl) means a straight or branched, alkenyl divalent radical having the number of atoms indicated. The backbone of the alkenyl can be optionally inserted with one or more heteroatoms, such as N, O, or S.

As used herein, the term "alkynyl" refers to unsaturated hydrocarbon radicals having at least one carbon-carbon triple bond. $C_x$ alkynyl and $C_x$-$C_y$alkynyl are typically used where X and Y indicate the number of carbon atoms in the chain (e.g., $C_2$-$C_{10}$ alkynyl, $C_2$-$C_8$ alkynyl, $C_2$-$C_6$ alkynyl, or $C_2$-$C_4$ alkynyl). For example, $C_2$-$C_6$ alkynyl includes alkynls that have a chain of between 2 and 6 carbons and at least one triple bond, e.g., ethynyl, 1-propynyl, 2-propynyl, 1-butynyl, isopentynyl, 1,3-hexa-diyn-yl, n-hexynyl, 3-pentynyl, 1-hexen-3-ynyl and the like. Alkynyl represented along with another radical (e.g., as in arylalkynyl) means a straight or branched, alkynyl divalent radical having the number of atoms indicated. The backbone of the alkynyl can be optionally inserted with one or more heteroatoms, such as N, O, or S.

The terms "alkylene," "alkenylene," and "alkynylene" refer to divalent alkyl, alkelyne, and alkynylene" radicals. Prefixes $C_x$ and $C_x$-$C_y$ are typically used where X and Y indicate the number of carbon atoms in the chain (e.g., 1 to 10, 1 to 8, 1 to 6, 1 to 4, 1 to 3, or 1 to 2). For example, $C_1$-$C_6$ alkylene includes methylene, (—$CH_2$—), ethylene (—$CH_2CH_2$—), trimethylene (—$CH_2CH_2CH_2$—), tetramethylene (—$CH_2CH_2CH_2CH_2$—), 2-methyltetramethylene (—$CH_2CH(CH_3)CH_2CH_2$—), pentamethylene (—$CH_2CH_2CH_2CH_2CH_2$—), and the like).

As used herein, the term "alkylidene" means a straight or branched unsaturated, aliphatic, divalent radical having a general formula =$CR_aR_b$. Non-limiting examples of $R_a$ and $R_b$ are each independently hydrogen, alkyl, substituted alkyl, alkenyl, or substituted alkenyl. $C_x$ alkylidene and $C_x$-$C_y$ alkylidene are typically used where X and Y indicate the number of carbon atoms in the chain (e.g., 1 to 10, 1 to 8, 1 to 6, 1 to 4, 1 to 3, or 1 to 2). For example, $C_2$-$C_6$ alkylidene includes methylidene (=$CH_2$), ethylidene (=$CHCH_3$), isopropylidene (=$C(CH_3)_2$), propylidene (=$CHCH_2CH_3$), allylidene (=$CH$—$CH$=$CH_2$), and the like).

The term "heteroalkyl," as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "aryl" refers to monocyclic, bicyclic, or tricyclic fused aromatic ring system. It is understood that the term aryl includes carbocyclic moieties that are planar and comprise 4n+2 π electrons, according to Hickel's Rule, wherein n=1, 2, or 3. An aromatic ring can be such that the ring atoms are only carbon atoms (e.g., aryl) or can include carbon and non-carbon atoms (e.g., heteroaryl). $C_x$ aryl and $C_x$-$C_y$ aryl are typically used where X and Y indicate the number of carbon atoms in the ring system. For example, $C_6$-$C_{12}$ aryl includes aryls that have 6 to 12 carbon atoms in the ring system (e.g., from 6 to 30, 6 to 18, 6 to 14, or 6 to 10). The term "aryl" refers to an unsubstituted or substituted aromatic carbocyclic moiety, as commonly understood in the art, and includes monocyclic and polycyclic aromatics such as, for example, phenyl, biphenyl, naphthyl, anthracenyl, pyrenyl, and the like. However, the aryl can be optionally substituted with one or more heteroatoms, such as N, O, or S. Accordingly, exemplary aryl groups include, but are not limited to, pyridinyl, pyrimidinyl, furanyl, thienyl, imidazolyl, thiazolyl, pyrazolyl, pyridazinyl, pyrazinyl, triazinyl, tetrazolyl, indolyl, benzyl, phenyl, naphthyl, anthracenyl, azulenyl, fluorenyl, indanyl, indenyl, naphthyl, phenyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl, and the like. In some embodiments, 1, 2, 3, or 4 hydrogen atoms of each ring can be substituted by a substituent.

The term "heteroaryl" refers to an aromatic 5-8 membered monocyclic, 8-12 membered fused bicyclic, or 11-14 membered fused tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$ heteroaryl and $C_x$-$C_y$ heteroaryl are typically used where X and Y indicate the number of carbon atoms in the ring system. For example, $C_4$-$C_9$ heteroaryl includes heteroaryls that have 4 to 9 carbon atoms in the ring system. Heteroaryls include, but are not limited to, those derived from benzo[b] furan, benzo[b] thiophene, benzimidazole, imidazo[4,5-c] pyridine, quinazoline, thieno[2,3-c]pyridine, thieno[3,2-b] pyridine, thieno[2, 3-b]pyridine, indolizine, imidazo[1,2a] pyridine, quinoline, isoquinoline, phthalazine, quinoxaline, naphthyridine, quinolizine, indole, isoindole, indazole, indoline, benzoxazole, benzopyrazole, benzothiazole, imidazo[1, 5-a]pyridine, pyrazolo[1,5-a]pyridine, imidazo[1,2-a]pyrimidine, imidazo[1,2-c]pyrimidine, imidazo[1,5-a] pyrimidine, imidazo[1,5-c]pyrimidine, pyrrolo[2,3-b] pyridine, pyrrolo[2,3cjpyridine, pyrrolo[3,2-c]pyridine, pyrrolo[3,2-b]pyridine, pyrrolo[2,3-d]pyrimidine, pyrrolo [3,2-d]pyrimidine, pyrrolo [2,3-b]pyrazine, pyrazolo[1,5-a] pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo [3,2,1-hi]indole, indolizine, pyrido[1,2-a]indole, 2(1H)-pyridinone, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Some exemplary heteroaryl groups include, but are not limited to, pyridyl, furanyl, imidazolyl, benzimidazolyl, pyrimidinyl, thiophenyl, pyridazinyl, pyrazinyl, quinolinyl, indolyl, thiazolyl, naphthyridinyl, 2-amino-4-oxo-3,4-dihydropteridin-6-yl, tetrahydroisoquinolinyl, and the like. In some embodiments, 1, 2, 3, or 4 hydrogen atoms of each ring can be substituted by a substituent described herein.

The term "cyclyl" or "cycloalkyl" refers to saturated and partially unsaturated cyclic hydrocarbon groups having 3 to 12 carbons, for example, 3 to 8 carbons or 3 to 6 carbons. $C_x$ cyclyl and $C_x$-$C_y$ cycyl are typically used where X and Y indicate the number of carbon atoms in the ring system. For example, $C_3$-$C_8$ cyclyl includes cyclyls that have 3 to 8 carbon atoms in the ring system. The cycloalkyl group additionally can be optionally substituted, e.g., with 1, 2, 3, or 4 substituents, as described herein. $C_3$-$C_{10}$ cyclyl includes cyclopropyl, cyclobutyl, cyclopentyl, cyclohexyl, cyclohexenyl, 2,5-cyclohexadienyl, cycloheptyl, cyclooctyl, bicyclo [2.2.2]octyl, adamantan-1-yl, decahydronaphthyl, oxocyclohexyl, dioxocyclohexyl, thiocyclohexyl, 2-oxobicyclo [2.2.1]hept-1-yl, and the like.

The term "heterocyclyl" refers to a nonaromatic 4-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$ heterocyclyl and $C_x$-$C_y$ heterocyclyl are typically used where X and Y indicate the number of carbon atoms in the ring system. For example, $C_4$-$C_9$ heterocyclyl includes heterocyclyls that have 4-9 carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyland the like.

The terms "bicyclic" and "tricyclic" refers to fused, bridged, or joined by a single bond polycyclic ring assemblies.

The term "cyclylalkylene" means a divalent aryl, heteroaryl, cyclyl, or heterocyclyl.

As used herein, the term "fused ring" refers to a ring that is bonded to another ring to form a compound having a bicyclic structure when the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems can be saturated, partially saturated, cyclyl, heterocyclyl, aromatics, heteroaromatics, and the like.

As used herein, the term "halogen" or "halo" refers to an atom selected from fluorine, chlorine, bromine, and iodine. The term "halogen radioisotope" or "halo isotope" refers to a radionuclide of an atom selected from fluorine, chlorine, bromine and iodine.

A "halogen-substituted moiety" or "halo-substituted moiety," as an isolated group or part of a larger group, means an aliphatic, alicyclic, or aromatic moiety, as described herein, substituted by one or more "halo" atoms, as such terms are defined in this application. For example, halo-substituted alkyl includes haloalkyl, dihaloalkyl, trihaloalkyl, perhaloalkyl and the like (e.g., halosubstituted ($C_1$-$C_3$) alkyl includes chloromethyl, dichloromethyl, difluoromethyl, trifluoromethyl (—$CF_3$), 2,2,2-trifluoroethyl, perfluoroethyl, 2,2,2-trifluoro-1,1-dichloroethyl, and the like).

As used herein, the term "carbonyl" means the radical —C(O)—. It is noted that the carbonyl radical can be further substituted with a variety of substituents to form different carbonyl groups including acids, acid halides, amides, esters, ketones, and the like.

The term "carboxy" means the radical —C(O)O—. It is noted that compounds described herein containing carboxy moieties can include protected derivatives thereof, i.e., where the oxygen is substituted with a protecting group. Suitable protecting groups for carboxy moieties include benzyl, tert-butyl, and the like. The term "carboxyl" means —COOH.

The term "cyano" means the radical —CN.

The term "heteroatom" refers to an atom that is not a carbon atom. Particular examples of heteroatoms include, but are not limited to nitrogen, oxygen, sulfur and halogens. A "heteroatom moiety" includes a moiety where the atom by which the moiety is attached is not a carbon. Examples of heteroatom moieties include —N=, —NR$^N$—, —N$^+$(O$^-$)=, —O—, —S— or —S(O)$_2$—, —OS(O)$_2$—, and —SS—, wherein R$^N$ is H or a further substituent.

The term "hydroxy" means the radical —OH.

The term "imine derivative" means a derivative comprising the moiety —C(NR)—, wherein R comprises a hydrogen or carbon atom alpha to the nitrogen.

The term "nitro" means the radical —NO$_2$.

As used herein, the term "substituted" refers to independent replacement of one or more (typically 1, 2, 3, 4, or 5) of the hydrogen atoms on the substituted moiety with substituents independently selected from the group of substituents listed below in the definition for "substituents" or otherwise specified. In general, a non-hydrogen substituent can be any substituent that can be bound to an atom of the given moiety that is specified to be substituted in any suitable position (e.g., 1-, 2-, 3-, 4-, 5-, or 6-position, etc.). Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, alkylcarbanoyl, alkylene, alkylidene, alkylthios, alkynyl, amide, amido, amino, aminoalkyl, aralkyl, aralkylsulfonamido, arenesulfonamido, arenesulfonyl, aromatic, aryl, arylamino, arylcarbanoyl, aryloxy, azido, carbamoyl, carbonyl, carbonyls including ketones, carboxy, carboxylates, CF$_3$, cyano (CN), cycloalkyl, cycloalkylene, ester, ether, haloalkyl, halogen, halogen, heteroaryl, heterocyclyl, hydroxy, hydroxyalkyl, imino, iminoketone, ketone, mercapto, nitro, oxaalkyl, oxo, oxoalkyl, phosphoryl (including phosphonate and phosphinate), silyl groups, sulfonamido, sulfonyl (including sulfate, sulfamoyl and sulfonate), thiols, and ureido moieties, each of which may optionally also be substituted or unsubstituted. In some cases, two substituents, together with the carbon(s) to which they are attached to, can form a ring.

In some embodiments, moieties, such as alkyl, aryl, heteroaryl, cycloalkyl, and heterocycloalky, can be optionally substituted with one or more substituents at one or more positions, for example, halogen, alkyl, aralkyl, alkenyl, alkynyl, cycloalkyl, hydroxy, thiol, amino, azido, nitro, sulfhydryl, imino, amido, phosphate, phosphonate, phosphinate, carbonyl, carboxyl, silyl, ether, alkylthio, sulfonyl (including sulfate, sulfonamido, sulfamoyl, and sulfonate), ketone, aldehyde, ester, a heterocyclyl, an aromatic or heteroaromatic moiety, —CF$_3$, —CN, or the like.

Substituents may be protected as necessary and any of the protecting groups commonly used in the art may be employed. Non-limiting examples of protecting groups may be found, for example, in Greene et al., Protective Groups in Organic Synthesis, 3rd Ed. (New York: Wiley, 1999).

The terms "alkoxyl" or "alkoxy" as used herein refers to an alkyl group, as defined above, having an oxygen radical attached thereto. Representative alkoxyl groups include methoxy, ethoxy, propyloxy, tert-butoxy, n-propyloxy, isopropyloxy, n-butyloxy, iso-butyloxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The term "aralkyl," as used herein, refers to an alkyl group substituted with an aryl group (e.g., an aromatic or heteroaromatic group).

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups.

The term "sulfinyl" means the radical —SO—. It is noted that the sulfinyl radical can be further substituted with a variety of substituents to form different sulfinyl groups including sulfinic acids, sulfinamides, sulfinyl esters, sulfoxides, and the like.

The term "sulfonyl" means the radical —SO$_2$—. It is noted that the sulfonyl radical can be further substituted with a variety of substituents to form different sulfonyl groups including sulfonic acids (—SO$_3$H), sulfonamides, sulfonate esters, sulfones, and the like.

The term "thiocarbonyl" means the radical —C(S)—. It is noted that the thiocarbonyl radical can be further substituted with a variety of substituents to form different thiocarbonyl groups including thioacids, thioamides, thioesters, thioketones, and the like.

As used herein, the term "amino" means —NH$_2$. The term "alkylamino" means a nitrogen moiety having at least one straight or branched unsaturated aliphatic, cyclyl, or heterocyclyl radicals attached to the nitrogen. For example, representative amino groups include —NH$_2$, —NHCH$_3$, —N(CH$_3$)$_2$, —NH(C$_1$-C$_{10}$alkyl), —N(C$_1$-C$_{10}$alkyl)$_2$, and the like. The term "alkylamino" includes "alkenylamino," "alkynylamino," "cyclylamino," and "heterocyclylamino." The term "arylamino" means a nitrogen moiety having at least one aryl radical attached to the nitrogen. For example —NHaryl, and —N(aryl)$_2$. The term "heteroarylamino" means a nitrogen moiety having at least one heteroaryl radical attached to the nitrogen. For example —NHheteroaryl, and —N(heteroaryl)$_2$. Optionally, two substituents together with the nitrogen can also form a ring. Unless indicated otherwise, the compounds described herein containing amino moieties can include protected derivatives thereof. Suitable protecting groups for amino moieties include acetyl, tertbutoxycarbonyl, benzyloxycarbonyl, and the like.

The term "aminoalkyl" means an alkyl, alkenyl, and alkynyl as defined above, except where one or more substituted or unsubstituted nitrogen atoms (—N—) are positioned between carbon atoms of the alkyl, alkenyl, or alkynyl. For example, an (C$_2$-C$_6$) aminoalkyl refers to a chain comprising between 2 and 6 carbons and one or more nitrogen atoms positioned between the carbon atoms.

The term "alkoxyalkoxy" means —O-(alkyl)-O-(alkyl), such as —OCH$_2$CH$_2$OCH$_3$, and the like.

The term "alkoxycarbonyl" means —C(O)O-(alkyl), such as —C(=O)OCH$_3$, —C(=O)OCH$_2$CH$_3$, and the like.

The term "alkoxyalkyl" means -(alkyl)-O-(alkyl), such as —CH$_2$OCH$_3$, —CH$_2$OCH$_2$CH$_3$, and the like.

The term "aryloxy" means —O-(aryl), such as —O-phenyl, —O-pyridinyl, and the like.

The term "arylalkyl" means -(alkyl)-(aryl), such as benzyl (i.e., —CH$_2$phenyl), —CH$_2$-pyrindinyl, and the like.

The term "arylalkyloxy" means —O-(alkyl)-(aryl), such as —O-benzyl, —O—CH$_2$-pyridinyl, and the like.

The term "cycloalkyloxy" means —O-(cycloalkyl), such as —O-cyclohexyl, and the like.

The term "cycloalkylalkyloxy" means —O-(alkyl)-(cycloalkyl, such as —OCH$_2$cyclohexyl, and the like.

The term "aminoalkoxy" means —O-(alkyl)-NH$_2$, such as —OCH$_2$NH$_2$, —OCH$_2$CH$_2$NH$_2$, and the like.

The term "mono- or di-alkylamino" means —NH(alkyl) or —N(alkyl)(alkyl), respectively, such as —NHCH$_3$, —N(CH$_3$)$_2$, and the like.

The term "mono- or di-alkylaminoalkoxy" means —O-(alkyl)-NH(alkyl) or —O-(alkyl)-N(alkyl)(alkyl), respectively, such as —OCH$_2$NHCH$_3$, —OCH$_2$CH$_2$N(CH$_3$)$_2$, and the like.

The term "arylamino" means —NH(aryl), such as —NH-phenyl, —NH-pyridinyl, and the like.

The term "arylalkylamino" means —NH-(alkyl)-(aryl), such as —NH-benzyl, —NHCH$_2$-pyridinyl, and the like.

The term "alkylamino" means —NH(alkyl), such as —NHCH$_3$, —NHCH$_2$CH$_3$, and the like.

The term "cycloalkylamino" means —NH-(cycloalkyl), such as —NH-cyclohexyl, and the like.

The term "cycloalkylalkylamino"-NH-(alkyl)-(cycloalkyl), such as —NHCH$_2$-cyclohexyl, and the like.

The term "substituted or unsubstituted organic group," as used herein," refers to any carbon-based moiety as set forth above. Suitable organic groups are amply described herein and include, for example, alkyl, alkenyl, alkynyl, aryl, heteroaryl, cycloalkyl, and heterocyclyl. Substitution of such moieties is also described herein.

It is noted in regard to all of the definitions provided herein that the definitions should be interpreted as being open ended in the sense that further substituents beyond those specified may be included. Hence, a C$_1$ alkyl indicates that there is one carbon atom but does not indicate what are the substituents on the carbon atom. Hence, a C$_1$ alkyl comprises methyl (i.e., —CH$_3$) as well as —CR$_a$R$_b$R$_c$ where R$_a$, R$_b$, and R$_c$ can each independently be hydrogen or any other substituent where the atom alpha to the carbon is a heteroatom or cyano. Hence, CF$_3$, CH$_2$OH, and CH$_2$CN are all C$_1$ alkyls.

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

In any of the embodiments herein, the phrase "salt" or "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Lists of suitable salts are found in Remington's Pharmaceutical Sciences, 18th ed., Mack Publishing Company, Easton, Pa., 1990, p. 1445, and Journal of Pharmaceutical Science, 66, 2-19 (1977). For example, the salt can be selected from the group consisting of acetate, benzoate, besylate, bitartrate, bromide, carbonate, chloride, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, oxalate, pamoate, phosphate, diphosphate, salicylate, disalicylate, stearate, succinate, sulfate, tartrate, tosylate, triethiodide, trifluoroacetate, and valerate.

A pharmaceutical composition comprising at least one compound or pharmaceutically acceptable salt of a compound of formula (I) and a pharmaceutically acceptable carrier.

The methods described herein comprise administering a compound of formula (I) or a pharmaceutically acceptable salt thereof in the form of a pharmaceutical composition. In particular, a pharmaceutical composition will comprise at least one compound of formula (I) or a pharmaceutically acceptable salt thereof and a pharmaceutically acceptable carrier. The pharmaceutically acceptable excipients described herein, for example, vehicles, adjuvants, carriers or diluents, are well-known to those who are skilled in the art and are readily available to the public. Typically, the pharmaceutically acceptable carrier is one that is chemically inert to the active compounds and one that has no detrimental side effects or toxicity under the conditions of use.

The pharmaceutical compositions can be administered as oral, sublingual, transdermal, subcutaneous, topical, absorption through epithelial or mucocutaneous linings, intravenous, intranasal, intraarterial, intramuscular, intratumoral, peritumoral, interperitoneal, intrathecal, rectal, vaginal, or aerosol formulations. In some aspects, the pharmaceutical composition is administered orally or intravenously.

In accordance with any of the embodiments, the compound of formula (I) or a pharmaceutically acceptable salt thereof can be administered orally to a subject in need thereof. Formulations suitable for oral administration can consist of (a) liquid solutions, such as an effective amount of the compound dissolved in diluents, such as water, saline, or orange juice and include an additive, such as cyclodextrin (e.g., α-, β-, or γ-cyclodextrin, hydroxypropyl cyclodextrin) or polyethylene glycol (e.g., PEG400); (b) capsules, sachets, tablets, lozenges, and troches, each containing a predetermined amount of the active ingredient, as solids or granules; (c) powders; (d) suspensions in an appropriate liquid; and (e) suitable emulsions and gels. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound of formula (I) or a salt thereof can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the inhibitors in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The inhibitors can be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Topically applied compositions are generally in the form of liquids (e.g., mouthwash), creams, pastes, lotions and gels. Topical administration includes application to the oral mucosa, which includes the oral cavity, oral epithelium, palate, gingival, and the nasal mucosa. In some embodiments, the composition contains at least one active component and a suitable vehicle or carrier. It may also contain other components, such as an anti-irritant. The carrier can be a liquid, solid or semi-solid. In embodiments, the composition is an aqueous solution, such as a mouthwash. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

The compound of formula (I) or a pharmaceutically acceptable salt thereof, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

The dose administered to the subject, particularly a human and other mammals, in accordance with the present invention should be sufficient to affect the desired response. One skilled in the art will recognize that dosage will depend upon a variety of factors, including the age, condition or disease state, predisposition to disease, genetic defect or defects, and body weight of the mammal. The size of the dose will also be determined by the route, timing and frequency of administration as well as the existence, nature, and extent of any adverse side-effects that might accompany the administration of a particular inhibitor and the desired effect. It will be appreciated by one of skill in the art that various conditions or disease states may require prolonged treatment involving multiple administrations. The inventive methods comprise administering an effective amount of a compound of formula (I) or a pharmaceutically acceptable salt thereof. An "effective amount" means an amount sufficient to show a meaningful benefit in an individual such that one or more symptoms of the disease (e.g., cancer) are prevented, reduced, halted, or eliminated subsequent to administration of a compound of formula (I) or a pharmaceutically acceptable salt thereof, thereby effectively treating the disease to at least some degree. For example, the meaningful benefit can be promoting at least one aspect of tumor cell cytotoxicity (e.g., inhibition of growth, inhibiting survival of a cancer cell, reducing proliferation, reducing size and/or mass of a tumor (e.g., solid tumor)), or treatment, healing, prevention, delay of onset, halting, or amelioration of other relevant medical condition(s) associated with a particular cancer. The meaningful benefit observed in the subject to be treated can be to any suitable degree (10, 20, 30, 40, 50, 60, 70, 80, 90% or more).

Effective amounts may vary depending upon the biological effect desired in the individual, condition to be treated, and/or the specific characteristics of the compound of formula (I) or a pharmaceutically acceptable salt thereof, and the individual. In this respect, any suitable dose of the compound of formula (I) or a pharmaceutically acceptable salt thereof can be administered to the subject (e.g., human), according to the disease (e.g., type of cancer) to be treated. Various general considerations taken into account in determining the "effective amount" are known to those of skill in the art and are described, e.g., in Gilman et al., eds., Goodman And Gilman's: *The Pharmacological Bases of Therapeutics,* 8th ed., Pergamon Press, 1990; and Remington's Pharmaceutical Sciences, 17th Ed., Mack Publishing Co., Easton, Pa., 1990, each of which is herein incorporated by reference. The dose of the compound of formula (I) or a pharmaceutically acceptable salt thereof desirably comprises about 0.1 mg per kilogram (kg) of the body weight of the mammal (mg/kg) to about 400 mg/kg (e.g., about 0.75 mg/kg, about 5 mg/kg, about 30 mg/kg, about 75 mg/kg, about 100 mg/kg, about 200 mg/kg, or about 300 mg/kg). In another embodiment, the dose of the compound of formula (I) comprises about 0.5 mg/kg to about 300 mg/kg (e.g., about 0.75 mg/kg, about 5 mg/kg, about 50 mg/kg, about 100 mg/kg, or about 200 mg/kg), about 10 mg/kg to about 200 mg/kg (e.g., about 25 mg/kg, about 75 mg/kg, or about 150 mg/kg), or about 50 mg/kg to about 100 mg/kg (e.g., about 60 mg/kg, about 70 mg/kg, or about 90 mg/kg). Alternatively, the dose can be 100 mg/kg or less (e.g., 75 mg/kg or less, 50 mg/kg or less, 25 mg/kg or less, 10 mg/kg or less, 5 mg/kg or less, or about 1 mg/kg or less).

In an aspect, a compound of formula (I) or a salt thereof inhibits one or more enzymes selected from IDO and TDO. Preferably, a compound of formula (I) or a salt thereof inhibits both IDO and TDO and acts as a dual inhibitor. Accordingly, the present invention provides a method of inhibiting an indoleamine 2,3-dioxygenase (IDO) and/or tryptophan 2,3-dioxygenase (TDO) enzyme in a cell, the method comprising contacting an effective amount of a compound of formula (I) or a pharmaceutically acceptable salt thereof to a cell in need of such inhibition (e.g., a cell that overexpresses IDO and/or TDO). For example, the cell can be any cell that overexpresses IDO and/or TDO such as cells from tissue that has or is associated with cancer (e.g., colon cancer, breast cancer, ovarian cancer, brain cancer, including brain glioblastoma, leukemia, lung cancer, including non-small cell lung cancer, thoracic cancer, pancreatic cancer, melanoma, bladder cancer, rectal cancer, head and neck cancer), neurological and/or brain disorders (e.g., Parkinson's disease, Oshtoran syndrome, cerebral malaria, Alzheimer's disease, Huntington's disease, depression, and ischemic brain injury), eye disorders (e.g., cataract formation), and HIV infection. In accordance with an embodiment, the cells requiring inhibition are cancer cells selected from colon cancer, breast cancer, ovarian cancer, brain cancer, including brain glioblastoma, leukemia, lung cancer, including non-small cell lung cancer, thoracic cancer, pancreatic cancer, melanoma, bladder cancer, rectal cancer, or head and neck cancer. In certain preferred embodiments, the cancer cell is brain cancer, colon cancer, or breast cancer.

Elevated levels of IDO and TDO are associated with certain diseases, and it is envisioned that inhibiting one or both of IDO and TDO is a viable treatment of such diseases. While not wishing to be bound by any theory, it is believed that when IDO and TDO are overexpressed in certain cells (e.g., cancer cells), the ability to inhibit IDO and TDO with an IDO and/or TDO inhibitor reduces kynurenine levels, which allow for the immune system to act on the treated cells. Thus, provided is a method of treating an IDO- and/or TDO-mediated disease in a subject. The method comprises administering a pharmaceutically effective amount of a compound of formula (I) or a pharmaceutically acceptable salt thereof to a subject in need of such treatment. Preferably, the IDO- and/or TDO-mediated disease is selected from the group consisting of cancer (e.g., colon cancer, breast cancer, ovarian cancer, brain cancer, including brain glioblastoma, leukemia, lung cancer, including non-small cell lung cancer, thoracic cancer, pancreatic cancer, melanoma, bladder cancer, rectal cancer, or head and neck cancer), neurological and/or brain disorders (e.g., Parkinson's disease, Oshtoran syndrome, cerebral malaria, Alzheimer's disease, Huntington's disease, depression, and ischemic brain injury), eye disorders (e.g., cataract formation), and HIV infection. In accordance with an embodiment, the cancer is colon cancer, breast cancer, ovarian cancer, brain cancer, including brain glioblastoma, leukemia, lung cancer, including non-small cell lung cancer, thoracic cancer, pancreatic cancer, melanoma, bladder cancer, rectal cancer, or head and neck cancer. In certain preferred embodiments, the cancer is brain cancer, colon cancer, or breast cancer.

The invention further provides a method of treating a subject with cancer cells resistant to an anti-cancer agent, comprising administering to the subject an effective amount of the compound of formula (I) or a pharmaceutically acceptable salt thereof, and the anti-cancer agent, whereby the compound or pharmaceutically acceptable salt thereof re-sensitizes the cancer cells to the anti-cancer agent. The cancer cell is the same as described herein. In accordance with an embodiment, the cancer cells are colon cancer, breast cancer, ovarian cancer, brain cancer, including brain glioblastoma, leukemia, lung cancer, including non-small cell lung cancer, thoracic cancer, pancreatic cancer, melanoma, bladder cancer, rectal cancer, head and neck cancer. In certain preferred embodiments, the cancer is brain cancer, colon cancer, or breast cancer.

In certain embodiments of this method, the compound of formula (I) or a pharmaceutically acceptable salt thereof can be co-administered with an anti-cancer agent (e.g., a chemotherapeutic agent) and/or radiation therapy. In an aspect, the method comprises administering an amount of a compound or salt that is effective to sensitize the cancer cells to one or more therapeutic regimens (e.g., chemotherapy or radiation therapy). The terms "co-administered" or "co-administration" refer to simultaneous or sequential administration. A compound may be administered before, concurrently with, or after administration of another compound using any suitable time frame.

One or more than one, e.g., two, three, or more anti-cancer agents can be administered. In this regard, the present invention is directed a pharmaceutical composition comprising a pharmaceutically acceptable carrier and a combination of the compound of formula (I) or a pharmaceutically acceptable salt thereof and at least one anti-cancer agent (e.g., chemotherapeutic agent).

Examples of anti-cancer agents include platinum compounds (e.g., cisplatin, carboplatin, oxaliplatin), alkylating agents (e.g., cyclophosphamide, ifosfamide, chlorambucil, nitrogen mustard, thiotepa, melphalan, busulfan, procarbazine, streptozocin, temozolomide, dacarbazine, bendamustine), antitumor antibiotics (e.g., daunorubicin, doxorubicin, idarubicin, epirubicin, mitoxantrone, bleomycin, mytomycin C, plicamycin, dactinomycin), taxanes (e.g., paclitaxel and docetaxel), antimetabolites (e.g., 5-fluorouracil, cytarabine, premetrexed, thioguanine, floxuridine, capecitabine, and methotrexate), nucleoside analogues (e.g., fludarabine, clofarabine, cladribine, pentostatin, nelarabine), topoisomerase inhibitors (e.g., topotecan and irinotecan), hypomethylating agents (e.g., azacitidine and decitabine), proteosome inhibitors (e.g., bortezomib), epipodophyllotoxins (e.g., etoposide and teniposide), DNA synthesis inhibitors (e.g., hydroxyurea), vinca alkaloids (e.g., vicristine, vindesine, vinorelbine, and vinblastine), tyrosine kinase inhibitors (e.g., imatinib, dasatinib, nilotinib, sorafenib, sunitinib), monoclonal antibodies (e.g., rituximab, cetuximab, panetumumab, tositumomab, trastuzumab, alemtuzumab, gemtuzumab ozogamicin, bevacizumab), nitrosoureas (e.g., carmustine, fotemustine, and lomustine), enzymes (e.g., L-Asparaginase), biological agents (e.g., interferons and interleukins), hexamethylmelamine, mitotane, angiogenesis inhibitors (e.g., thalidomide, lenalidomide), steroids (e.g., prednisone, dexamethasone, and prednisolone), hormonal agents (e.g., tamoxifen, raloxifene, leuprolide, bicaluatmide, granisetron, flutamide), aromatase inhibitors (e.g., letrozole and anastrozole), arsenic trioxide, tretinoin, nonselective cyclooxygenase inhibitors (e.g., nonsteroidal anti-inflammatory agents, salicylates, aspirin, piroxicam, ibuprofen, indomethacin, naprosyn, diclofenac, tolmetin, ketoprofen, nabumetone, oxaprozin), selective cyclooxygenase-2 (COX-2) inhibitors, or any combination thereof.

For purposes of the present invention, the term "subject" typically is directed to a mammal. For example, the subject can be any subject with a disease that requires chemotherapy and/or radiation therapy. Mammals include, but are not limited to, the order Rodentia, such as mice, and the order Logomorpha, such as rabbits. In some aspects, the mammals are from the order Carnivora, including Felines (cats) and Canines (dogs), Artiodactyla, including Bovines (cows) and Swines (pigs) or of the order Perssodactyla, including Equines (horses). In some aspects, the mammals are of the order Primates, Ceboids, or Simioids (monkeys) or of the order Anthropoids (humans and apes). In embodiments of the invention, the subject is a human.

The invention is further illustrated by the following embodiments.

(1) A compound of formula (I):

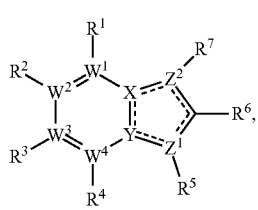

wherein
$W^1$, $W^2$, $W^3$, and $W^4$ are each independently CH or N;
$R^1$, $R^2$, $R^3$, and $R^4$ are each independently H, alkyl, haloalkyl, halogen, or CN;
X, Y, $Z^1$, and $Z^2$ are independently C or N;
$R^5$ and $R^7$ are independently absent, H, $C_1$-$C_6$ alkyl, or cycloalkyl;
$R^6$ is a group selected from one of the following:

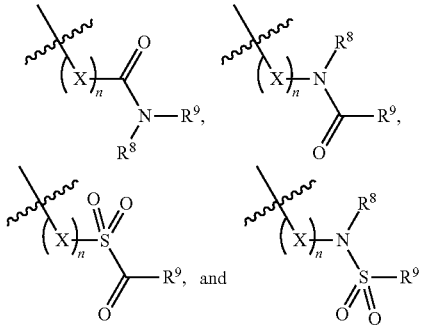

wherein
$R^8$ is selected from H and a substituted or unsubstituted organic group;
$R^9$ is selected from H and a substituted or unsubstituted organic group;
X is selected from $C(R^{10})_2$ and $NR^{11}$;
each $R^{10}$ is selected from a group consisting of H, $C_1$-$C_6$ alkyl, and cycloalkyl;
$R^{11}$ is selected from H and a substituted or unsubstituted organic group; and
n is 0 or 1 if X is $NR^{11}$; or n is 0, 1, or 2 if X is $C(R^{10})_2$, wherein each dashed line is a single bond or double bond as valences permit,
or a pharmaceutically acceptable salt thereof.

(2) The compound of embodiment (1), wherein $R^9$ is the following formula

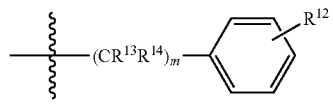

wherein $R^{12}$ is selected from a group consisting of H, $(CH_2)_oNR^{15}R^{16}$, and $(CH_2)_oC(=O)NR^{15}R^{16}$, $R^{13}$ and $R^{14}$ are the same or different and are each H or alkyl, $R^{15}$ and $R^{16}$ are the same or different and are each H, alkyl, or combine, along with the N to which they are bonded, to form an optionally substituted heterocyclic ring containing N and optionally one or more additional heteroatoms selected from nitrogen, oxygen, and sulfur, m is 0 to 6, and o is 0 to 4, or a pharmaceutically acceptable salt thereof.

(3) The compound of embodiment (2), wherein $R^{13}$ and $R^{14}$ are each H, or $R^{13}$ and $R^{14}$ are each methyl, or $R^{13}$ is H and $R^{14}$ is methyl, or a pharmaceutically acceptable salt thereof.

(4) The compound of embodiment (2) or (3), wherein m is 1 or 2, or a pharmaceutically acceptable salt thereof.

(5) The compound of any one of embodiments (2)-(4), wherein o is 0 or 1, or a pharmaceutically acceptable salt thereof.

(6) The compound of any one of embodiments (2)-(5), wherein $R^{15}$ and $R^{16}$ combine, along with the N to which they are bonded, to form heterocyclic ring selected from morpholinyl, piperazinyl, piperidinyl, and pyrrolyl, each of which is optionally substituted with one or more substitutents selected from alkyl, acetyl, and methylsulfonyl.

(7) The compound of any one of embodiments (1)-(6), wherein one of $R^1$, $R^2$, $R^3$, and $R^4$ is alkyl, haloalkyl, halogen, or CN and the remaining three substituents are H, or a pharmaceutically acceptable salt thereof.

(8) The compound of any one of embodiments (1)-(6), wherein each of $R^1$, $R^2$, $R^3$, and $R^4$ is H, or a pharmaceutically acceptable salt thereof.

(9) The compound of any one of embodiments (1)-(8), wherein $W^1$, $W^2$, $W^3$, and $W^4$ are each CH, or one of $W^1$, $W^2$, $W^3$, and $W^4$ is N, and the remaining three substituents are each CH, or a pharmaceutically acceptable salt thereof.

(10) The compound of any one of embodiments (1)-(9), wherein X and $Z^2$ are nitrogen; and Y and $Z^1$ are carbon, or a pharmaceutically acceptable salt thereof.

(11) The compound of any one of embodiments (1)-(10), wherein the compound of formula (I) is a compound of formula (Ia)

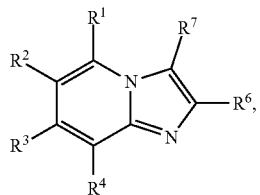
(Ia)

or a pharmaceutically acceptable salt thereof.

(12) The compound of embodiment (1) that is selected from:

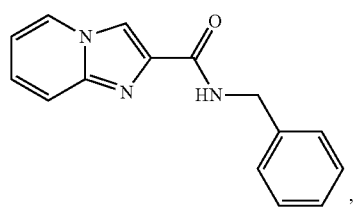
(CB516)

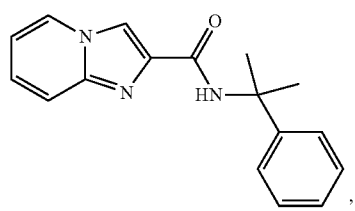
(CB517)

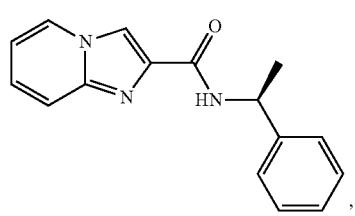
(CB518)

-continued

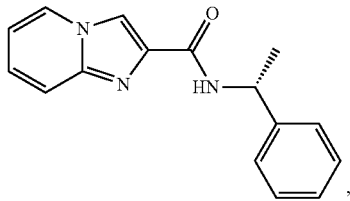
(CB512)

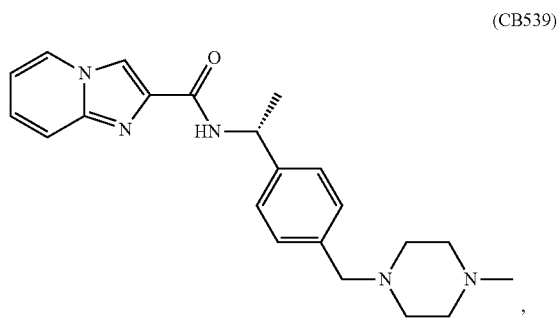
(CB539)

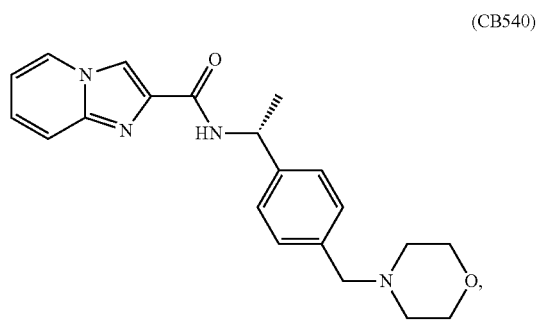
(CB540)

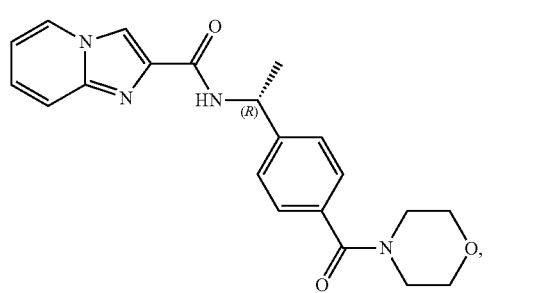
(CB533)

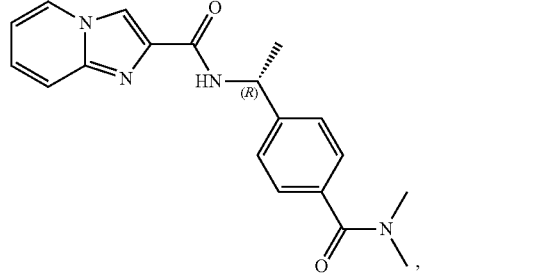
(CB532)

-continued
(CB534)
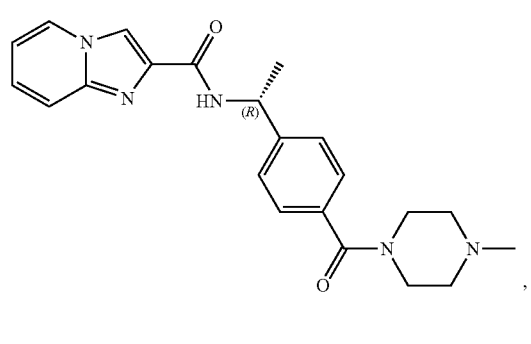
(CB581)
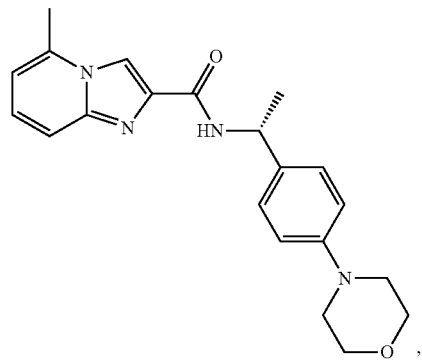
(CB548)
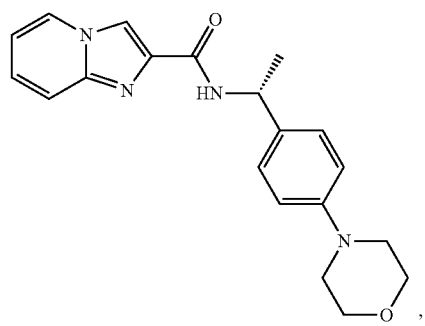
(CB582)
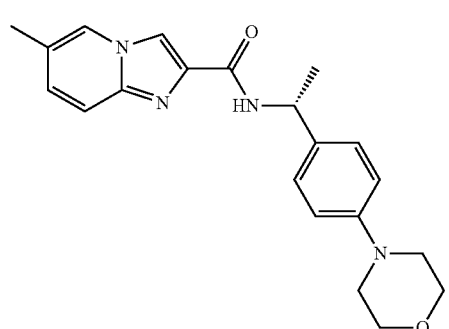
(CB549)
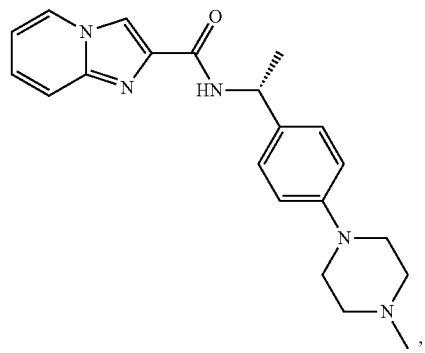
(CB583)
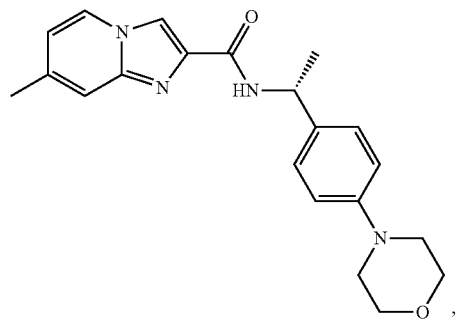
(CB550)
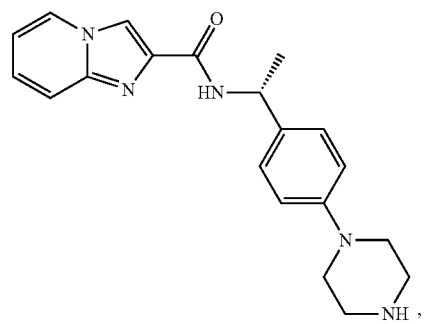
(CB556)
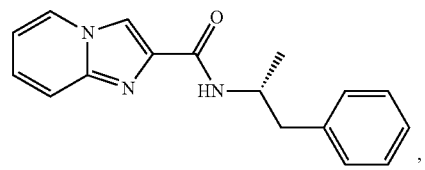
(CB584)
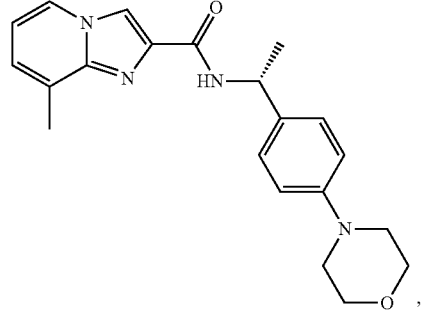

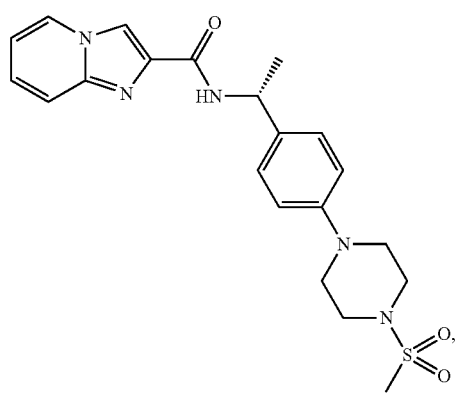
(CB585)
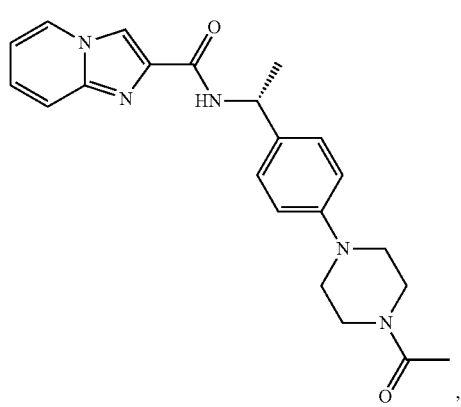
(CB586)
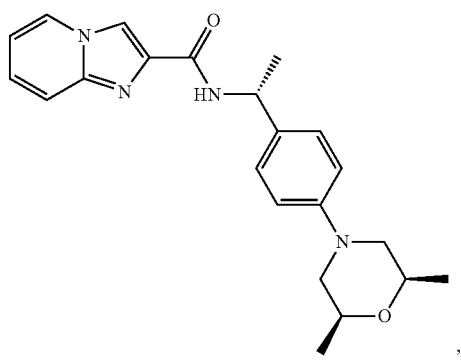
(CB590)
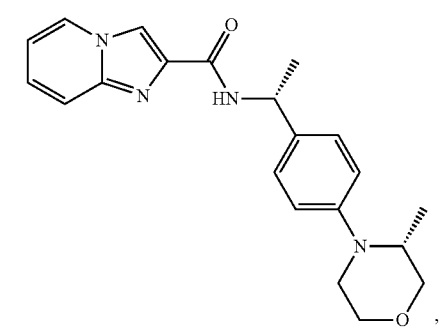
(CB595)
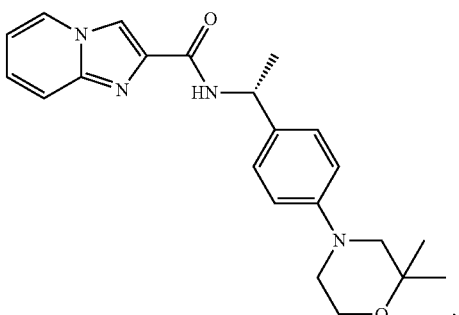
(CB596)
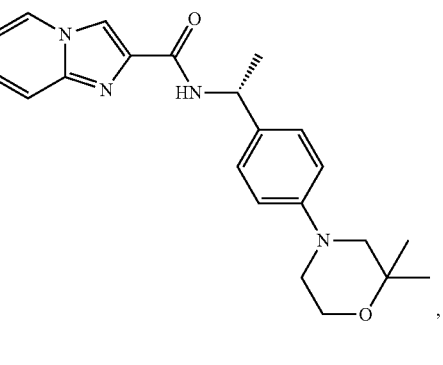
(CB597)
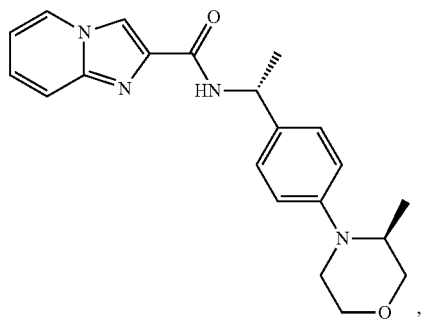
(CB598)
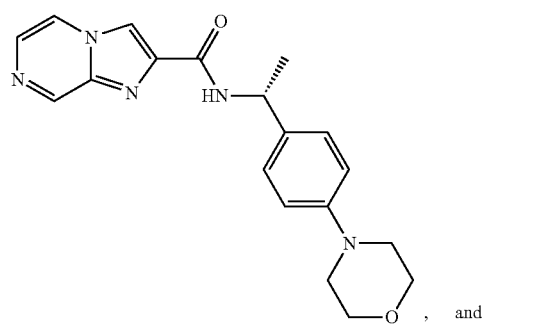
(CB599) , and
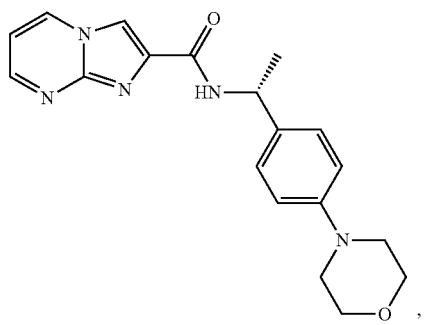
or a pharmaceutically acceptable salt thereof.
(13) The compound of any one of embodiments (1)-(9), wherein X and $Z^1$ are carbon; and Y and $Z^2$ are nitrogen, or a pharmaceutically acceptable salt thereof.
(14) The compound of any one of embodiments (1)-(9) and (13), wherein the compound of formula (I) is a compound of formula (Ib)

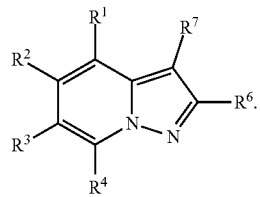

(Ib)

or a pharmaceutically acceptable salt thereof.

(15) The compound of embodiment (1) that is selected from:

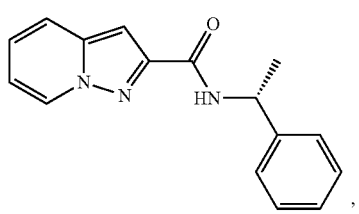

(CB511)

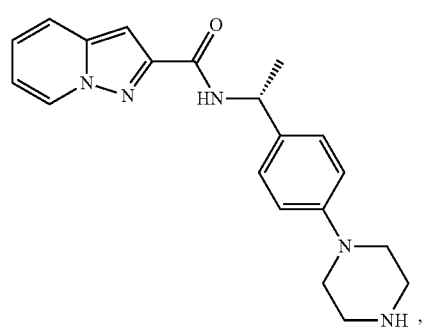

(CB570)

(CB571)

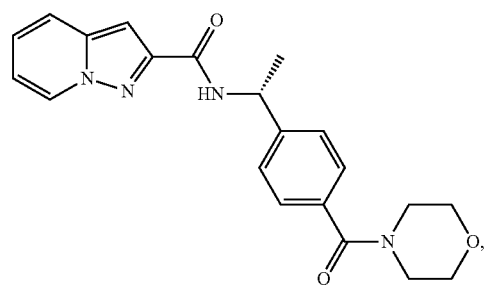

(CB569)

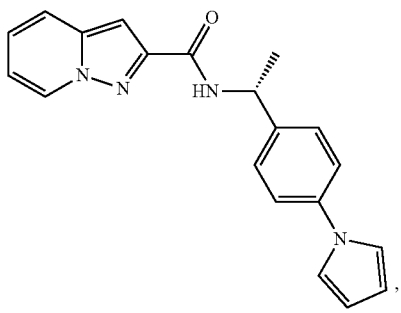

(CB629)

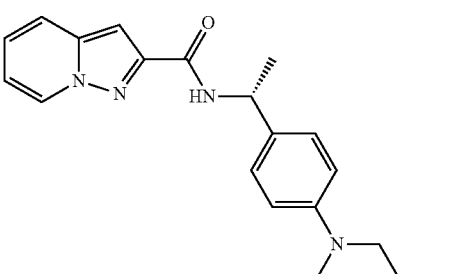

(CB630)

(CB633)

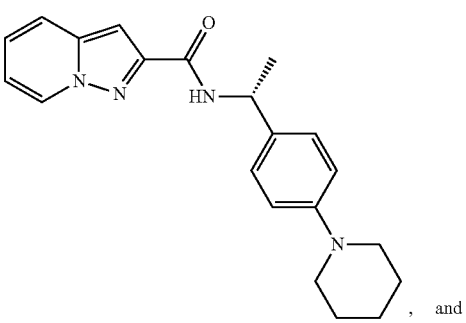

, and (CB600)

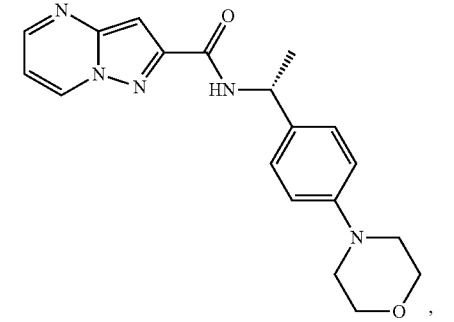

pharmaceutically acceptable salt thereof.

(16) The compound of any one of embodiments (1)-(9), wherein X and Y are carbon; and $Z^1$ and $Z^2$ are nitrogen, or a pharmaceutically acceptable salt thereof.

(17) The compound of any one of embodiments (1)-(9) and (16), wherein the compound of formula (I) is a compound of formula (Ic)

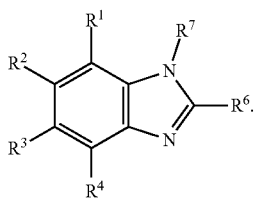

(Ic)

or a pharmaceutically acceptable salt thereof.

(18) The compound of embodiment (1), selected from:

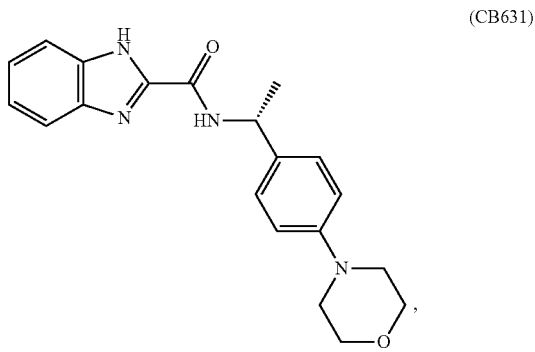 [SMILES: C[C@@H](NC(=O)c1nc2ccccc2[nH]1)c1ccc(N2CCOCC2)cc1]

(CB631)

or a pharmaceutically acceptable salt thereof.

(19) A pharmaceutical composition comprising at least one compound or pharmaceutically acceptable salt of any of embodiments (1)-(18) and a pharmaceutically acceptable carrier.

(20) A method of treating a disease in a subject, wherein the disease is selected from the group consisting of cancer, Parkinson's disease, oshtoran syndrome, cataract formation, cerebral malaria, Alzheimer's disease, HIV infection, Huntington's disease, depression, and ischemic brain injury, the method comprising administering a pharmaceutically effective amount of the compound of any one of embodiments (1)-(18) or a pharmaceutically acceptable salt thereof to a subject in need of such treatment.

(21) A method of inhibiting an indoleamine 2,3-dioxygenase (IDO) and/or tryptophan 2,3-dioxygenase (TDO) enzyme in a cell, the method comprising administering a pharmaceutically effective amount of the compound of any one of embodiments (1)-(18) or a pharmaceutically acceptable salt thereof to a cell in need of such inhibition.

The following examples further illustrate the invention but, of course, should not be construed as in any way limiting its scope.

EXAMPLES

NMR spectra were recorded in CDCl$_3$ and DMSO-d$_6$ solution in 5-mm o.d. tubes (Norell, Inc. 507-HP, Morgantown, N.C., USA) at 30° C. and were collected on Varian VNMRS-400 at 400 MHz for $^1$H (Varian, Inc., Palo Alto, Calif., USA). The chemical shifts (δ) are relative to tetramethylsilane (TMS=0.00 ppm) and expressed in ppm. LC/MS was taken on Ion-trap Mass Spectrometer on FINNIGAN Thermo LCQ Advantage MAX, Agilent LC 1200 series (Column: YMC Hydrosphere (C18, Ø4.6×50 mm, 3 m, 120 Å, 40° C.) operating in ESI(+) ionization mode; flow rate=1.0 mL/min (Thermo Fisher Scientific, Waltham, Mass., USA). Mobile phase=0.01% heptafluorobutyric acid (HFBA) and 1.0% isopropyl alcohol (IPA) in water or CH$_3$CN.

Intermediate Example 1

This example is directed to the synthesis of (R)-1-(4-((4-methylpiperazin-1-yl)methyl)phenyl)ethanamine (intermediate 1). See FIG. 1.

Step A: (R)-methyl 4-(1-(tert-butoxycarbonylamino)ethyl)benzoate

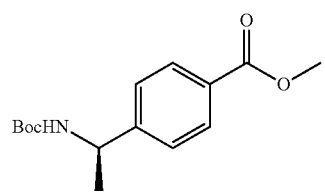 [SMILES: COC(=O)c1ccc([C@@H](C)NC(=O)OC(C)(C)C)cc1]

To a solution of (R)-methyl 4-(1-aminoethyl)benzoate (1.00 g, 5.58 mmol) in dichloromethane (DCM) (28 mL) was added triethylamine (TEA) (1.71 mL, 12.3 mmol) followed (Boc)$_2$O (1.55 mL, 6.70 mmol) at room temperature. The reaction mixture was stirred at room temperature for 2 h under N$_2$ atmosphere, and quenched with saturated aq. NH$_4$C$_1$. The mixture was extracted with DCM, dried over Na$_2$SO$_4$, filtered, and concentrated in vacuo. The residue was purified by column chromatography on SiO$_2$ (Hexane:EtOAc=4:1 to 2:1) to afford the (R)-methyl 4-(1-(tert-butoxycarbonylamino)ethyl)benzoate (1.65 g, quant.) as a white solid. $^1$H-NMR (CDCl$_3$, Varian, 400 MHz): δ 1.41 (12H, brs), 3.90 (3H, s), 4.83 (1H, brs), 7.36 (2H, d, J=8.0 Hz), 8.00 (2H, d, J=8.0 Hz). *NH peak was not observed.

Step B: (R)-tert-butyl 1-(4-(hydroxymethyl)phenyl)ethylcarbamate

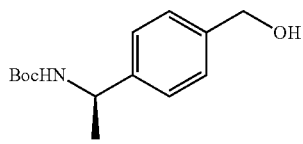

To a solution of (R)-methyl 4-(1-(tert-butoxycarbonylamino)ethyl)benzoate (1.65 g, 5.93 mmol) in dry tetrahydrofuran (THF) (30 mL) was added lithium aluminum hydride (LAH) (7.12 mL, 7.12 mmol; 1 M solution in THF) at 0° C. under N$_2$ atmosphere. The reaction mixture was stirred at room temperature for 1 h, and then quenched with Na$_2$SO$_4$.10H$_2$O at 0° C. The reaction mixture was filtered through a CELITE™ (Sigma-Aldrich, St. Louis, Mo., USA) pad and washed with EtOAc. The filtrate was concentrated in vacuo. The residue was purified by column chromatography on SiO$_2$ (Hexane:EtOAc=2:1) to afford the (R)-tert-butyl 1-(4-(hydroxymethyl)phenyl)ethylcarbamate (1.08 g, 72%) as a colorless oil. $^1$H-NMR (CDCl$_3$, Varian, 400 MHz): δ 1.42 (12H, s), 1.76 (1H, t, J=5.6 Hz), 4.67 (2H, d, J=5.2 Hz), 4.97 (1H, brs), 7.28-7.34 (4H, m). *NH peak was not observed.

Step C: (R)-1-(4-(chloromethyl)phenyl)ethanamine hydrochloride

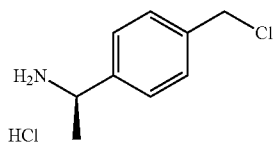

To a solution of (R)-tert-butyl 1-(4-(hydroxymethyl)phenyl)ethylcarbamate (1.08 g, 4.30 mol) in DCM (22 mL) was added SOCl$_2$ (627 µL, 8.59 mmol) at room temperature. The reaction mixture was stirred at room temperature for overnight, and then concentrated in vacuo. The residue was triturated with acetonitrile (ACN) and diethyl ether to afford the (R)-1-(4-(chloromethyl)phenyl)ethanamine hydrochloride (477 mg, 54%) as a white solid. $^1$H-NMR (DMSO-d$_6$, Varian, 400 MHz): δ 1.50 (3H, d, J=5.2 Hz), 4.40 (1H, q, J=6.8 Hz), 4.77 (2H, s), 7.48-7.53 (4H, m), 8.45 (3H, brs).

Step D: (R)-2,2,2-trifluoro-N-(1-(4-((4-methylpiperazin-1-yl)methyl)phenyl) ethyl)acetamide

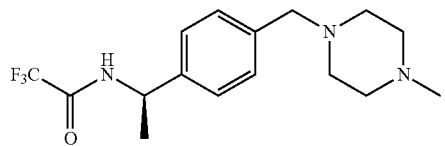 [SMILES: C[C@@H](NC(=O)C(F)(F)F)c1ccc(CN2CCN(C)CC2)cc1]

To a solution of (R)-1-(4-(chloromethyl)phenyl)ethanamine hydrochloride (100 mg, 0.49 mmol) in DCM (2.5 mL) was added trifluoroacetic anhydride (82.0 µL, 0.58 mmol) and TEA (149 µL, 1.07 mmol) at 0° C. After stirring at room temperature for 1 h, the reaction mixture was concentrated in vacuo. The obtained residue was treated with K$_2$CO$_3$ (201 mg, 1.45 mmol) and 1-methylpiperazine (81.0 µL, 0.728 mmol) in ACN (2.5 mL) and the reaction mixture was stirred at 90° C. for overnight. The mixture was filtered through a CELITE™ (Sigma-Aldrich, St. Louis, Mo., USA) pad and the filtrate was concentrated in vacuo. The residue was purified by column chromatography on NH—SiO$_2$ (Hexane:EtOAc=3:2) to afford the (R)-2,2,2-trifluoro-N-(1-(4-((4-methylpiperazin-1-yl)methyl)phenyl)ethyl)acetamide (142 mg, 89%) as a yellow solid. $^1$H-NMR (CDCl$_3$, Varian, 400 MHz): δ 1.58 (3H, d, J=6.8 Hz), 1.64 (4H, s), 2.28 (3H, s), 2.45 (4H, brs), 3.50 (2H, s), 5.10-5.17 (1H, m), 6.43 (1H, brs), 7.26 (2H, d, J=7.6 Hz), 7.33 (2H, d, J=8.4 Hz).

Step E: (R)-1-(4-((4-methylpiperazin-1-yl)methyl)phenyl)ethanamine

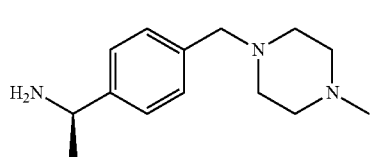 [SMILES: C[C@@H](N)c1ccc(CN2CCN(C)CC2)cc1]

To a solution of (R)-2,2,2-trifluoro-N-(1-(4-((4-methylpiperazin-1-yl)methyl)phenyl)ethyl)acetamide (120 mg, 0.36 mmol) in EtOH (3 mL) was added 6 N aq. NaOH (304 µL, 1.82 mmol) at room temperature. The reaction mixture was stirred at room temperature for 3 h, and then concentrated in vacuo. The residue was partitioned between water and EtOAc. The separated aqueous layer was extracted with EtOAc. The combined organic layers were washed with brine, dried over Na$_2$SO$_4$, filtered, and concentrated in vacuo to afford the (R)-1-(4-((4-methylpiperazin-1-yl)methyl)phenyl)ethanamine (67 mg, 79%) as a yellow oil, which was used for the next step without further purification. $^1$H-NMR (CDCl$_3$, Varian, 400 MHz): δ 1.38 (3H, d, J=6.8 Hz), 1.77 (4H, brs), 2.28 (3H, s), 2.45 (4H, brs), 3.49 (2H, s), 4.10 (1H, q, J=6.4 Hz), 7.27-7.30 (4H, m). *NH$_2$ peak was not observed.

Intermediate Example 2

Figure 2:
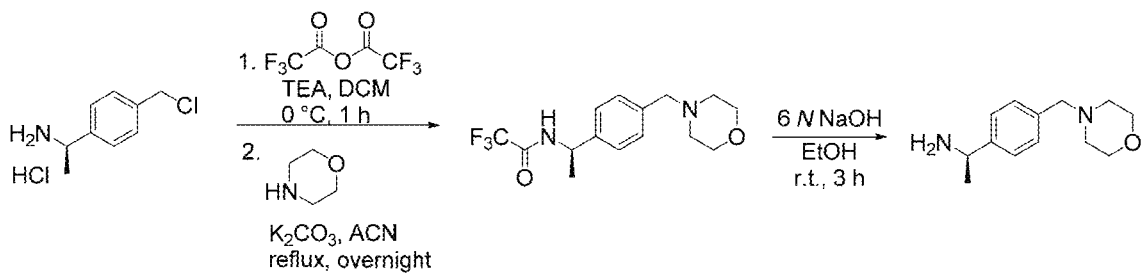
FIG. 2 is an alternative chemical scheme depicting the synthesis of (R)-1-(4-((4-methylpiperazin-1-yl)methyl)phenyl)ethanamine (intermediate 2).

This example is directed to an alternative synthesis of (R)-1-(4-((4-methylpiperazin-1-yl)methyl)phenyl) ethanamine (intermediate 2). See FIG. 2.

Step A: (R)-2,2,2-trifluoro-N-(1-(4-(morpholinomethyl)phenyl)ethyl)acetamide

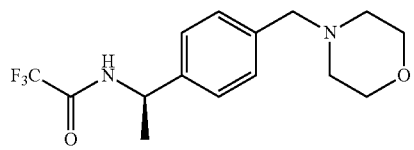 [SMILES: C[C@@H](NC(=O)C(F)(F)F)c1ccc(CN2CCOCC2)cc1]

To a solution of (R)-1-(4-(chloromethyl)phenyl) ethanamine hydrochloride (step C of intermediate 1, 150 mg, 0.73 mmol) in DCM (2.5 mL) was added trifluoroacetic anhydride (123 µL, 0.87 mmol) and TEA (223 µL, 1.60 mmol) at 0° C. After stirring at room temperature for 1 h, the reaction mixture was concentrated in vacuo. The obtained residue was treated with K$_2$CO$_3$ (302 mg, 2.18 mmol) and 1-methylpiperazine (94.0 µL, 1.09 mmol) in ACN (2.5 mL) and the reaction mixture was stirred overnight at 90° C. The mixture was filtered through a Celite pad and the filtrate was concentrated in vacuo. The residue was purified by column chromatography on NH—SiO$_2$ (Hexane:EtOAc=7:3) to afford the (R)-2,2,2-trifluoro-N-(1-(4-(morpholinomethyl) phenyl)ethyl)acetamide (242 mg, quant.) as a yellow solid. $^1$H-NMR (CDCl$_3$, Varian, 400 MHz): δ 1.58 (3H, d, J=6.8 Hz), 2.44 (4H, s), 2.49 (2H, s), 3.69-3.71 (4H, m), 5.10-5.17 (1H, m), 6.47 (1H, brs), 7.27 (2H, d, J=6.8 Hz), 7.34 (2H, d, J=7.6 Hz).

Step B: (R)-1-(4-((4-methylpiperazin-1-yl)methyl) phenyl)ethanamine

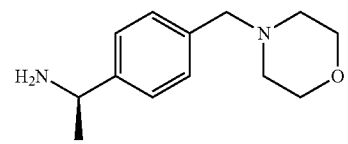 [SMILES: C[C@@H](N)c1ccc(CN2CCOCC2)cc1]

To a solution of (R)-2,2,2-trifluoro-N-(1-(4-(morpholinomethyl)phenyl)ethyl) acetamide (200 mg, 0.63 mmol) in EtOH (5 mL) was added 6 N aq. NaOH (527 μL, 3.16 mmol) at room temperature. The reaction mixture was stirred at room temperature for 3 hours, and then concentrated in vacuo. The residue was partitioned between water and EtOAc. The separated aqueous layer was extracted with EtOAc. The separated combined organic layers were washed with brine, dried over $Na_2SO_4$, filtered, and concentrated in vacuo to afford the (R)-1-(4-((4-methylpiperazin-1-yl) methyl)phenyl)ethanamine (124 mg, 89%) as a yellow oil, which was used for the next step without further purification. $^1$H-NMR (CDCl$_3$, Varian, 400 MHz): δ 1.39 (3H, d, J=6.8 Hz), 2.44 (4H, brs), 3.48 (2H, s), 3.71 (4H, t, J=4.4 Hz), 4.11 (1H, q, J=6.4 Hz), 7.26-7.31 (4H, m). *NH$_2$ peak was not observed.

Intermediate Example 3

Figure 3:
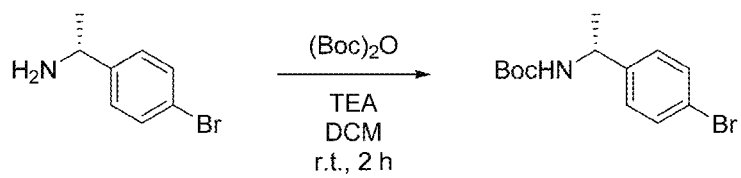
FIG. 3 is a chemical scheme depicting the synthesis of (R)-tert-butyl 1-(4-bromophenyl)ethylcarbamate (intermediate 3).

This example is directed to a synthesis of (R)-tert-butyl 1-(4-bromophenyl)ethylcarbamate (intermediate 3). See FIG. 3.

To a solution of (R)-1-(4-bromophenyl)ethanamine (10.0 g, 50.0 mmol) in DCM (167 mL) were added TEA (7.66 mL, 55.0 mmol) and (Boc)$_2$O (12.76 mL, 55.0 mmol) at room temperature. The reaction mixture was stirred at room temperature for 2 hours and quenched with water. The mixture was extracted with DCM, dried over $Na_2SO_4$, filtered, and concentrated in vacuo. The solid was recrystallized from DCM/Hexane to afford the (R)-tert-butyl 1-(4-bromophenyl)ethylcarbamate (12.8 g, 85%) as a white solid. $^1$H-NMR (DMSO-d$_6$, Varian, 400 MHz): δ 1.27 (3H, d, J=6.8 Hz), 1.36 (9H, s), 4.55-4.59 (1H, m), 7.24 (2H, d, J=8.4 Hz), 7.42 (1H, d, J=8.0 Hz), 7.50 (2H, d, J=8.0 Hz).

Intermediate Example 4

Figure 4:
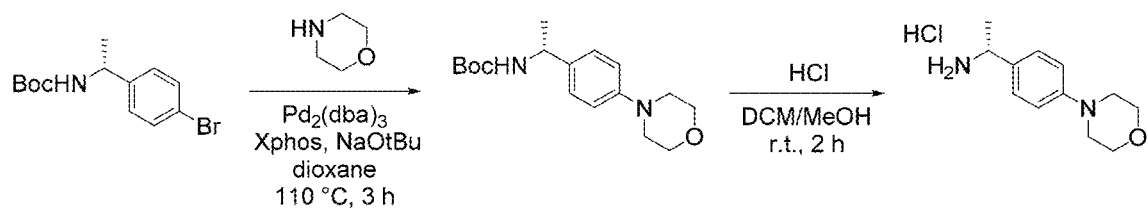
FIG. 4 is a chemical scheme depicting the synthesis of (R)-1-(4-morpholinophenyl)ethanamine hydrochloride (intermediate 4).

This example is directed to a synthesis of (R)-1-(4-morpholinophenyl)ethanamine hydrochloride (intermediate 4). See FIG. 4.

Step A: (R)-tert-butyl 1-(4-morpholinophenyl)ethylcarbamate

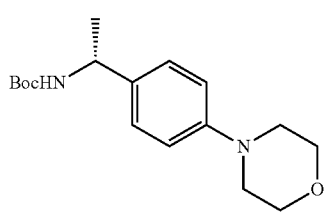

A mixture of (R)-tert-butyl 1-(4-bromophenyl)ethylcarbamate (intermediate 3, 8.00 g, 26.6 mmol), morpholine (3.02 mL, 34.6 mmol), XPhos (2-dicyclohexylphosphino-2',4',6'-triisopropylbiphenyl) (762 mg, 1.60 mmol) and NaO$^t$Bu (3.84 g, 40.0 mmol) in dioxane (89 mL) was degassed by purging and re-filled with argon in several times. After addition of Pd$_2$(dba)$_3$ (488 mg, 0.53 mmol), the reaction mixture was heated at 110° C. for overnight. After cooled to room temperature the reaction mixture was diluted with EtOAc and washed with water and brine. The separated organic layer was dried over $Na_2SO_4$, filtered, and concentrated in vacuo. The residue was purified by column chromatography on SiO$_2$ (Hexane:EtOAc=5:1 to 1:1) to afford the (R)-tert-butyl 1-(4-morpholinophenyl)ethylcarbamate (4.81 g, 58%) as a yellow solid. $^1$H-NMR (DMSO-d$_6$, Varian, 400 MHz): δ 1.25 (3H, d, J=7.2 Hz), 1.36 (9H, s), 3.05 (4H, t, J=4.8 Hz), 3.72 (4H, t, J=4.8 Hz), 4.51-4.54 (1H, m), 7.87 (2H, d, J=8.8 Hz), 7.14 (2H, d, J=8.8 Hz), 7.25 (1H, d, J=8.4 Hz).

Step B: (R)-1-(4-morpholinophenyl)ethanamine hydrochloride

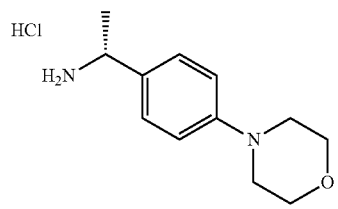

To a solution of (R)-tert-butyl 1-(4-morpholinophenyl) ethylcarbamate (4.81 g, 15.7 mmol) in DCM (39 mL) and MeOH (13 mL) was added HCl (4 M in dioxane, 39.2 mL, 157 mmol). After stirred at room temperature for 2 hours, the reaction mixture was concentrated in vacuo to afford the (R)-1-(4-morpholinophenyl)ethanamine hydrochloride (3.81 g, quant.) as a white solid, which was used for the next step without further purification. $^1$H-NMR (DMSO-d$_6$, Varian, 400 MHz): δ 1.49 (3H, d, J=7.2 Hz), 3.16-3.20 (4H, m), 3.80-3.81 (4H, m), 4.29-4.33 (1H, m), 7.16-7.18 (2H, m), 7.44 (2H, d, J=8.8 Hz), 8.48 (3H, m).

Intermediate Example 5

Figure 5:
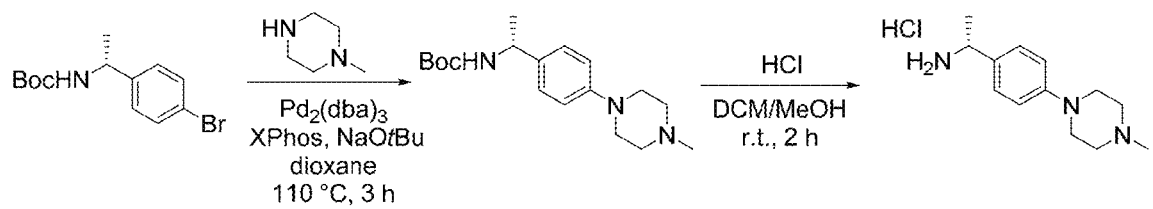
FIG. 5 is a chemical scheme depicting the synthesis of (R)-1-(4-(4-methylpiperazin-1-yl)phenyl)ethanamine hydrochloride (intermediate 5).

This example is directed to a synthesis of (R)-tert-butyl 1-(4-bromophenyl)ethylcarbamate (intermediate 5). See FIG. 5.

Step A: (R)-tert-butyl 1-(4-(4-methylpiperazin-1-yl) phenyl)ethylcarbamate

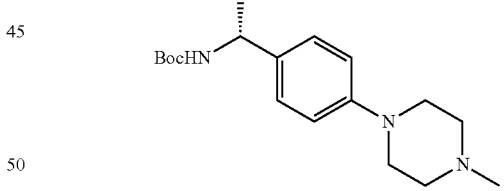

A mixture of (R)-tert-butyl 1-(4-bromophenyl)ethylcarbamate (intermediate 3, 300 mg, 0.999 mmol), 1-methypiperazine (300 mg, 3.00 mmol), XPhos (286 mg, 0.600 mmol) and NaOtBu (144 mg, 1.50 mmol) in dioxane (10 mL) was degassed by purging and re-filled with Ar in several times. After addition of Pd$_2$(dba)$_3$ (18.0 mg, 0.02 mmol), the reaction mixture was heated at 110° C. for 3 hours. After cooled to room temperature the reaction mixture was diluted with EtOAc and washed with water and brine. The separated organic layer was dried over $Na_2SO_4$, filtered, and concentrated in vacuo. The residue was purified by column chromatography on NH—SiO$_2$ (EtOAc:Hexane=5:1 to 3:1) to afford the (R)-tert-butyl 1-(4-(4-methylpiperazin-1-yl)phenyl)ethylcarbamate (270 mg, 85%) as a yellow solid. $^1$H-NMR (DMSO-d$_6$, Varian, 400 MHz): δ 1.25 (3H, d, J=7.2 Hz), 1.36 (9H, s), 2.21 (3H, s), 2.43 (4H, t, J=4.6 Hz), 3.08 (4H, t, J=4.8 Hz), 4.49-4.51 (1H, m), 6.86 (2H, d, J=8.4 Hz), 7.12 (2H, d, J=8.4 Hz), 7.23 (1H, d, J=8.0 Hz).

Step B: (R)-1-(4-(4-methylpiperazin-1-yl)phenyl)ethanamine hydrochloride

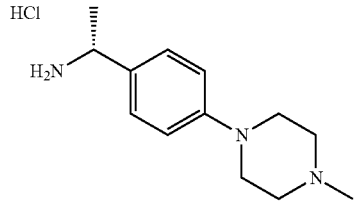 [SMILES: Cl ; C[C@@H](N)c1ccc(N2CCN(C)CC2)cc1]

To a solution of (R)-tert-butyl 1-(4-(4-methylpiperazin-1-yl)phenyl)ethylcarbamate (270 mg, 0.85 mmol) in DCM (6.0 mL) and MeOH (2.0 mL) was added HCl (4 M in dioxane, 2.11 mL, 8.45 mmol). After stirred at room temperature for 2 hours, the reaction mixture was concentrated in vacuo to afford the (R)-1-(4-(4-methylpiperazin-1-yl)phenyl)ethanamine hydrochloride (210 mg, quant.) as a white solid, which was used for the next step without further purification. $^1$H-NMR (DMSO-$d_6$, Varian, 400 MHz): δ 1.49 (3H, d, J=6.8 Hz), 2.78 (3H, d, J=4.8 Hz), 3.06-3.18 (4H, m), 3.45-3.47 (2H, m), 3.83-3.85 (2H, m), 4.27-4.29 (1H, m), 7.03 (2H, d, J=8.4 Hz), 7.42 (2H, d, J=8.8 Hz), 8.54 (3H, s).

Intermediate Example 6

Figure 6:
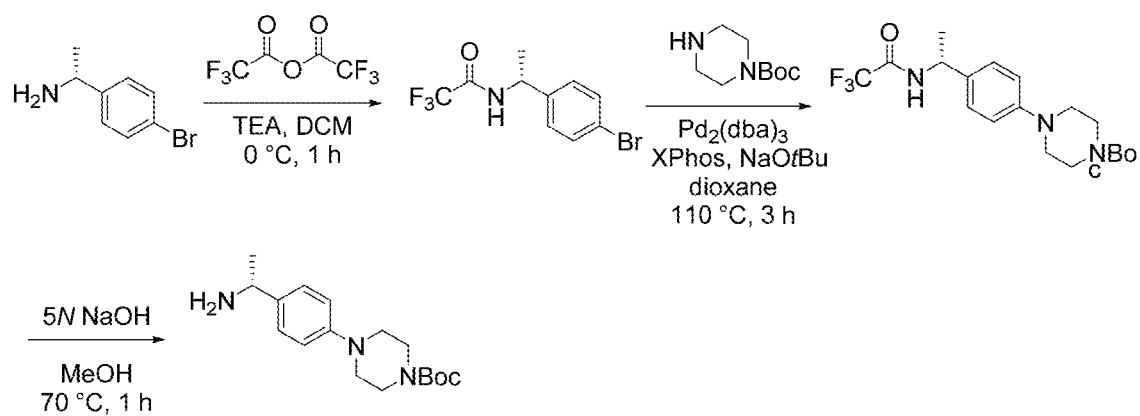
FIG. 6 is a chemical scheme depicting the synthesis of (R)-tert-butyl 4-(4-(1-aminoethyl)phenyl)piperazine-1-carboxylate (intermediate 6).

This example is directed to a synthesis of (R)-tert-butyl 4-(4-(1-aminoethyl)phenyl)piperazine-1-carboxylate (intermediate 6). See FIG. 6.

Step A: (R)—N-(1-(4-bromophenyl)ethyl)-2,2,2-trifluoroacetamide

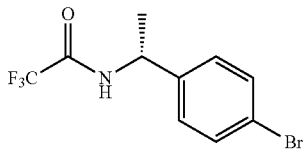 [SMILES: C[C@@H](NC(=O)C(F)(F)F)c1ccc(Br)cc1]

To a solution of (R)-1-(4-bromophenyl)ethanamine (500 mg, 2.11 mmol) in DCM (10 mL) was added trifluoroacetic anhydride (358 μL, 2.54 mmol) and TEA (648 μL, 4.65 mmol) at 0° C. After stirring at room temperature 1 hours, the reaction mixture was concentrated in vacuo. The solid was recrystallized from DCM/Hexane to afford the (R)—N-(1-(4-bromophenyl)ethyl)-2,2,2-trifluoroacetamide (568 mg, 91%) as a white solid. $^1$H-NMR (DMSO-$d_6$, Varian, 400 MHz): δ 1.44 (3H, d, J=7.2 Hz), 4.94-5.01 (1H, m), 7.30 (2H, d, J=8.4 Hz), 7.56 (2H, d, J=8.0 Hz), 9.89 (1H, d, J=8.0 Hz).

Step B: (R)-tert-butyl 4-(4-(1-(2,2,2-trifluoroacetamido)ethyl)phenyl)piperazine-1-carboxylate

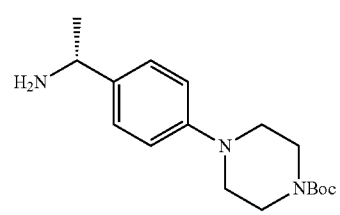 [SMILES: C[C@@H](N)c1ccc(N2CCN(C(=O)OC(C)(C)C)CC2)cc1]

A mixture of (R)—N-(1-(4-bromophenyl)ethyl)-2,2,2-trifluoroacetamide (568 mg, 1.92 mmol), tert-butyl piperazine-1-carboxylate (429 mg, 2.30 mmol), XPhos (274 mg, 0.576 mmol) and NaO$^t$Bu (277 mg, 2.88 mmol) in dioxane (19 mL) was degassed by purging and re-filled with argon in several times. After addition of Pd$_2$(dba)$_3$ (176 mg, 0.192 mmol), the reaction mixture was heated at 110° C. for 3 hours. After cooled to room temperature the reaction mixture was diluted with EtOAc and washed with water and brine. The separated organic layer was dried over Na$_2$SO$_4$, filtered, and concentrated in vacuo. The residue was purified by column chromatography on NH—SiO$_2$ (Hexane:EtOAc=1:1 to 1:3) to afford the (R)-tert-butyl 4-(4-(1-(2,2,2-trifluoroacetamido)ethyl)phenyl)piperazine-1-carboxylate (548 mg, 71%) as a yellow solid. $^1$H-NMR (DMSO-$d_6$, Varian, 400 MHz): δ 1.42 (12H, s), 3.06 (4H, t, J=5.0 Hz), 3.38-3.44 (4H, m), 4.90-4.96 (1H, m), 6.93 (2H, d, J=8.8 Hz), 7.19 (2H, d, J=9.2 Hz), 9.79 (1H, d, J=7.6 Hz).

Step C: (R)-tert-butyl 4-(4-(1-aminoethyl)phenyl)piperazine-1-carboxylate

To a solution of (R)-tert-butyl 4-(4-(1-(2,2,2-trifluoroacetamido)ethyl)phenyl)piperazine-1-carboxylate (400 mg, 0.10 mmol) in MeOH (3 mL) was added 5 N aq. NaOH (3.99 mL, 19.9 mmol) at room temperature. The reaction mixture was stirred at 70° C. for 1 hours. The reaction mixture was cooled to room temperature and then concentrated in vacuo. The residue was partitioned between water and EtOAc. The separated aqueous layer was extracted with EtOAc. The combined organic layers were washed with brine, dried over Na$_2$SO$_4$, filtered, and concentrated in vacuo to afford the (R)-tert-butyl 4-(4-(1-aminoethyl)phenyl)piperazine-1-carboxylate (272 mg, 89%) as a yellow oil, which was used for the next step without further purification. $^1$H-NMR (DMSO-$d_6$, Varian, 400 MHz): δ 1.19 (3H, d, J=6.8 Hz), 1.42 (9H, s), 1.74 (2H, s), 3.02 (4H, t, J=4.6 Hz), 3.43-3.44 (4H, m), 3.86-3.91 (1H, m), 6.88 (2H, d, J=8.4 Hz), 7.21 (2H, d, J=8.0 Hz).

Intermediate Example 7

Figure 7:
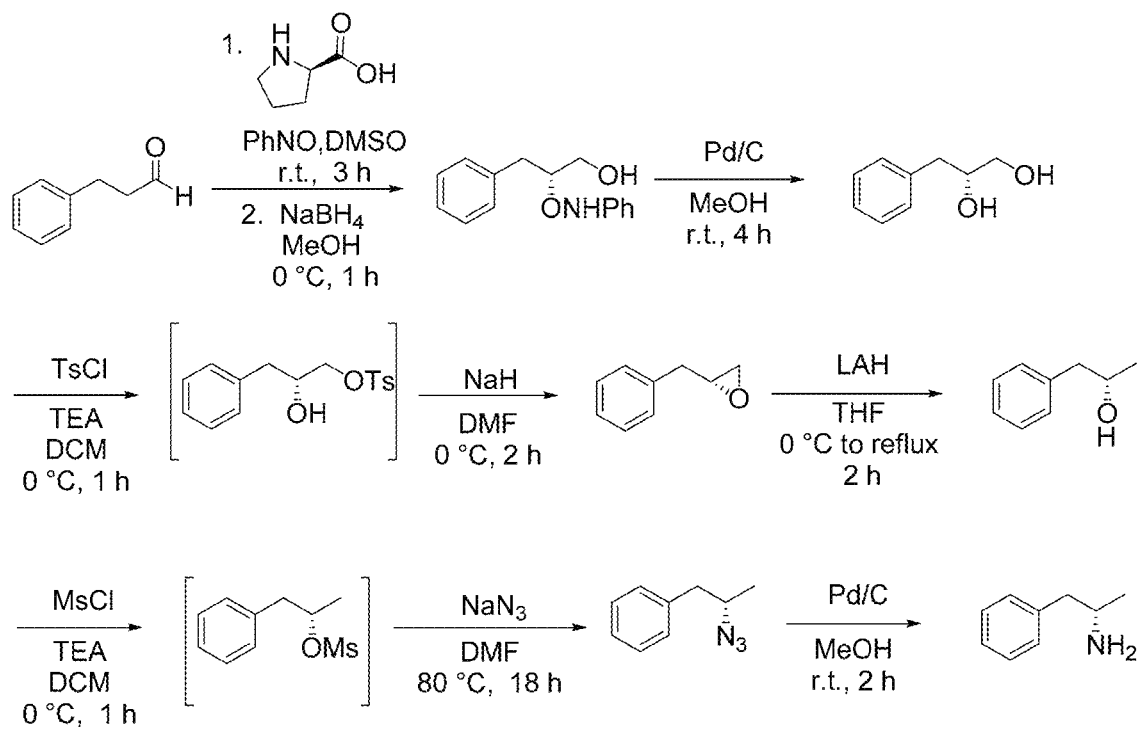
FIG. 7 is a chemical scheme depicting the synthesis of (R)-1-phenylpropan-2-amine (intermediate 7).

This example is directed to a synthesis of (R)-1-phenyl-propan-2-amine (intermediate 7). See FIG. 7.

Step A: (R)-3-phenyl-2-(phenylaminooxy)propan-1-ol

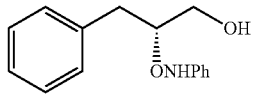

To a solution of 3-phenylpropanal (3.35 g, 25.0 mmol) in DMSO (20 mL) were added (S)-proline (575 mg, 4.99 mmol) and nitrosobenzene (2.27 g, 21.2 mmol). The reaction mixture was stirred at room temperature for 3 hours. The reaction mixture was lowered to 0° C., diluted with MeOH (8.0 mL). After addition of $NaBH_4$ (1.42 g, 37.5 mmol), the reaction mixture was stirred at 0° C. for 1 hours. The reaction mixture was partitioned between water and EtOAc and the aqueous layer was extracted with EtOAc. The combined organic layers were washed with water and brine, dried over $Na_2SO_4$, filtered, and concentrated in vacuo. The residue was purified by column chromatography on $SiO_2$ (Hexane:EtOAc=5:1) to afford the (R)-3-phenyl-2-(phenylaminooxy)propan-1-ol (1.26 g, 21%) as a yellow oil. $^1$H-NMR (CDCl$_3$, Varian, 400 MHz): δ 2.33 (1H, s), 2.86 (1H, dd, J=7.0, 13.8 Hz), 3.06 (1H, dd, J=6.8, 13.6 Hz), 3.75 (1H, dd, J=6.0, 12.0 Hz), 3.85-3.88 (1H, m), 4.11-4.17 (1H, m), 6.85 (2H, d, J=8.0 Hz), 6.96 (1H, t, J=6.8 Hz), 7.04 (1H, s), 7.17-7.33 (6H, m). *NH peak was not observed.

Step B: (R)-3-phenylpropane-1,2-diol

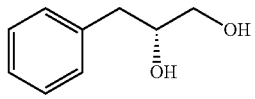 [SMILES: OC[C@H](O)Cc1ccccc1]

To a solution of (R)-3-phenyl-2-(phenylaminooxy)propan-1-ol (1.26 g, 5.22 mmol) in MeOH (17 mL) was added 10% Pd/C (56.0 mg, 0.052 mmol) at room temperature. The reaction mixture was stirred at room temperature for 4 hours under $H_2$ and concentrated in vacuo. The residue was purified by column chromatography on $SiO_2$ (Hexane:EtOAc=2:1) to afford the (R)-3-phenylpropane-1,2-diol (488 mg, 61%) as a yellow oil. $^1$H-NMR (CDCl$_3$, Varian, 400 MHz): δ 2.16-2.23 (2H, m), 2.72-2.82 (2H, m), 3.51 (1H, dd, J=7.0, 11.0 Hz), 3.68-3.70 (1H, m), 3.93-3.95 (1H, m), 7.21-7.23 (3H, m), 7.29-7.34 (2H, m).

Step C: (R)-2-benzyloxirane

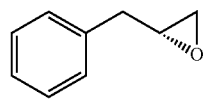

A mixture of (R)-3-phenylpropane-1,2-diol (488 mg, 3.21 mmol) and TEA (581 L, 4.17 mmol) in DCM (10 mL) was added TsCl (672 mg, 3.53 mmol) at 0° C. The reaction mixture was stirred at 0° C. for 1 hour. After quenched with ice water, the mixture was extracted with DCM, concentrated in vacuo to afford the crude (R)-2-hydroxy-3-phenylpropyl 4-methylbenzenesulfonate. A mixture of crude (R)-2-hydroxy-3-phenylpropyl 4-methylbenzenesulfonate (982 mg, 3.21 mmol) in dimethylformamide (DMF) (10 mL) was added NaH (55 wt % in oil, 280 mg, 6.41 mmol) at 0° C. The reaction mixture was stirred at 0° C. for 2 hours. After quenched with ice water, the mixture was extracted with EtOAc, concentrated in vacuo. The residue was purified by column chromatography on $SiO_2$ (Hexane:EtOAc=30:1) to afford the (R)-2-benzyloxirane (178 mg, 41%) as a yellow oil. $^1$H-NMR (CDCl$_3$, Varian, 400 MHz): δ 2.55-2.67 (1H, m), 2.79 (1H, t, J=4.4 Hz), 2.84 (1H, d, J=5.6 Hz), 2.93 (1H, dd, J=5.4, 14.6 Hz), 3.14-3.18 (1H, m), 7.23-7.26 (3H, m), 7.30-7.34 (2H, m).

Step D: (S)-1-phenylpropan-2-ol

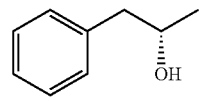

To a solution of (R)-2-benzyloxirane (178 mg, 5.93 mmol) in dry THF (13 mL) was added LAH (60 mg, 1.59 mmol) at 0° C. The reaction mixture was refluxed for 2 hours, and then quenched with $Na_2SO_4.10H_2O$ at 0° C. The reaction mixture was filtered through a Celite pad and washed with EtOAc. The filtrate was concentrated in vacuo to afford the (S)-1-phenylpropan-2-ol (165 mg, 91%) as a colorless oil which was used for the next step without further purification. $^1$H-NMR (CDCl$_3$, Varian, 400 MHz): δ 1.25 (3H, d, J=6.0 Hz), 1.53-1.59 (1H, m), 2.69 (1H, dd, J=8.0, 13.6 Hz), 2.79 (1H, dd, J=4.8, 13.6 Hz), 4.01-4.03 (1H, m), 7.21-7.24 (3H, m), 7.30-7.34 (2H, m).

Step E: (R)-(2-azidopropyl)benzene

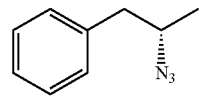

A mixture of (S)-1-phenylpropan-2-ol (165 mg, 1.21 mmol) and TEA (422 μL, 3.03 mmol) in DCM (12 mL) was added MsCl (142 μL, 1.81 mmol) at 0° C. The reaction mixture was stirred at 0° C. for 1 hour. After quenched with ice water, the mixture was extracted with DCM, concentrated in vacuo to afford crude (S)-1-phenylpropan-2-yl methanesulfonate. To a solution of (S)-1-phenylpropan-2-yl methanesulfonate in DMF (12 mL) was added $NaN_3$ at room temperature. The reaction mixture was stirred at 80° C. for 18 hour. The reaction mixture was cooled to room temperature. The reaction mixture was partitioned between water and EtOAc and the aqueous layer was extracted with EtOAc. The combined organic layers were washed with water and brine, dried over $Na_2SO_4$, filtered, and concentrated in vacuo. The residue was purified by column chromatography on $SiO_2$ (Hexane:EtOAc=3:1) to afford the (R)-(2-azidopropyl)benzene (139 mg, 71%) as a yellow oil. $^1$H-NMR (CDCl$_3$, Varian, 400 MHz): δ 1.25 (3H, d, J=6.8 Hz), 2.71

(1H, dd, J=6.8, 13.6 Hz), 2.82 (1H, dd, J=7.0, 13.6 Hz), 3.65-3.70 (1H, m), 7.18-7.24 (3H, m), 7.28-7.32 (2H, m).

Step F: (R)-1-phenylpropan-2-amine

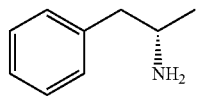

To a solution of (R)-(2-azidopropyl)benzene (139 mg, 0.86 mmol) in MeOH (10 mL) was added 10% Pd/C (10.0 mg, 8.62 µmol) at room temperature. The reaction mixture was stirred at room temperature for 2 hours under $H_2$ and concentrated in vacuo to afford the (R)-1-phenylpropan-2-amine (54.0 mg, 61%) as a yellow oil which was used for the next step without further purification. $^1$H-NMR (CDCl$_3$, Varian, 400 MHz): δ 1.10 (3H, d, J=6.0 Hz), 2.49 (1H, dd, J=13.0, 8.2 Hz), 2.69 (1H, dd, J=6.0, 13.2 Hz), 3.08-3.16 (1H, m), 7.16-7.21 (3H, m), 7.26-7.30 (2H, m). *NH$_2$ peak were not observed.

Intermediate Example 8

Figure 8:
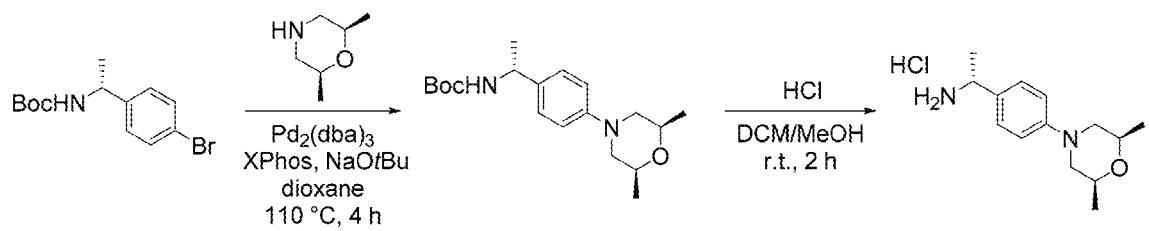
FIG. 8 is a chemical scheme depicting the synthesis of (R)-1-(4-((2S,6R)-2,6-dimethylmorpholino)phenyl)ethylamine hydrochloride (intermediate 8).

This example is directed to a synthesis of (R)-1-(4-((2S,6R)-2,6-dimethylmorpholino)phenyl)ehtylamine hydrochloride (intermediate 8). See FIG. 8.

Step A: tert-butyl (R)-1-(4-((2S,6R)-2,6-dimethylmorpholino)phenyl)ethylcarbamate

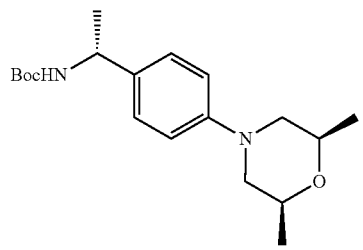 [SMILES: C[C@@H]1CN(c2ccc([C@@H](C)NC(=O)OC(C)(C)C)cc2)C[C@H](C)O1]

A mixture of (R)-tert-butyl 1-(4-bromophenyl)ethylcarbamate (intermediate 3, 300 mg, 1.00 mmol), (2S,6R)-2,6-dimethylmorpholine (0.37 mL, 3.00 mmol), XPhos (30.0 mg, 0.06 mmol) and NaO$^t$Bu (144 mg, 1.50 mmol) in dioxane (10 mL) was degassed by purging and re-filled with argon in several times. After addition of Pd$_2$(dba)$_3$ (18.0 mg, 0.02 mmol), the reaction mixture was heated at 110° C. overnight. After cooled to room temperature the reaction mixture was diluted with EtOAc and washed with water and brine. The separated organic layer was dried over Na$_2$SO$_4$, filtered, and concentrated in vacuo. The residue was purified by column chromatography on SiO$_2$ (Hexane:EtOAc=1:4) to afford the tert-butyl (R)-1-(4-((2S,6R)-2,6-dimethylmorpholino)phenyl)ethylcarbamate (280 mg, 84%) as a brown solid. $^1$H-NMR (CDCl$_3$, Varian, 400 MHz): δ 1.24 (9H, d, J=6.4 Hz), 1.29 (9H, s), 2.38 (2H, t, J=10.8 Hz), 3.41 (2H, d, J=11.2 Hz), 3.75-3.81 (2H, m), 4.73 (1H, s), 6.85 (2H, d, J=8.4 Hz), 7.19 (2H, d, J=8.4 Hz). *NH peak was not observed Step B: (R)-1-(4-((2S,6R)-2,6-dimethylmorpholino)phenyl)ehtylamine hydrochloride

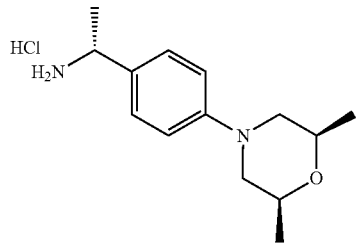 [SMILES: Cl ; C[C@@H]1CN(c2ccc([C@@H](C)N)cc2)C[C@H](C)O1]

To a solution of tert-butyl (R)-1-(4-((2S,6R)-2,6-dimethylmorpholino)phenyl)ethylcarbamate (140 mg, 0.42 mmol) in DCM (4 mL) was added HCl (4 M in dioxane, 1.05 mL, 4.20 mmol) at room temperature. After stirred for 2 hours at room temperature, the reaction mixture was concentrated in vacuo. The solid was triturated with ether to afford the (R)-1-(4-((2S,6R)-2,6-dimethylmorpholino)phenyl) ehtylamine hydrochloride (60.0 mg, 53%) as a white solid, which was used for the next step without further purification. $^1$H-NMR (CD$_3$OD, Varian, 400 MHz): δ 1.66 (6H, d, J=5.6 Hz), 1.50 (3H, d, J=5.6 Hz), 2.50 (1H, s), 2.50-2.59 (2H, m), 3.58 (2H, d, J=12.0 Hz), 3.93 (2H, s), 7.34 (2H, brs), 7.51 (2H, d, J=7.6 Hz), 8.58 (2H, s).

Intermediate Example 9

Figure 9:
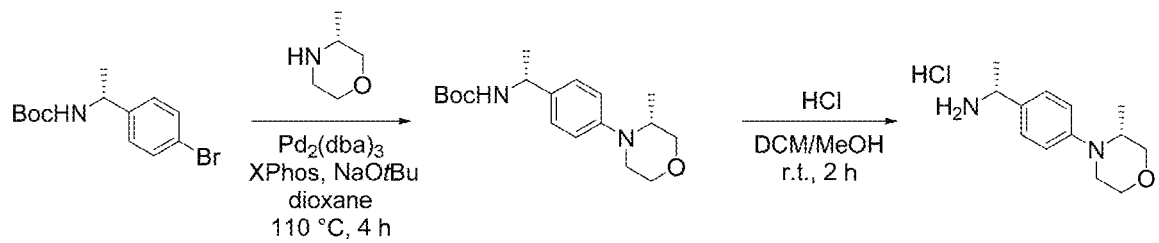
FIG. 9 is a chemical scheme depicting the synthesis of (R)-1-(4-((R)-3-methylmorpholino)phenyl)ethanamine hydrochloride (intermediate 9).

This example is directed to a synthesis of (R)-1-(4-((R)-3-methylmorpholino)phenyl)ethanamine hydrochloride (intermediate 9). See FIG. 9.

Step A: tert-butyl (R)-1-(4-((R)-3-methylmorpholino)phenyl)ethylcarbamate

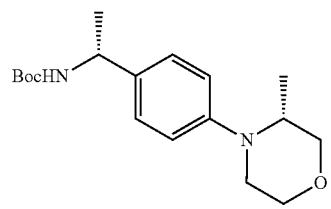 [SMILES: C[C@@H]1COCCN1c1ccc([C@@H](C)NC(=O)OC(C)(C)C)cc1]

A mixture of (R)-tert-butyl 1-(4-bromophenyl)ethylcarbamate (intermediate 3, 200 mg, 0.66 mmol), (R)-3-methylmorpholine (202 mg, 1.99 mmol), XPhos (19.0 mg, 0.04 mmol) and NaO$^t$Bu (96.0 mg, 0.99 mmol) in dioxane (10 mL) was degassed by purging and re-filled with argon in several times. After addition of Pd$_2$(dba)$_3$ (12.0 mg, 0.02 mmol), the reaction mixture was heated at 110° C. overnight. After cooled to room temperature the reaction mixture was diluted with EtOAc and washed with water and brine. The separated organic layer was dried over Na$_2$SO$_4$, filtered, and concentrated in vacuo. The residue was purified by column chromatography on SiO$_2$ (Hexane:EtOAc=1:4) to afford the tert-butyl (R)-1-(4-((R)-3-methylmorpholino)phenyl)ethylcarbamate (109 mg, 51%) as a colorless oil. $^1$H-NMR (CDCl$_3$, Varian, 400 MHz): δ 1.05 (3H, d, J=6.4 Hz), 1.42 (12H, s), 3.06-3.13 (2H, m), 3.68-3.74 (3H, m), 3.82-3.86 (1H, s), 3.93-3.98 (1H, m), 4.73 (1H, s), 6.85 (2H, d, J=8.8 Hz), 7.20 (2H, d, J=8.4 Hz). *NH peak was not observed Step B: (R)-1-(4-((R)-3-methylmorpholino)phenyl) ethanamine hydrochloride

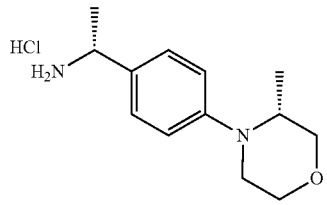 [SMILES: Cl ; C[C@@H]1COCCN1c1ccc([C@@H](C)N)cc1]

To a solution of tert-butyl (R)-1-(4-((R)-3-methylmorpholino)phenyl)ethylcarbamate (109 mg, 0.34 mmol) in DCM (3 mL) was added HCl (4 M in dioxane, 0.85 mL, 3.40 mmol) at room temperature. After stirred for 2 hours at room temperature, the reaction mixture was concentrated in vacuo. The solid was triturated with ether to afford the (R)-1-(4-((R)-3-methylmorpholino)phenyl)ethanamine hydrochloride (60.0 mg, 68%) as a white solid, which was used for the next step without further purification.

Intermediate Example 10

Figure 10:
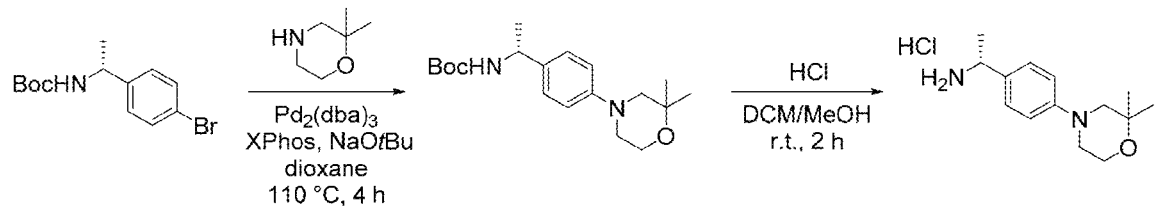
FIG. 10 is a chemical scheme depicting the synthesis of (R)-1-(4-(2,2-dimethylmorpholino)phenyl)ethanamine hydrochloride (intermediate 10).

This example is directed to a synthesis of (R)-1-(4-(2,2-dimethylmorpholino)phenyl)ethanamine hydrochloride (intermediate 10). See FIG. 10.

Step A: (R)-tert-butyl 1-(4-(2,2-dimethylmorpholino)phenyl)ethylcarbamate

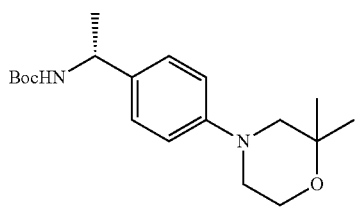 [SMILES: C[C@@H](NC(=O)OC(C)(C)C)c1ccc(N2CCOC(C)(C)C2)cc1]

A mixture of (R)-tert-butyl 1-(4-bromophenyl)ethylcarbamate (intermediate 3, 300 mg, 0.99 mmol), 2,2-dimethylmorpholine (345 mg, 3.00 mmol), XPhos (28.0 mg, 0.06 mmol) and NaO$^t$Bu (144 mg, 1.49 mmol) in dioxane (10 mL) was degassed by purging and re-filled with argon in several times. After addition of Pd$_2$(dba)$_3$ (18.0 mg, 0.02 mmol), the reaction mixture was heated at 110° C. overnight. After cooled to room temperature the reaction mixture was diluted with EtOAc and washed with water and brine. The separated organic layer was dried over Na$_2$SO$_4$, filtered, and concentrated in vacuo. The residue was purified by column chromatography on SiO$_2$ (Hexane:EtOAc=1:4) to afford (R)-tert-butyl 1-(4-(2,2-dimethylmorpholino)phenyl)ethylcarbamate (206 mg, 61%) as a colorless oil. $^1$H-NMR (CDCl$_3$, Varian, 400 MHz): δ 1.32 (6H, s), 1.42 (12H, s), 2.92 (2H, s), 3.07 (2H, t, J=4.0 Hz), 3.87 (2H, t, J=5.2 Hz), 4.72 (1H, s), 6.84 (2H, d, J=8.8 Hz), 7.20 (2H, d, J=8.8 Hz). *NH peak was not observed.

Step B: (R)-1-(4-(2,2-dimethylmorpholino)phenyl)ethanamine hydrochloride

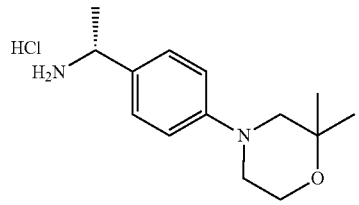 [SMILES: Cl ; C[C@@H](N)c1ccc(N2CCOC(C)(C)C2)cc1]

To a solution of (R)-tert-butyl 1-(4-(2,2-dimethylmorpholino)phenyl)ethylcarbamate (200 mg, 0.34 mmol) in DCM (3 mL) was added HCl (4 M in dioxane, 1.49 mL, 5.98 mmol) at room temperature. After stirred for 2 hours at room temperature, the reaction mixture was concentrated in vacuo. The solid was triturated with ether to afford the (R)-1-(4-(2,2-dimethylmorpholino)phenyl)ethanamine hydrochloride (106 mg, 65%) as a white solid, which was used for the next step without further purification. $^1$H-NMR (DMSO-d$_6$, Varian, 400 MHz): δ 1.22 (6H, s), 1.47 (3H, d, J=6.8 Hz), 2.96 (2H, s), 3.07 (2H, t, J=4.8 Hz), 3.75 (2H, t, J=5.2 Hz), 4.25-4.28 (1H, m), 6.97 (2H, d, J=8.8 Hz), 7.35 (2H, d, J=8.4 Hz), 8.39 (2H, s).

Intermediate Example 11

Figure 11:
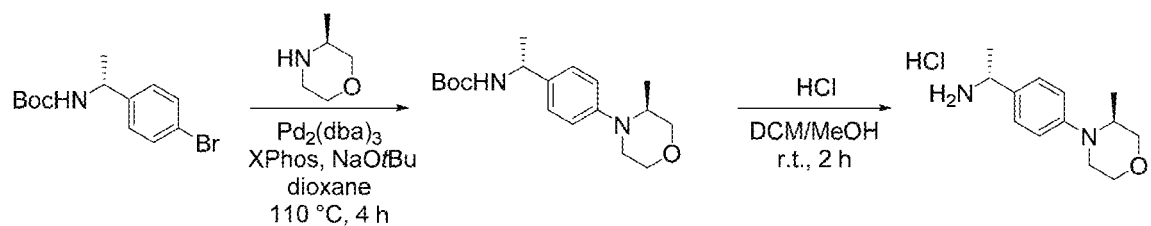
FIG. 11 is a chemical scheme depicting the synthesis of (R)-1-(4-((S)-3-methylmorpholino)phenyl)ethanamine hydrochloride (intermediate 11).

This example is directed to a synthesis of (R)-1-(4-((S)-3-methylmorpholino)phenyl)ethanamine hydrochloride (intermediate 11). See FIG. 11.

Step A: tert-butyl (R)-1-(4-(S)-3-methylmorpholino)phenyl)ethylcarbamate

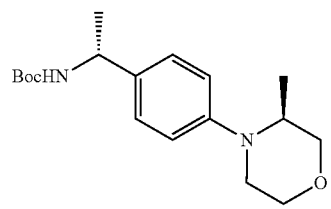 [SMILES: C[C@@H](NC(=O)OC(C)(C)C)c1ccc(N2CCOC[C@@H]2C)cc1]

A mixture of (R)-tert-butyl 1-(4-bromophenyl)ethylcarbamate (intermediate 3, 300 mg, 0.99 mmol), (S)-3-methylmorpholine (303 mg, 3.00 mmol), XPhos (28.0 mg, 0.06 mmol) and NaO$^t$Bu (144 mg, 1.49 mmol) in dioxane (10 mL) was degassed by purging and re-filled with argon in several times. After addition of Pd$_2$(dba)$_3$ (18.0 mg, 0.02 mmol), the reaction mixture was heated at 110° C. overnight. After cooled to room temperature the reaction mixture was diluted with EtOAc and washed with water and brine. The separated organic layer was dried over Na$_2$SO$_4$, filtered, and concentrated in vacuo. The residue was purified by column chromatography on SiO$_2$ (Hexane:EtOAc=1:4) to afford tert-butyl (R)-1-(4-(S)-3-methylmorpholino)phenyl) ethylcarbamate (215 mg, 67%) as a colorless oil. $^1$H-NMR (CDCl$_3$, Varian, 400 MHz): δ 1.32 (3H, s), 1.42 (12H, s), 3.00-3.11 (2H, m), 3.62-3.81 (3H, m), 3.77-3.81 (1H, m), 3.88-3.92 (1H, m), 4.69 (1H, s), 4.87 (1H, s), 6.80 (2H, d, J=8.4 Hz), 7.16 (2H, d, J=8.4 Hz).

Step B: (R)-1-(4-((S)-3-methylmorpholino)phenyl) ethanamine hydrochloride

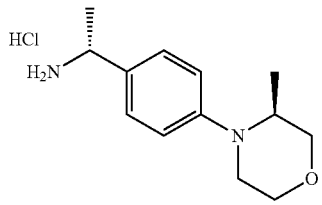

To a solution of tert-butyl (R)-1-(4-(S)-3-methylmorpholino)phenyl)ethylcarbamate (109 mg, 0.34 mmol) in DCM (3 mL) was added HCl (4 M in dioxane, 0.85 mL, 3.40 mmol) at room temperature. After stirred for 2 hours at room temperature, the reaction mixture was concentrated in vacuo. The solid was triturated with ether to afford the (R)-1-(4-((S)-3-methylmorpholino)phenyl)ethanamine hydrochloride (60.0 mg, 68%) as a white solid, which was used for the next step without further purification.

Intermediate Example 12

Figure 12:
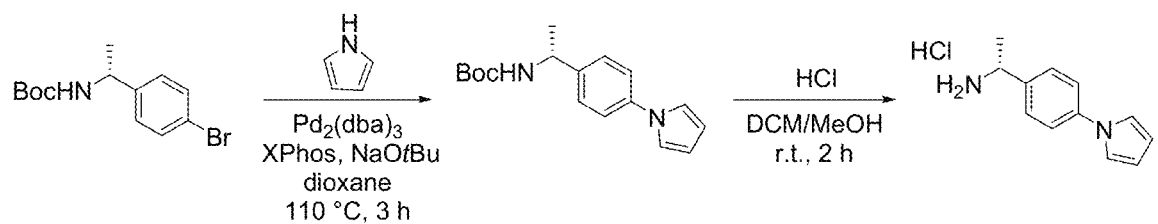
FIG. 12 is a chemical scheme depicting the synthesis of (R)-1-(4-(1H-pyrrol-1-yl)phenyl)ethanamine hydrochloride (intermediate 12).

This example is directed to a synthesis of (R)-1-(4-(1H-pyrrol-1-yl)phenyl)ethanamine hydrochloride (intermediate 12). See FIG. 12.

Step A: (R)-tert-butyl 1-(4-(1H-pyrrol-1-yl)phenyl) ethylcarbamate

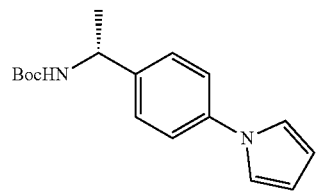 [SMILES: C[C@@H](NC(=O)OC(C)(C)C)c1ccc(-n2cccc2)cc1]

A mixture of (R)-tert-butyl 1-(4-bromophenyl)ethylcarbamate (intermediate 3, 200 mg, 0.67 mmol), 1H-pyrrole (60.0 µL, 0.87 mmol), XPhos (19.0 mg, 0.04 mmol) and NaO$^t$Bu (96.0 mg, 1.00 mmol) in dioxane (5 mL) was degassed by purging and re-filled with N$_2$ gas in several times. After addition of Pd$_2$(dba)$_3$ (12.0 mg, 0.01 mmol), the reaction mixture was stirred at 110° C. for 3 hours. After cooled to room temperature the reaction mixture was diluted with EtOAc and washed with water and brine. The separated organic layer was dried over Na$_2$SO$_4$, filtered, and concentrated in vacuo. The residue was purified by column chromatography on SiO$_2$ (Hexane:EtOAc=10:1 to 2:1) to afford the (R)-tert-butyl 1-(4-(1H-pyrrol-1-yl)phenyl)ethylcarbamate (97.0 mg, 50%) as a yellow solid. $^1$H-NMR (400 MHz, CDCl$_3$): δ 1.43-1.55 (12H, m), 4.80 (1H, brs), 6.34-6.35 (2H, m), 7.06-7.08 (2H, m), 7.35 (5H, s).

Step B: (R)-1-(4-(1H-pyrrol-1-yl)phenyl)ethanamine hydrochloride

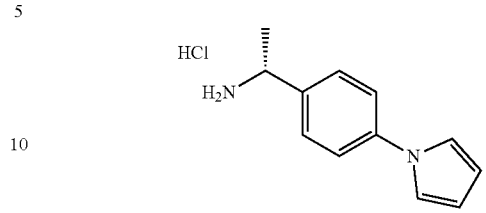

To a solution of (R)-tert-butyl 1-(4-(1H-pyrrol-1-yl)phenyl)ethylcarbamate (97.0 mg, 0.34 mmol) in DCM (3 mL) and MeOH (40 µL) was added HCl (2 M solution in ether, 3.4 mL, 6.80 mmol). After stirred at room temperature for 2 hours, the reaction mixture was concentrated in vacuo to afford the (R)-1-(4-(1H-pyrrol-1-yl)phenyl)ethanamine hydrochloride (95.0 mg, 126%) as a brown solid, which was used for the next step without further purification. $^1$H-NMR (400 MHz, DMSOd$_6$): δ 1.52 (3H, d, J=6.8 Hz), 4.44 (1H, brs), 6.28 (2H, s), 7.38 (2H, s), 7.57 (2H, d, J=8.4 Hz), 7.66 (2H, d, J=8.4 Hz), 8.41 (3H, brs).

Intermediate Example 13

Figure 13:
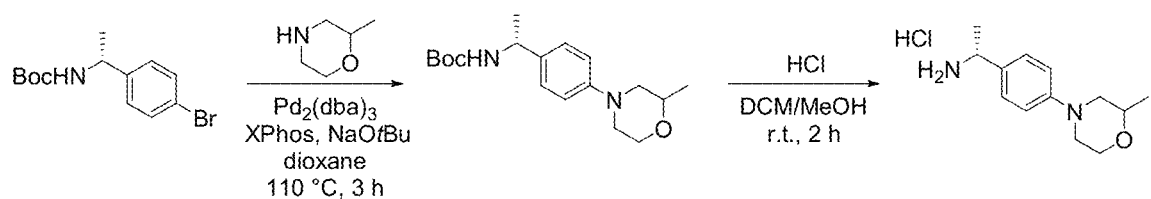
FIG. 13 is a chemical scheme depicting the synthesis of (R)-1-(4-(2-methylmorpholino)phenyl)ethanamine hydrochloride (intermediate 13).

This example is directed to a synthesis of (R)-1-(4-(2-methylmorpholino)phenyl)ethanamine hydrochloride (intermediate 13). See FIG. 13.

Step A: tert-butyl (R)-1-(4-(2-methylmorpholino) phenyl)ethylcarbamate

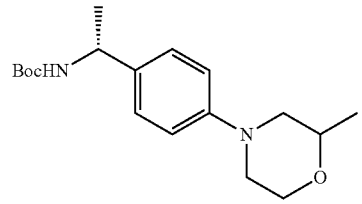 [SMILES: CC1CN(c2ccc([C@@H](C)NC(=O)OC(C)(C)C)cc2)CCO1]

A mixture of (R)-tert-butyl 1-(4-bromophenyl)ethylcarbamate (intermediate 3, 200 mg, 0.67 mmol), 2-methylmorpholine (88.0 mg, 0.87 mmol), Xphos (19.0 mg, 0.040 mmol), and NaO$^t$Bu (96.0 mg, 1.00 mmol) in dioxane (5 mL) was degassed by purging and re-filled with N$_2$ gas in several times. After addition of Pd$_2$(dba)$_3$ (12.0 mg, 0.013 mmol), the reaction mixture was stirred at 110° C. for 3 hours. After cooled to room temperature the reaction mixture was diluted with EtOAc and washed with water and brine. The separated organic layer was dried over Na$_2$SO$_4$, filtered, and concentrated in vacuo. The residue was purified by column chromatography on SiO$_2$ (Hexane:EtOAc=5:1 to 2:1) to afford the tert-butyl (R)-1-(4-(2-methylmorpholino)phenyl)ethylcarbamate (158 mg, 74%) as a yellow solid. $^1$H-NMR (400 MHz, CDCl$_3$): δ 1.25 (3H, d, J=6.0 Hz), 1.42 (12H, s), 2.47 (1H, t, J=8.0 Hz), 2.81 (1H, td, J=11.9 Hz), 3.37-3.46 (2H, m), 3.74-3.82 (2H, m), 3.99-4.02 (1H, m), 4.73 (2H, brs), 6.88 (2H, d, J=8.4 Hz), 7.22 (2H, d, J=8.0 Hz).

Step B: (R)-1-(4-(2-methylmorpholino)phenyl)ethanamine hydrochloride

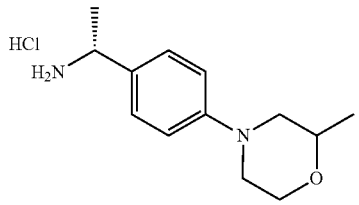 [SMILES: Cl ; CC1CN(c2ccc([C@@H](C)N)cc2)CCO1]

To a solution of tert-butyl (R)-1-(4-(2-methylmorpholino)phenyl)ethylcarbamate (158 mg, 0.49 mmol) in DCM (3 mL) and MeOH (40 μL) was added HCl (2 M solution in ether, 2.46 mL, 4.93 mmol). After stirred at room temperature for 2 hours, the reaction mixture was concentrated in vacuo to afford the (1R)-1-(4-(2-methylmorpholino)phenyl)ethanamine hydrochloride (127 mg, 100%) as a white solid, which was used for the next step without further purification.

Intermediate Example 14

Figure 14:
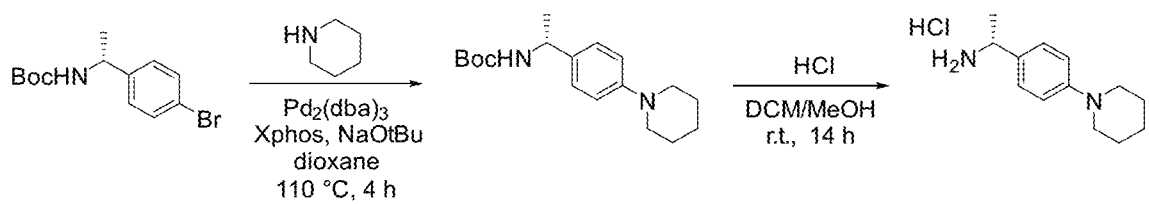
FIG. 14 is a chemical scheme depicting the synthesis of (R)-1-(4-(piperidin-1-yl)phenyl)ethanamine hydrochloride (intermediate 14).

This example is directed to a synthesis of (R)-1-(4-(piperidin-1-yl)phenyl)ethanamine hydrochloride (intermediate 14). See FIG. 14.

Step A: (R)-tert-butyl 1-(4-(piperidin-1-yl)phenyl)ethylcarbamate

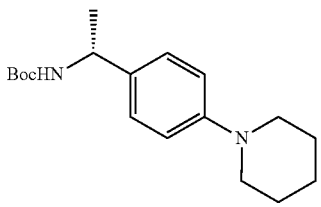 [SMILES: C[C@@H](NC(=O)OC(C)(C)C)c1ccc(N2CCCCC2)cc1]

A mixture of (R)-tert-butyl 1-(4-bromophenyl)ethylcarbamate (intermediate 3, 200 mg, 0.67 mmol), Pd$_2$(dba)$_3$ (12.0 mg, 0.013 mmol), XPhos (19.0 mg, 0.040 mmol), piperidine (197 μL, 2.00 mmol) and NaO$^t$Bu (96.0 mg, 1.00 mmol) in Dioxane (6.6 mL) was stirred for 4 hours at 110° C. After being cooled at room temperature, the reaction mixture was diluted with EtOAc and washed with water and brine. The separated organic layer was dried over Na$_2$SO$_4$, filtered, and concentrated in vacuo. The residue was purified by column chromatography on SiO$_2$ (Hexane:EtOAc=4:1) to afford the (R)-tert-butyl 1-(4-(piperidin-1-yl)phenyl)ethylcarbamate (170 mg, 84%) as a yellow solid. $^1$H-NMR (400 MHz, DMSO-d$_6$): δ 1.25 (3H, d, J=7.2 Hz), 1.36 (9H, s), 1.51-1.53 (2H, m), 1.57-1.63 (4H, m), 3.07 (4H, t, J=5.2 Hz), 4.49-4.52 (1H, m), 6.84 (2H, d, J=9.2 Hz), 7.11 (2H, d, J=8.8 Hz), 7.24 (1H, d, J=8.4 Hz).

Step B: (R)-1-(4-(piperidin-1-yl)phenyl)ethanamine hydrochloride

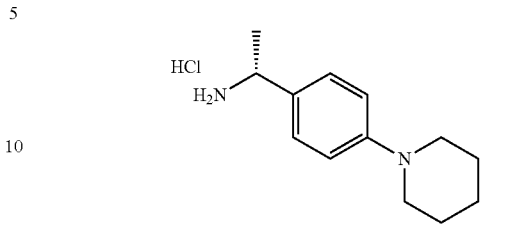

To a solution of (R)-tert-butyl 1-(4-(piperidin-1-yl)phenyl)ethylcarbamate (170 mg, 0.56 mmol) in DCM (4 mL) and MeOH (1.4 mL) was added HCl (4M in dioxane, 1.34 mL, 5.58 mmol) at 0° C. After stirred for 2 hours at room temperature, the reaction mixture was concentrated in vacuo to afford the (R)-1-(4-(piperidin-1-yl)phenyl)ethanamine hydrochloride (120 mg, quant.) as a white solid, which was used for the next step without further purification. $^1$H-NMR (400 MHz, DMSO-d$_6$): δ 1.47 (3H, d, J=6.4 Hz), 1.59 (2H, brs), 1.71 (4H, brs), 3.29 (4H, brs), 4.34 (1H, brs), 7.10-7.50 (3H, m), 8.21 (2H, brs). *2H from NH$_2$ was not observed.

Example 1

This example is directed to a synthesis of (R)-7-fluoro-N-(1-phenylethyl)-1H-indole-2-carboxamide.

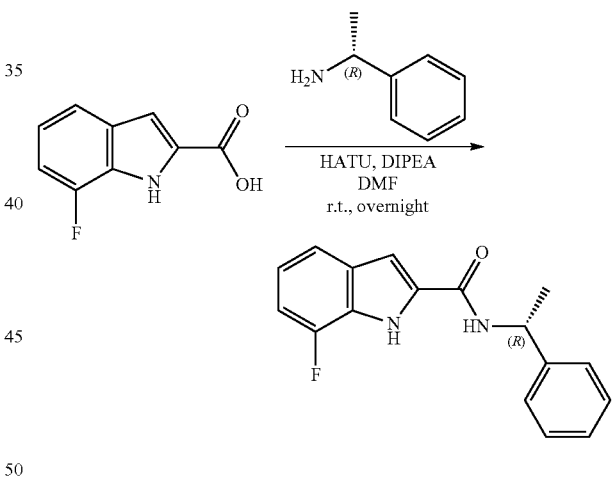

The mixture of 4-fluoro-1H-indole-2-carboxylic acid (100 mg, 0.56 mmol), (R)-1-phenylethanamine (71.0 μL, 0.56 mmol), HATU (1-[bis(dimethylamino)methylene]-1H-1,2,3-triazolo[4,5-b]pyridinium 3-oxide hexafluorophosphate, N-[(dimethylamino)-1H-1,2,3-triazolo-[4,5-b]pyridin-1-yl-methylene]-N-methylmethanaminium hexafluorophosphate N-oxide) (233 mg, 0.61 mmol), and DIPEA (N,N-diisopropylethylamine) (244 μL, 1.39 mmol) in DMF (3.0 mL) was stirred overnight at room temperature. The reaction mixture was partitioned between water and EtOAc and the aqueous layer was extracted with EtOAc. The combined organic layers were washed with water and brine, dried over Na$_2$SO$_4$, filtered, and concentrated in vacuo. The residue was purified by column chromatography on SiO$_2$ (Hexane: EtOAc=2:1) to afford the (R)-7-fluoro-N-(1-phenylethyl)-1H-indole-2-carboxamide, a reference compound, (46.7 mg, 30%) as a yellow solid. $^1$H-NMR (CDCl$_3$, Varian, 400

MHz): δ 1.64 (3H, d, J=6.8 Hz), 5.31-5.41 (1H, m), 6.35 (1H, brs), 6.88 (1H, s), 6.95-7.07 (2H, m), 7.27-7.32 (1H, m), 7.36-7.42 (5H, m), 9.44 (1H, brs).

Example 2

This example is directed to a synthesis of N-benzylimidazo[1,2-a]pyridine-2-carboxamide.

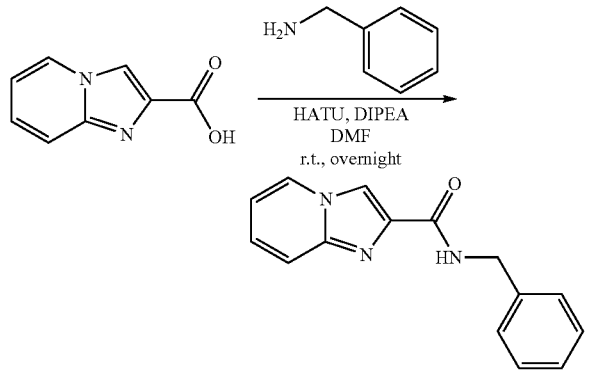

The mixture of imidazo[1,2-a]pyridine-2-carboxylic acid (100 mg, 0.62 mmol), HATU (258 mg, 0.68 mmol), and DIPEA (269 μL, 1.54 mmol) in DMF (3.0 mL) was stirred at room temperature for 1 hours. After phenylmethanamine (67.0 μL, 0.62 mmol) was added, the reaction mixture was stirred at room temperature for overnight. The reaction mixture was partitioned between water and EtOAc. The aqueous layer was extracted with EtOAc and the combined organic layers were washed with water and brine, dried over $Na_2SO_4$, filtered, and concentrated in vacuo. The residue was purified by column chromatography on $SiO_2$ (Hexane: EtOAc=1:4) to afford the N-benzylimidazo[1,2-a]pyridine-2-carboxamide (100 mg, 64%) as a yellow solid. $^1$H-NMR ($CDCl_3$, Varian, 400 MHz): δ 4.67 (2H, d, J=6.4 Hz), 6.85 (1H, t, J=6.8 Hz), 7.22-7.29 (2H, m), 7.33-7.55 (4H, m), 7.53 (1H, d, J=9.2 Hz), 7.70 (1H, brs), 8.15 (1H, d, J=7.2 Hz), 8.17 (1H, s). MS: 252.1 [MH$^+$].

Example 3

This example is directed to a synthesis of N-(2-phenylpropan-2-yl)imidazo[1,2-a]pyridine-2-carboxamide.

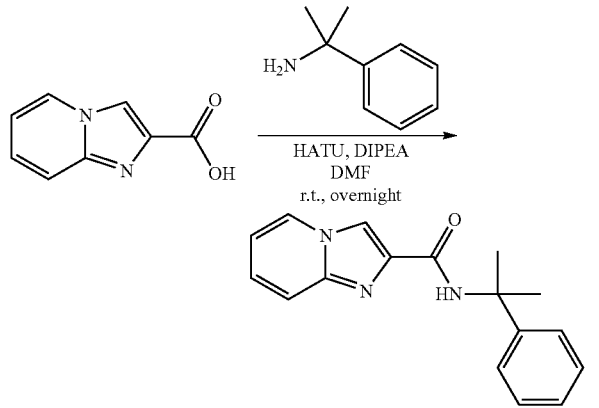

The mixture of imidazo[1,2-a]pyridine-2-carboxylic acid (100 mg, 0.62 mmol), HATU (258 mg, 0.68 mmol), and DIPEA (269 μL, 1.54 mmol) in DMF (3.0 mL) was stirred at room temperature for 1 hours. After 2-phenylpropan-2-amine (133 μL, 0.93 mmol) was added, the reaction mixture was stirred at room temperature for overnight. The reaction mixture was partitioned between water and EtOAc and the aqueous layer was extracted with EtOAc. The combined organic layers were washed with water and brine, dried over $Na_2SO_4$, filtered, and concentrated in vacuo. The residue was purified by column chromatography on $SiO_2$ (Hexane: EtOAc=1:4) to afford the N-(2-phenylpropan-2-yl)imidazo[1,2-a]pyridine-2-carboxamide (115 mg, 67%) as a yellow solid. $^1$H-NMR ($CDCl_3$, Varian, 400 MHz): δ 1.85 (6H, s), 6.84 (1H, t, J=6.8 Hz), 6.84 (1H, t, J=6.8 Hz), 7.21-7.26 (2H, m), 7.33 (2H, t, J=7.6 Hz), 7.49 (2H, d, J=8.4 Hz), 7.58 (1H, d, J=9.2 Hz), 8.06 (1H, s), 8.12 (1H, d, J=7.2 Hz). MS: 279.9 [MH$^+$].

Example 4

This example is directed to a synthesis of (S)—N-(1-phenylethyl)imidazo[1,2-a]pyridine-2-carboxamide.

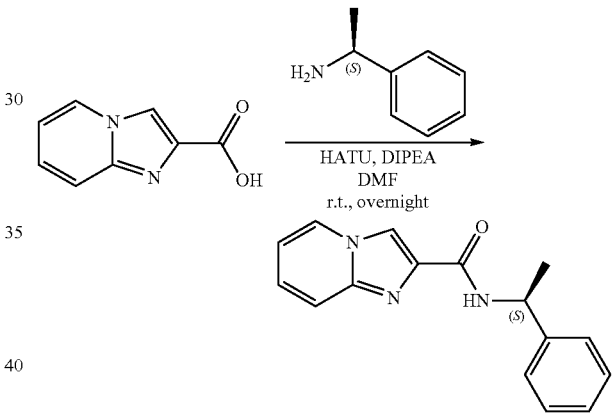

The mixture of imidazo[1,2-a]pyridine-2-carboxylic acid (100 mg, 0.62 mmol), HATU (258 mg, 0.68 mmol), and DIPEA (269 μL, 1.54 mmol) in DMF (3.0 mL) was stirred at room temperature for 1 hours. After (S)-1-phenylethanamine (79.0 μL, 0.62 mmol) was added, the reaction mixture was stirred at room temperature for overnight. The reaction mixture was partitioned between water and EtOAc and the aqueous layer was extracted with EtOAc. The combined organic layers were washed with water and brine, dried over $Na_2SO_4$, filtered, and concentrated in vacuo. The residue was purified by column chromatography on $SiO_2$ (Hexane:EtOAc=1:4) to afford the (S)—N-(1-phenylethyl)imidazo[1,2-a]pyridine-2-carboxamide (120 mg, 73%) as a yellow solid. $^1$H-NMR ($CDCl_3$, Varian, 400 MHz): δ 1.63 (3H, d, J=6.8 Hz), 5.31-5.39 (1H, m), 6.84 (1H, t, J=6.8 Hz), 7.22-7.27 (2H, m), 7.34 (2H, t, J=7.6 Hz), 7.42 (2H, d, J=7.6 Hz), 7.56 (1H, d, J=9.2 Hz), 7.62 (1H, d, J=6.8 Hz), 8.13-8.15 (2H, m). MS: 266.0 [MH$^+$].

Example 5

This example is directed to a synthesis of (R)—N-(1-phenylethyl)imidazo[1,2-a]pyridine-2-carboxamide.

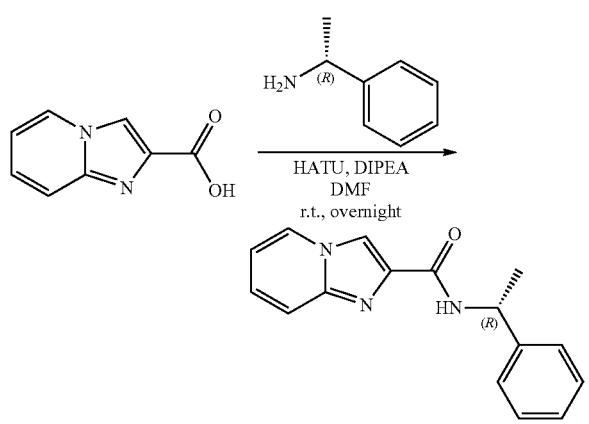

The mixture of imidazo[1,2-a]pyridine-2-carboxylic acid (100 mg, 0.62 mmol), (R)-1-phenylethanamine (79.0 μL, 0.62 mmol), HATU (258 mg, 0.68 mmol), and DIPEA (269 μL, 1.54 mmol) in DMF (3.0 mL) was stirred at room temperature for overnight. The reaction mixture was partitioned between water and EtOAc and the aqueous layer was extracted with EtOAc. The combined organic layers were washed with water and brine, dried over $Na_2SO_4$, filtered, and concentrated in vacuo. The residue was purified by column chromatography on $SiO_2$ (Hexane:EtOAc=1:4) to afford the (R)—N-(1-phenylethyl)imidazo[1,2-a]pyridine-2-carboxamide (57.8 mg, 35%) as a yellow solid. $^1$H-NMR (CDCl$_3$, Varian, 400 MHz): δ 1.66 (3H, d, J=7.2 Hz), 5.28-5.35 (1H, m), 7.01 (1H, t, J=7.2 Hz), 7.22-7.26 (1H, m), 7.33 (2H, d, J=7.2 Hz), 7.42-7.46 (3H, m), 7.68 (1H, d, J=9.2 Hz), 8.20 (1H, d, J=7.2 Hz), 8.27 (1H, s), 8.40 (1H, brs). MS: 266.0 [MH$^+$].

Example 6

This example is directed to a synthesis of (R)—N-(1-(4-((4-methylpiperazin-1-yl)methyl)phenyl)ethyl)imidazo[1,2-a]pyridine-2-carboxamide.

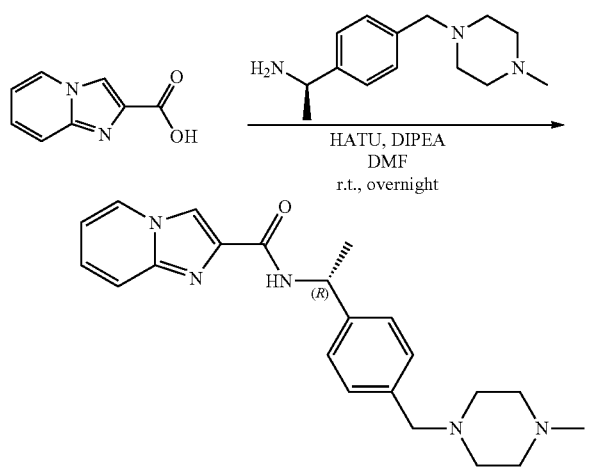

The mixture of imidazo[1,2-a]pyridine-2-carboxylic acid (47.0 mg, 0.29 mmol), HATU (120 mg, 0.32 mmol), and DIPEA (125 μL, 0.72 mmol) in DMF (3.0 mL) was stirred at room temperature for 1 hours. (R)-1-(4-((4-methylpiperazin-1-yl)methyl)phenyl)ethanamine (intermediate 1, 67.0 mg, 0.29 mmol) was added to the reaction mixture and stirred at room temperature for overnight. The reaction mixture was partitioned between water and EtOAc and the separated aqueous layer was extracted with EtOAc. The combined organic layers were washed with water and brine, dried over $Na_2SO_4$, filtered, and concentrated in vacuo. The residue was purified by column chromatography on NH—SiO$_2$ (Hexane:EtOAc=98:2) to afford the (R)—N-(1-(4-((4-methylpiperazin-1-yl)methyl)phenyl)ethyl)imidazo[1,2-a]pyridine-2-carboxamide (62.0 mg, 57%) as a yellow oil. $^1$H-NMR (CDCl$_3$, Varian, 400 MHz): δ 1.62 (3H, d, J=7.2 Hz), 2.27 (3H, s), 2.44 (8H, brs), 3.48 (2H, s), 5.31-5.38 (1H, m), 6.83 (1H, t, J=6.8 Hz), 7.23 (1H, t, J=8.0 Hz), 7.28 (2H, d, J=8.0 Hz), 7.37 (2H, d, J=8.0 Hz), 7.55 (1H, d, J=9.2 Hz), 7.64 (1H, d, J=8.4 Hz), 8.13 (1H, d, J=6.8 Hz), 8.15 (1H, s). MS: 378.1 [MH$^+$].

Example 7

This example is directed to a synthesis of (R)—N-(1-(4-((4-methylpiperazin-1-yl)methyl)phenyl)ethyl)imidazo[1,2-a]pyridine-2-carboxamide.

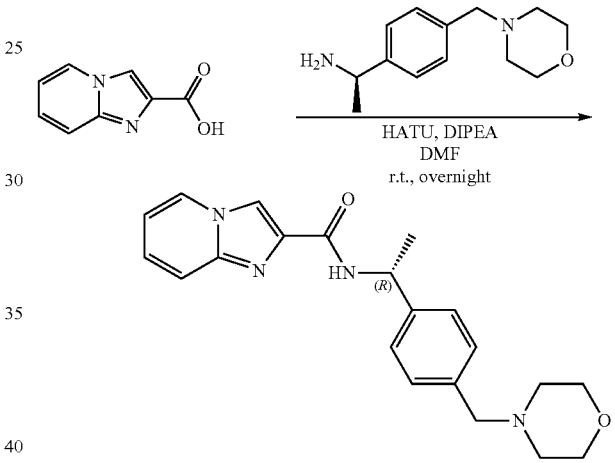

The mixture of imidazo[1,2-a]pyridine-2-carboxylic acid (91.0 mg, 0.56 mmol), HATU (235 mg, 0.62 mmol), and DIPEA (246 μL, 1.41 mmol) in DMF (3.0 mL) was stirred at room temperature for 1 hours. (R)-1-(4-((4-methylpiperazin-1-yl)methyl)phenyl)ethanamine (intermediate 2, 124 mg, 0.563 mmol) was added to the reaction mixture, which was stirred overnight at room temperature. The reaction mixture was partitioned between water and EtOAc and the separated the aqueous layer was extracted with EtOAc. The combined organic layers were washed with water and brine, dried over $Na_2SO_4$, filtered, and concentrated in vacuo. The residue was purified by column chromatography on NH—SiO$_2$ (Hexane:EtOAc=98:2) to afford the (R)—N-(1-(4-((4-methylpiperazin-1-yl)methyl)phenyl)ethyl)imidazo[1,2-a]pyridine-2-carboxamide (154 mg, 75%) as a yellow solid. $^1$H-NMR (CDCl$_3$, Varian, 400 MHz): δ 1.62 (3H, d, J=6.8 Hz), 2.43 (4H, brs), 3.47 (2H, s), 3.70 (4H, t, J=4.4 Hz), 3.50-5.38 (1H, m), 6.85 (1H, t, J=6.8 Hz), 7.22-7.30 (3H, m), 7.62 (2H, d, J=8.4 Hz), 7.56 (1H, d, J=9.6 Hz), 7.62 (1H, d, J=8.0 Hz), 8.14-8.15 (2H, m). MS: 365.0 [MH$^+$].

Example 8

This example is directed to a synthesis of (R)—N-(1-(4-(morpholine-4-carbonyl)phenyl)ethyl)imidazo[1,2-a]pyridine-2-carboxamide.

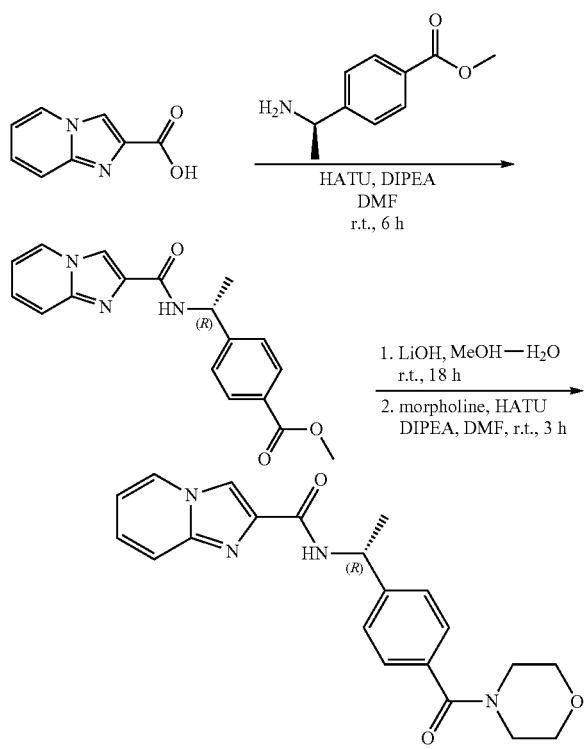

Step A: (R)-methyl 4-(1-(imidazo[1,2-a]pyridine-2-carboxamido)ethyl)benzoate

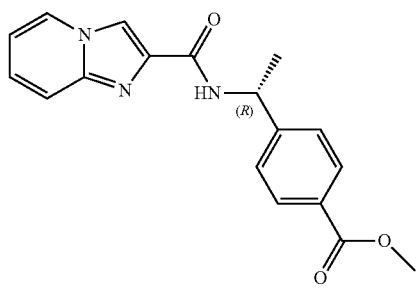

To a solution of imidazo[1,2-a]pyridine-2-carboxylic acid (0.50 g, 3.08 mmol) in DMF (15 mL) was added HATU (1.29 g, 3.39 mmol) and DIPEA (1.35 mL, 7.71 mmol) and the reaction mixture was stirred at room temperature for 2 hours. (R)-methyl 4-(1-aminoethyl)benzoate (0.55 g, 3.08 mmol) was added to the reaction mixture and stirred for 4 h at room temperature. The mixture was quenched with water and extracted with EtOAc. The organic layer was dried over $Na_2SO_4$, filtered, and concentrated in vacuo. The residue was purified by column chromatography (EtOAc) to afford the (R)-methyl 4-(1-(imidazo[1,2-a]pyridine-2-carboxamido)ethyl)benzoate (0.91 g, 91%) as a yellow oil. $^1$H-NMR (CDCl$_3$, Varian, 400 MHz): δ 1.59 (3H, d, J=6.8 Hz), 3.86 (3H, s), 5.32-5.40 (1H, m), 6.77 (1H, t, J=6.4 Hz), 7.45 (2H, d, J=8.4 Hz), 7.51 (1H, d, J=9.2 Hz), 7.76 (1H, d, J=8.4 Hz), 7.96 (2H, d, J=8.4 Hz), 8.06 (1H, dd, J=6.8, 0.8 Hz), 8.15 (1H, s). *NH peak was not observed.

Step B: (R)—N-(1-(4-(morpholine-4-carbonyl)phenyl)ethyl)imidazo[1,2-a]pyridine-2-carboxamide

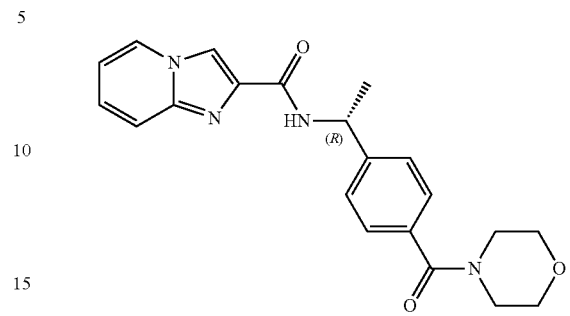

To a solution of (R)-methyl 4-(1-(imidazo[1,2-a]pyridine-2-carboxamido)ethyl)benzoate (0.10 g, 0.31 mmol) in MeOH/water (v/v=9:4; 13 mL) was added lithium hydroxide (0.04 g, 1.55 mmol). The reaction mixture was stirred at room temperature for 18 hours. The reaction mixture was quenched with 1N HCl (3 mL) and concentrated in vacuo to give corresponding carboxylic acid which was used to the next reaction without further purification. The above obtained carboxylic acid was re-dissolved in DMF (7 mL) and HATU (0.14 g, 0.36 mmol) and DIPEA (0.20 mL, 1.13 mmol), addition was followed. After stirred at room temperature for 5 min, morpholine (0.03 g, 0.32 mmol) was added to the reaction mixture and stirred at room temperature for 3 hours. The reaction mixture was partitioned between water and EtOAc and the separated aqueous layer was extracted with EtOAc. The combined organic layers were dried over $Na_2SO_4$, filtered, and concentrated in vacuo. The residue was purified by column chromatography (EtOAc to EtOAc:MeOH=20:1) to afford the (R)—N-(1-(4-(morpholine-4-carbonyl)phenyl)ethyl)imidazo[1,2-a]pyridine-2-carboxamide (71.0 mg, 58%) as a white solid. $^1$H-NMR (CD$_3$OD, Varian, 400 MHz): δ 1.58 (3H, d, J=7.2 Hz), 3.28-3.70 (8H, m), 5.23-5.26 (1H, m), 6.94 (1H, t, J=7.2 Hz), 7.34 (1H, d, J=9.2 Hz), 7.39 (2H, d, J=8.4 Hz), 7.51 (2H, d, J=8.0 Hz), 7.56 (1H, d, J=9.6 Hz), 8.25 (1H, s), 8.43 (1H, d, J=7.2 Hz). *NH peak was not observed. MS: 379.1 [MH$^+$].

Example 9

This example is directed to a synthesis of (R)—N-(1-(4-(dimethylcarbamoyl)phenyl)ethyl)imidazo[1,2-a]pyridine-2-carboxamide.

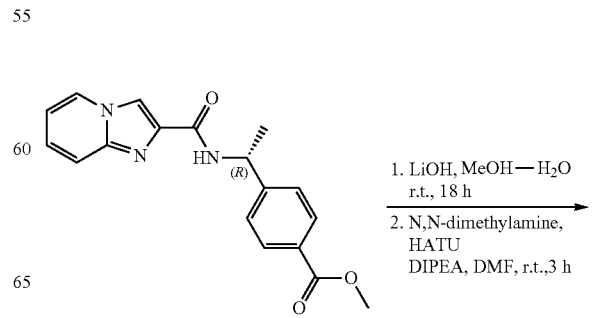

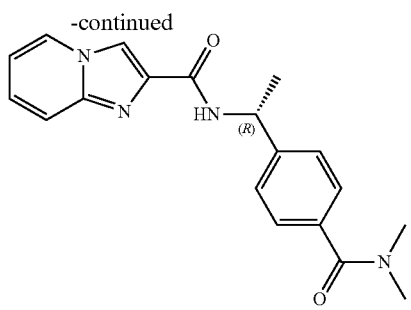

To a solution of (R)-methyl 4-(1-(imidazo[1,2-a]pyridine-2-carboxamido)ethyl)benzoate (Step A of Example 7, 0.10 g, 0.31 mmol) in MeOH/water (v/v=9:4; 13 mL) was added lithium hydroxide (0.04 g, 1.55 mmol). The reaction mixture was stirred at room temperature for 18 hours. The reaction mixture was quenched with 1N HCl (3 mL) and concentrated in vacuo to give corresponding carboxylic acid which was used to the next reaction without further purification. The above obtained carboxylic acid was re-dissolved in DMF (7 mL) and HATU (0.14 g, 0.36 mmol) and DIPEA (0.25 mL, 1.45 mmol), addition was followed. After stirred at room temperature for 5 min, N,N-dimethylamine (0.03 g, 0.32 mmol) was added to the reaction mixture and stirred at room temperature for 3 hours. The reaction mixture was partitioned between water and EtOAc and the separated aqueous layer was extracted with EtOAc. The combined organic layers were dried over Na$_2$SO$_4$, filtered, and concentrated in vacuo. The residue was purified by column chromatography (EtOAc to EtOAc:MeOH=20:1) to afford the (R)—N-(1-(4-(dimethylcarbamoyl)phenyl)ethyl)imidazo[1,2-a]pyridine-2-carboxamide (55.0 mg, 50%) as a brown solid. $^1$H-NMR (CD$_3$OD, Varian, 400 MHz): δ 1.58 (3H, d, J=7.2 Hz), 2.96 (3H, s), 3.06 (3H, s), 5.25-5.27 (1H, m), 6.93 (1H, t, J=6.4 Hz), 7.34 (1H, d, J=8.8 Hz), 7.39 (2H, d, J=8.0 Hz), 7.50 (2H, d, J=8.0 Hz), 7.55 (1H, d, J=8.8 Hz), 8.26 (1H, s), 8.42 (1H, d, J=6.4 Hz). *NH peak was not observed. MS: 337.0 [MH$^+$].

Example 10

This example is directed to a synthesis of (R)—N-(1-(4-(4-methylpiperazine-1-carbonyl)phenyl)ethyl)imidazo[1,2-a]pyridine-2-carboxamide.

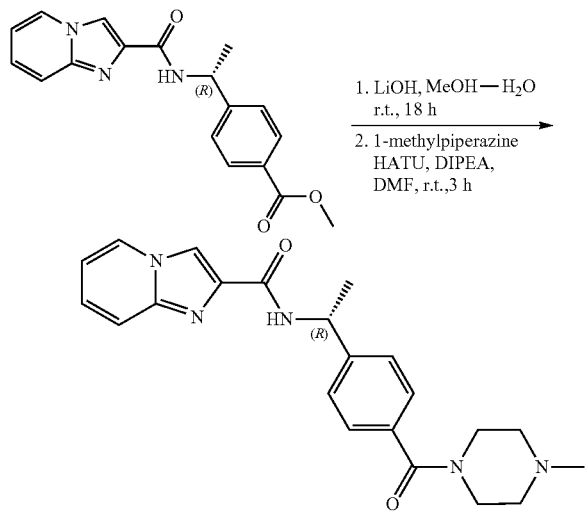

To a solution of (R)-methyl 4-(1-(imidazo[1,2-a]pyridine-2-carboxamido)ethyl)benzoate (Step A of Example 7, 0.10 g, 0.31 mmol) in MeOH/water (v/v=9:4; 13 mL) was added lithium hydroxide (0.04 g, 1.55 mmol). The reaction mixture was stirred at room temperature for 18 hours. The reaction mixture was quenched with 1N HCl (3 mL) and concentrated in vacuo to give corresponding carboxylic acid which was used to the next reaction without further purification. The above obtained carboxylic acid was re-dissolved in DMF (7 mL) and HATU (0.14 g, 0.36 mmol) and DIPEA (0.17 mL, 0.97 mmol), addition was followed. After stirred at room temperature for 5 min, 1-methylpiperazine (0.04 mL, 0.32 mmol) was added to the reaction mixture and stirred at room temperature for 3 hours. The reaction mixture was partitioned between water and EtOAc and the separated aqueous layer was extracted with EtOAc. The combined organic layers were dried over Na$_2$SO$_4$, filtered, and concentrated in vacuo. The residue was purified by column chromatography (EtOAc:MeOH=3:2). The product was purified by prep-LC to afford the (R)—N-(1-(4-(4-methylpiperazine-1-carbonyl)phenyl)ethyl)imidazo[1,2-a]pyridine-2-carboxamide (40.0 mg, 32%) as a yellow oil. $^1$H-NMR (CDCl$_3$, Varian, 400 MHz): δ 1.62 (3H, d, J=7.2 Hz), 2.33 (3H, s), 2.40 (2H, brs), 2.54 (2H, brs), 3.48 (2H, brs), 3.81 (2H, brs), 5.32-5.39 (1H, m), 6.860 (1H, t, J=6.4 Hz), 7.26 (1H, d, J=8.8 Hz), 7.37 (2H, d, J=8.4 Hz), 7.46 (2H, d, J=8.0 Hz), 7.58 (1H, d, J=9.6 Hz), 7.89 (1H, d, J=8.4 Hz), 8.15 (1H, s). *NH peak was not observed. MS: 392.1 [MH$^+$].

Example 11

This example is directed to a synthesis of (R)—N-(1-(4-morpholinophenyl)ethyl)imidazo[1,2-a]pyridine-2-carboxamide.

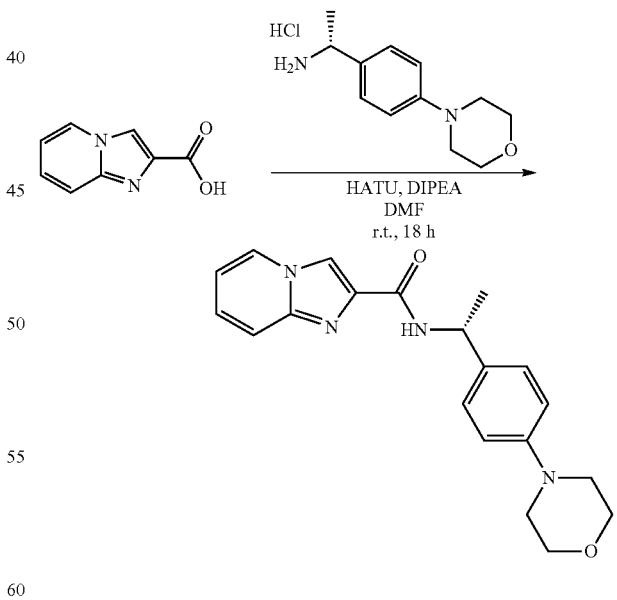

To a solution of imidazo[1,2-a]pyridine-2-carboxylic acid (2.00 g, 12.3 mmol) in DMF (41 mL) were added HATU (7.03 g, 18.5 mmol) and DIPEA (6.46 mL, 4.78 mmol). The reaction mixture was stirred at room temperature for 1 hours. After addition of (R)-1-(4-morpholinophenyl)ethanamine hydrochloride (intermediate 4, 3.89 g, 16.0 mmol), the reaction mixture was stirred at room temperature for 18 hours. The reaction mixture was partitioned between water and DCM and the aqueous layer was extracted with DCM/MeOH (10:1). The combined organic layers were washed with water and brine, dried over Na$_2$SO$_4$, filtered, and concentrated in vacuo. The residue was purified by column chromatography on NH—SiO$_2$ (Hexane:EtOAc=1:1 to EtOAc:MeOH=20:1) to afford the (R)—N-(1-(4-morpholinophenyl)ethyl)imidazo[1,2-a]pyridine-2-carboxamide (3.20 g, 74%) as a white solid. $^1$H-NMR (DMSO-d$_6$, Varian, 400 MHz): δ 1.48 (3H, d, J=7.2 Hz), 3.05 (4H, t, J=4.8 Hz), 3.72 (4H, t, J=4.6 Hz), 5.08-5.13 (1H, m), 6.89 (2H, d, J=8.8 Hz), 6.97 (1H, t, J=6.6 Hz), 7.29 (2H, d, J=8.4 Hz), 7.34 (1H, t, J=8.2 Hz), 7.59 (1H, d, J=9.2 Hz), 8.35 (1H, s), 8.44 (1H, d, J=8.0 Hz), 8.57 (1H, d, J=6.8 Hz). MS: 350.9 [MH$^+$].

Example 12

This example is directed to a synthesis of (R)—N-(1-(4-(4-methylpiperazin-1-yl)phenyl)ethyl)imidazo[1,2-a]pyridine-2-carboxamide.

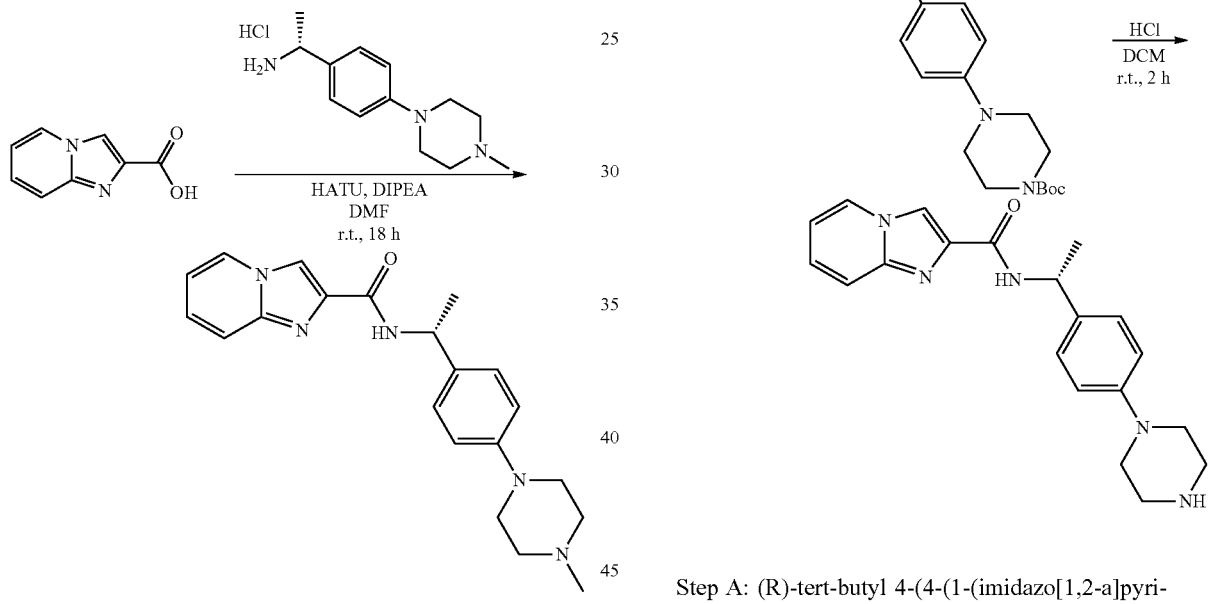

To a solution of imidazo[1,2-a]pyridine-2-carboxylic acid (100 mg, 0.617 mmol) in DMF (6.0 mL) were added HATU (352 mg, 0.925 mmol) and DIPEA (323 µL, 1.85 mmol). The reaction mixture was stirred at room temperature for 1 hours. After addition of (R)-1-(4-(4-methylpiperazin-1-yl)phenyl)ethanamine hydrochloride (intermediate 5, 205 mg, 0.802 mmol), the reaction mixture was stirred at room temperature for 18 hours. The reaction mixture was partitioned between water and EtOAc and the separated aqueous layer was extracted with EtOAc. The combined organic layers were washed with water and brine, dried over Na$_2$SO$_4$, filtered, and concentrated in vacuo. The residue was purified by column chromatography on NH—SiO$_2$ (only EtOAc to EtOAc:MeOH=20:1) to afford the (R)—N-(1-(4-(4-methylpiperazin-1-yl)phenyl)ethyl)imidazo[1,2-a]pyridine-2-carboxamide (126 mg, 56%) as a white solid. $^1$H-NMR (DMSO-d$_6$, Varian, 400 MHz): δ 1.47 (3H, d, J=7.2 Hz), 2.20 (3H, s), 2.42 (4H, t, J=4.6 Hz), 3.08 (4H, t, J=4.6 Hz), 5.05-5.11 (1H, m), 6.89 (2H, d, J=8.8 Hz), 6.97 (1H, t, J=6.8 Hz), 7.27 (2H, d, J=8.8 Hz), 7.34 (1H, t, J=7.4 Hz), 7.59 (1H, d, J=9.2 Hz), 8.35 (1H, s), 8.42 (1H, d, J=8.8 Hz), 8.57 (1H, d, J=7.2 Hz). MS: 364.0 [MH$^+$].

Example 13

This example is directed to a synthesis of (R)—N-(1-(4-(piperazin-1-yl)phenyl)ethyl)imidazo[1,2-a]pyridine-2-carboxamide.

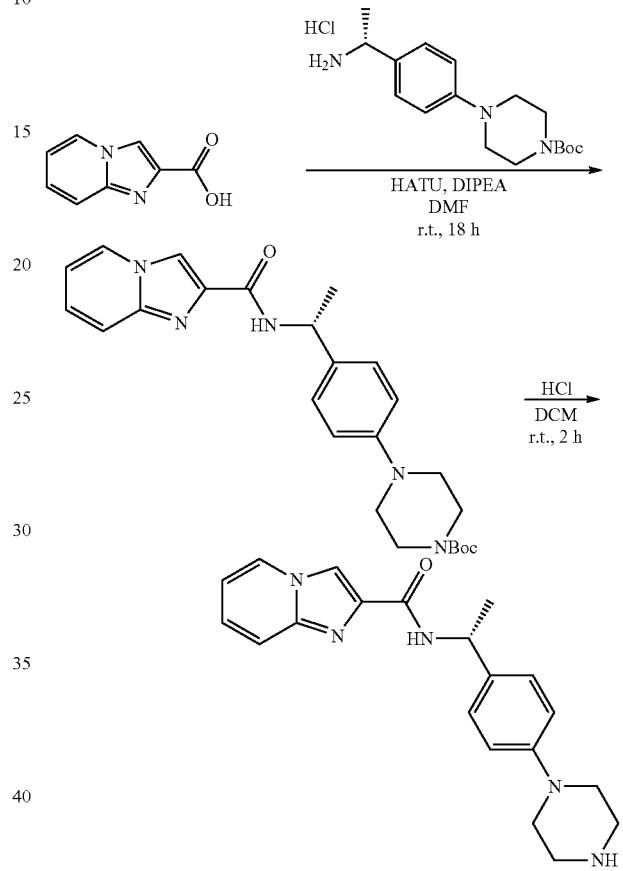

Step A: (R)-tert-butyl 4-(4-(1-(imidazo[1,2-a]pyridine-2-carboxamido)ethyl)phenyl) piperazine-1-carboxylate

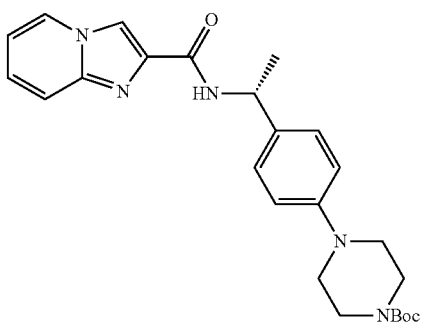 [SMILES: C[C@@H](NC(=O)c1cn2ccccc2n1)c1ccc(N2CCN(C(=O)OC(C)(C)C)CC2)cc1]

To a solution of imidazo[1,2-a]pyridine-2-carboxylic acid (60.0 mg, 0.370 mmol) in DMF (4.0 mL) were added HATU (211 mg, 0.56 mmol) and DIPEA (194 µL, 1.11 mmol). The reaction mixture was stirred at room temperature for 1 hours. After addition of (R)-tert-butyl 4-(4-(1-aminoethyl)phenyl) piperazine-1-carboxylate (intermediate 6, 170 mg, 0.555 mmol), the reaction mixture was stirred at room temperature for 18 hours. The reaction mixture was partitioned between water and EtOAc and the aqueous layer was extracted with EtOAc. The combined organic layers were washed with water and brine, dried over Na$_2$SO$_4$, filtered, and concentrated in vacuo. The residue was purified by column chromatography on SiO$_2$ (Hexane:EtOAc=1:1 to 1:3) to afford the (R)-tert-butyl 4-(4-(1-(imidazo[1,2-a]pyridine-2-carboxamido)ethyl)phenyl) piperazine-1-carboxylate (50.0 mg, 30%) as a white solid. $^1$H-NMR (CDCl$_3$, Varian, 400 MHz): δ 1.48 (9H, s), 1.61 (3H, d, J=7.2 Hz), 3.10 (4H, t, J=4.8 Hz), 3.56 (4H, t, J=5.0 Hz), 5.26-5.33 (1H, m), 6.84 (1H, t, J=7.0 Hz), 6.90 (2H, d, J=8.8 Hz), 7.21-7.26 (1H, m), 7.33 (2H, d, J=8.4 Hz), 7.54-7.58 (2H, m), 8.13-8.14 (2H. m).

Step B: (R)—N-(1-(4-(piperazin-1-yl)phenyl)ethyl) imidazo[1,2-a]pyridine-2-carboxamide

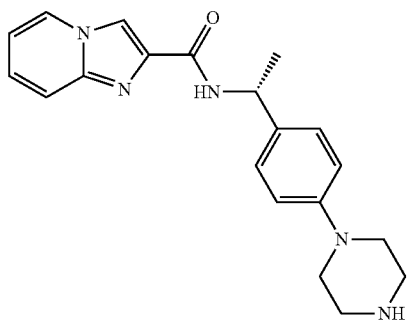 [SMILES: C[C@@H](NC(=O)c1cn2ccccc2n1)c1ccc(N2CCNCC2)cc1]

To a solution of (R)-tert-butyl 4-(4-(1-(imidazo[1,2-a]pyridine-2-carboxamido)ethyl)phenyl) piperazine-1-carboxylate (50.0 mg, 0.11 mmol) in DCM (3.0 mL) was added HCl (4 M in dioxane, 278 μL, 1.11 mmol). After stirred at room temperature for 2 hours, the reaction mixture was concentrated in vacuo. The residue was diluted with DCM and basified with 2 N NaOH, washed with water and brine. The separated organic layer was dried over Na$_2$SO$_4$, filtered, and concentrated in vacuo. The residue was purified by column chromatography on NH—SiO$_2$ (EtOAc to EtOAc: MeOH=10:1) to afford the (R)—N-(1-(4-(piperazin-1-yl) phenyl)ethyl)imidazo[1,2-a]pyridine-2-carboxamide (32.0 mg, 82%) as a white solid. $^1$H-NMR (DMSO-d$_6$, Varian, 400 MHz): δ 1.48 (3H, d, J=7.2 Hz), 2.81 (4H, t, J=4.8 Hz), 2.99 (4H, t, J=5.0 Hz), 5.05-5.10 (1H, m), 6.86 (2H, d, J=8.4 Hz), 6.97 (1H, t, J=7.0 Hz), 7.26 (2H, d, J=8.8 Hz), 7.34 (1H, t, J=8.4 Hz), 7.59 (1H, d, J=9.6 Hz), 8.34 (1H, s), 8.41 (1H, d, J=8.8 Hz), 8.57 (1H, d, J=7.2 Hz). *NH proton was not observed.

Example 14

This example is directed to a synthesis of (R)—N-(1-phenylpropan-2-yl)imidazo[1,2-a]pyridine-2-carboxamide.

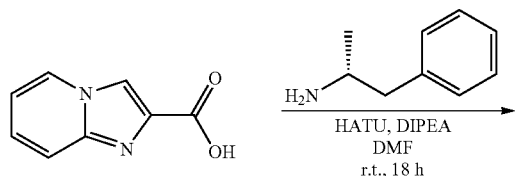

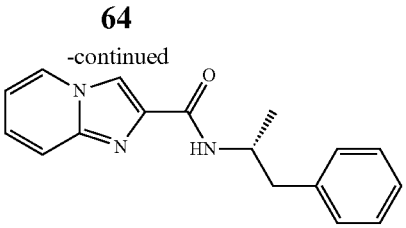

To a solution of imidazo[1,2-a]pyridine-2-carboxylic acid (50.0 mg, 0.31 mmol) in DMF (3.0 mL) were added HATU (176 mg, 0.46 mmol) and DIPEA (162 μL, 0.93 mmol). The reaction mixture was stirred at room temperature for 1 hour. After addition of (R)-1-phenylpropan-2-amine (intermediate 7, 54.0 mg, 0.37 mmol), the reaction mixture was stirred at room temperature for 18 hours. The reaction mixture was partitioned between water and EtOAc and the aqueous layer was extracted with EtOAc. The combined organic layers were washed with water and brine, dried over Na$_2$SO$_4$, filtered, and concentrated in vacuo. The residue was purified by column chromatography on SiO$_2$ (EtOAc:Hexane=1:1 to EtOAc) to afford the (R)—N-(1-phenylpropan-2-yl)imidazo [1,2-a]pyridine-2-carboxamide (54.0 mg, 63%) as a brown oil. $^1$H-NMR (DMSO-d$_6$, Varian, 400 MHz): δ 1.16 (3H, d, J=6.8 Hz), 2.76 (1H, dd, J=6.6, 13.4 Hz), 2.95 (1H, dd, J=7.4, 13.4 Hz), 4.23-4.30 (1H, m), 6.97 (1H, t, J=6.8 Hz), 7.14-7.18 (1H, m), 7.22-7.28 (4H, m), 7.33 (1H, t, J=8.0 Hz), 7.58 (1H, d, J=9.6 Hz), 8.15 (1H, d, J=8.8 Hz), 8.30 (1H, s), 8.56 (1H, d, J=6.8 Hz). MS: 280.1 [MH$^+$].

Example 15

This example is directed to a synthesis of (R)-5-methyl-N-(1-(4-morpholinophenyl)ethyl)imidazo[1,2-a]pyridine-2-carboxamide.

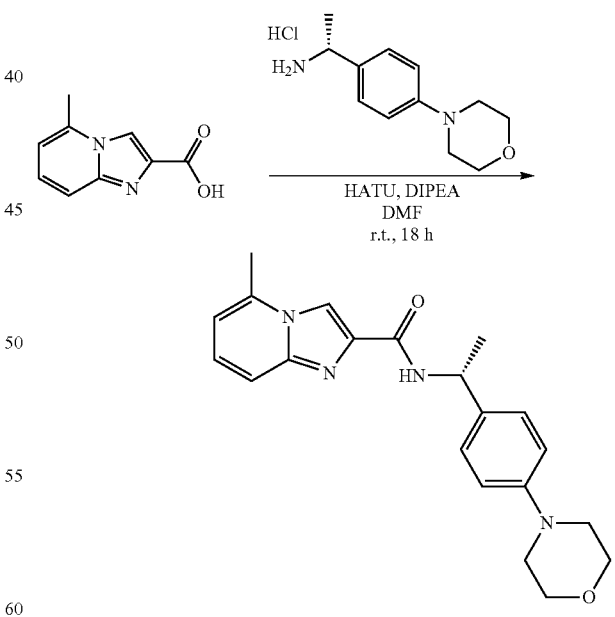

To a solution of 5-methylimidazo[1,2-a]pyridine-2-carboxylic acid (100 mg, 0.57 mmol) in DMF (6.0 mL) were added HATU (324 mg, 0.851 mmol) and DIPEA (297 μL, 1.70 mmol). The reaction mixture was stirred at room temperature for 1 hour. After addition of (R)-1-(4-morpholinophenyl)ethanamine hydrochloride (intermediate 4, 207 mg, 0.851 mmol), the reaction mixture was stirred at room temperature for 18 hours. The reaction mixture was partitioned between water and EtOAc and the separated aqueous layer was extracted with EtOAc. The combined organic layers were washed with water and brine, dried over $Na_2SO_4$, filtered, and concentrated in vacuo. The residue was purified by column chromatography on NH—$SiO_2$ (Hexane:EtOAc=1:1 to 1:3) to afford the (R)-5-methyl-N-(1-(4-morpholinophenyl)ethyl)imidazo[1,2-a]pyridine-2-carboxamide (90.0 mg, 44%) as a white solid. $^1$H-NMR (DMSO-$d_6$, Varian, 400 MHz): δ 1.49 (3H, d, J=7.2 Hz), 2.63 (3H, s), 3.05 (4H, t, J=5.0 Hz), 3.72 (4H, t, J=4.6 Hz), 5.08-5.16 (1H, m), 6.85 (1H, d, J=6.8 Hz), 6.89 (2H, d, J=8.8 Hz), 7.28-7.34 (3H, m), 7.50 (1H, d, J=9.2 Hz), 8.22 (1H, s), 8.46 (1H, d, J=8.8 Hz). MS: 365.3 [MH$^+$].

Example 16

This example is directed to a synthesis of (R)-6-methyl-N-(1-(4-morpholinophenyl)ethyl)imidazo[1,2-a]pyridine-2-carboxamide.

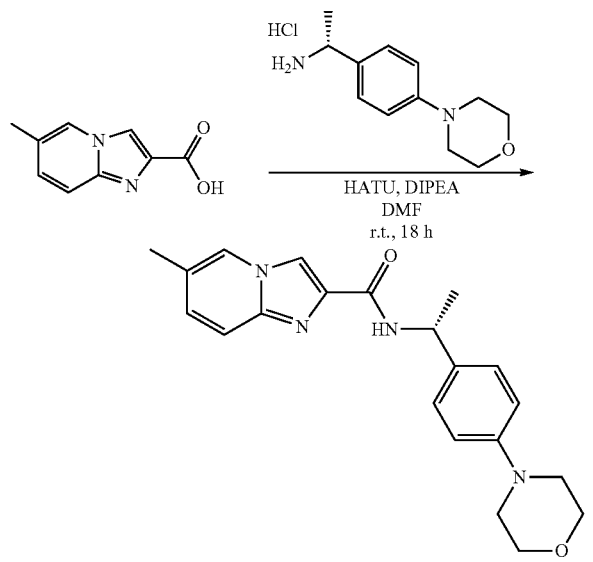

To a solution of 6-methylimidazo[1,2-a]pyridine-2-carboxylic acid (100 mg, 0.57 mmol) in DMF (6.0 mL) were added HATU (324 mg, 0.851 mmol) and DIPEA (297 μL, 1.70 mmol). The reaction mixture was stirred at room temperature for 1 hours. After addition of (R)-1-(4-morpholinophenyl)ethanamine hydrochloride (intermediate 4, 207 mg, 0.851 mmol), the reaction mixture was stirred at room temperature for 18 hours. The reaction mixture was partitioned between water and EtOAc and the separated aqueous layer was extracted with EtOAc. The combined organic layers were washed with water and brine, dried over $Na_2SO_4$, filtered, and concentrated in vacuo. The residue was purified by column chromatography on NH—$SiO_2$ (Hexane:EtOAc=1:1 to 1:3) to afford the (R)-6-methyl-N-(1-(4-morpholinophenyl)ethyl)imidazo[1,2-a]pyridine-2-carboxamide (105 mg, 51%) as a white solid. $^1$H-NMR (DMSO-$d_6$, Varian, 400 MHz): δ 1.47 (3H, d, J=7.2 Hz), 2.77 (3H, s), 3.05 (4H, t, J=4.6 Hz), 3.72 (4H, t, J=4.6 Hz), 5.06-5.10 (1H, m), 6.89 (2H, d, J=8.8 Hz), 7.20 (1H, d, J=8.8 Hz), 7.28 (2H, d, J=8.8 Hz), 7.50 (1H, d, J=8.8 Hz), 8.24 (1H, s), 8.37-8.40 (2H, m). MS: 365.3 [MH$^+$].

Example 17

This example is directed to a synthesis of (R)-7-methyl-N-(1-(4-morpholinophenyl)ethyl)imidazo[1,2-a]pyridine-2-carboxamide.

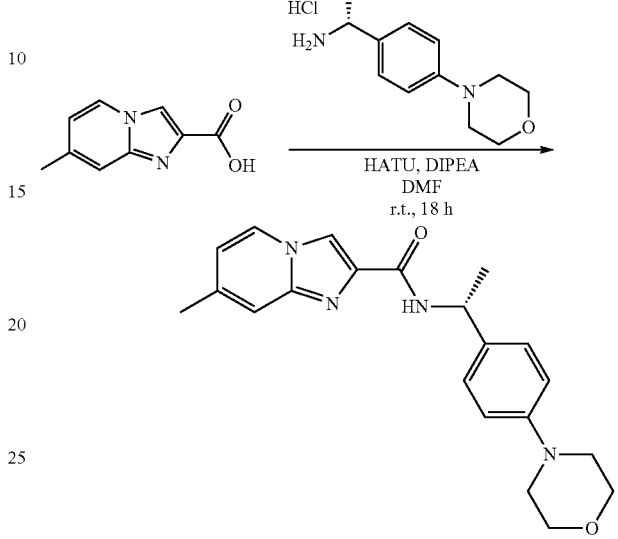

To a solution of 7-methylimidazo[1,2-a]pyridine-2-carboxylic acid (100 mg, 0.57 mmol) in DMF (6.0 mL) were added HATU (324 mg, 0.851 mmol) and DIPEA (297 μL, 1.70 mmol). The reaction mixture was stirred at room temperature for 1 hours. After addition of (R)-1-(4-morpholinophenyl)ethanamine hydrochloride (intermediate 4, 207 mg, 0.851 mmol), the reaction mixture was stirred at room temperature for 18 hours. The reaction mixture was partitioned between water and EtOAc and the separated aqueous layer was extracted with EtOAc. The combined organic layers were washed with water and brine, dried over $Na_2SO_4$, filtered, and concentrated in vacuo. The residue was purified by column chromatography on NH—$SiO_2$ (Hexane:EtOAc=1:1 to 1:3) to afford the (R)-7-methyl-N-(1-(4-morpholinophenyl)ethyl)imidazo[1,2-a]pyridine-2-carboxamide (130 mg, 63%) as a white solid. $^1$H-NMR (DMSO-$d_6$, Varian, 400 MHz): δ 1.47 (3H, d, J=7.2 Hz), 2.36 (3H, s), 3.05 (4H, t, J=4.8 Hz), 3.72 (4H, t, J=4.6 Hz), 5.06-5.10 (1H, m), 6.82 (1H, d, J=6.4 Hz), 6.89 (2H, d, J=8.8 Hz), 7.28 (2H, d, J=8.8 Hz), 7.34 (1H, s), 8.24 (1H, s), 8.38 (1H, d, J=8.4 Hz), 8.45 (1H, d, J=7.2 Hz). MS: 365.3 [MH$^+$].

Example 18

This example is directed to a synthesis of (R)-8-methyl-N-(1-(4-morpholinophenyl)ethyl)imidazo[1,2-a]pyridine-2-carboxamide.

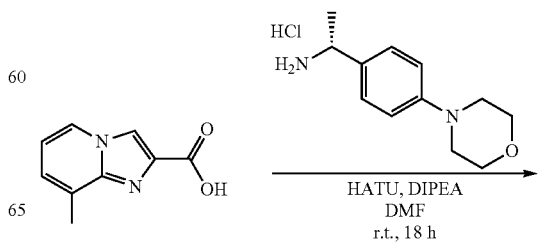

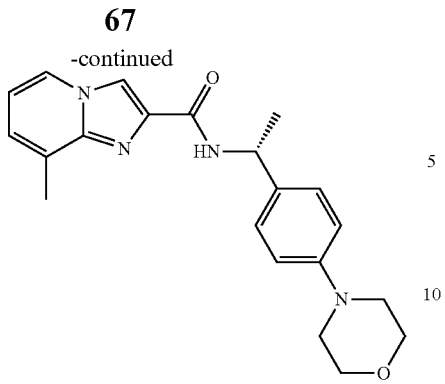

To a solution of 8-methylimidazo[1,2-a]pyridine-2-carboxylic acid (100 mg, 0.57 mmol) in DMF (6.0 mL) were added HATU (324 mg, 0.851 mmol) and DIPEA (297 μL, 1.70 mmol). The reaction mixture was stirred at room temperature for 1 hours. After addition of (R)-1-(4-morpholinophenyl)ethanamine hydrochloride (intermediate 4, 207 mg, 0.851 mmol), the reaction mixture was stirred at room temperature for 18 hours. The reaction mixture was partitioned between water and EtOAc and the separated aqueous layer was extracted with EtOAc. The combined organic layers were washed with water and brine, dried over $Na_2SO_4$, filtered, and concentrated in vacuo. The residue was purified by column chromatography on $NH-SiO_2$ (Hexane:EtOAc=1:1 to 1:3) to afford the (R)-8-methyl-N-(1-(4-morpholinophenyl)ethyl)imidazo[1,2-a]pyridine-2-carboxamide (72.0 mg, 35%) as a white solid. $^1$H-NMR (DMSO-$d_6$, Varian, 400 MHz): δ 1.50 (3H, d, J=6.4 Hz), 2.52 (3H, s), 3.06 (4H, t, J=5.0 Hz), 3.72 (4H, t, J=4.6 Hz), 5.10-5.15 (1H, m), 6.85-6.92 (3H, m), 7.13 (1H, d, J=6.8 Hz), 7.29 (2H, d, J=8.4 Hz), 8.21 (1H, d, J=8.4 Hz), 8.34 (1H, s), 8.41 (1H, d, J=6.8 Hz). MS: 365.4 [MH$^+$].

Example 19

This example is directed to a synthesis of (R)—N-(1-(4-(4-(methylsulfonyl)piperazin-1-yl)phenyl)ethyl)imidazo[1,2-a]pyridine-2-carboxamide.

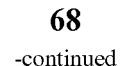

To a solution of (R)—N-(1-(4-(piperazin-1-yl)phenyl)ethyl)imidazo[1,2-a]pyridine-2-carboxamide (example 12, 50.0 mg, 0.130 mmol) in DCM (3.0 mL) was added TEA (36.0 L, 0.26 mmol), followed by mesyl chloride (12.0 μL, 0.16 mmol) at room temperature. The reaction mixture was stirred at room temperature for 1 hours, and quenched with water. The aqueous layer was extracted with DCM. The combined organic layers were dried over $Na_2SO_4$, filtered, and concentrated in vacuo. The residue was purified by column chromatography on $NH-SiO_2$ (EtOAc to EtOAc:MeOH=20:1) to afford the (R)—N-(1-(4-(4-(methylsulfonyl)piperazin-1-yl)phenyl)ethyl)imidazo[1,2-a]pyridine-2-carboxamide (37 mg, 67%) as a white solid. $^1$H-NMR (DMSO-$d_6$, Varian, 400 MHz): δ 1.48 (3H, d, J=7.2 Hz), 2.91 (3H, s), 3.21-3.22 (8H, m), 5.08-5.13 (1H, m), 6.92-6.99 (3H, m), 7.29-7.36 (3H. m), 7.59 (1H, d, J=9.2 Hz), 8.34 (1H, s), 8.46 (1H, d, J=8.4 Hz), 8.57 (1H, d, J=6.4 Hz). MS: 428.2 [MH$^+$].

Example 20

This example is directed to a synthesis of (R)—N-(1-(4-(4-acetylpiperazin-1-yl)phenyl)ethyl)imidazo[1,2-a]pyridine-2-carboxamide.

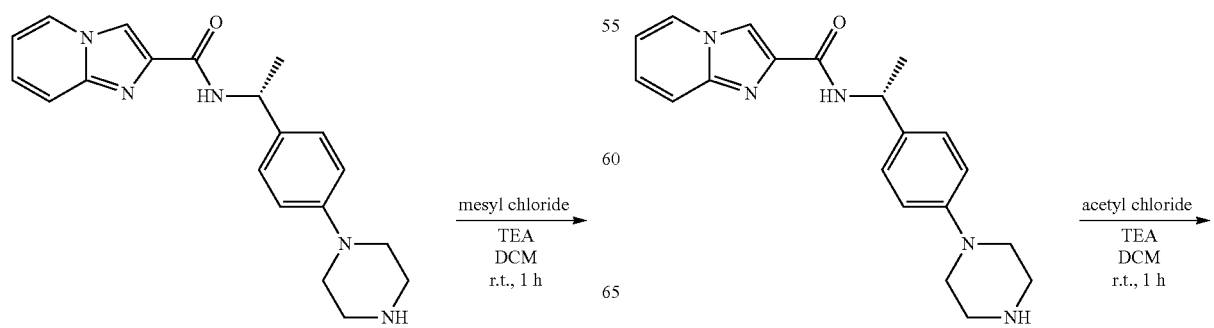

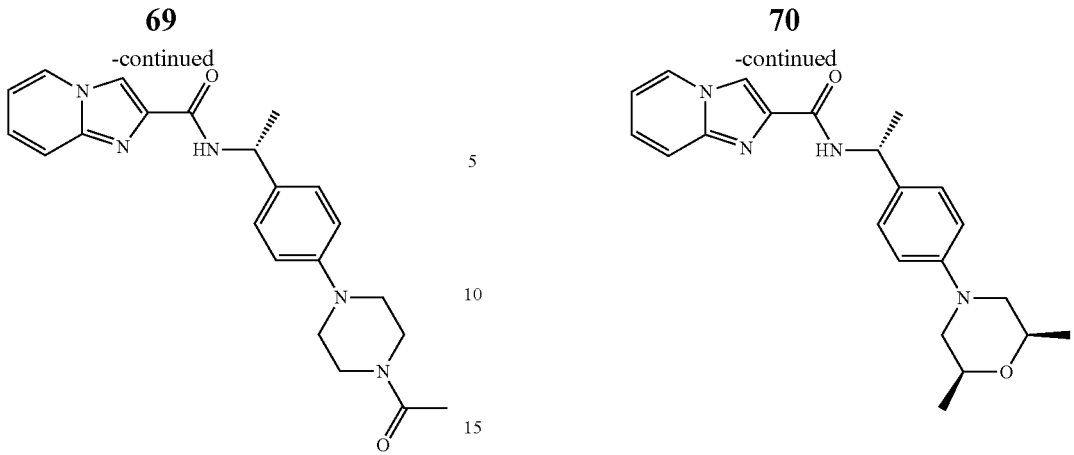

To a solution of (R)—N-(1-(4-(piperazin-1-yl)phenyl)ethyl)imidazo[1,2-a]pyridine-2-carboxamide (example 12, 50.0 mg, 0.13 mmol) in DCM (3.0 mL) was added TEA (36.0 μL, 0.260 mmol), followed by acetyl chloride (11.0 μL, 0.16 mmol) at room temperature. The reaction mixture was stirred at room temperature for 1 hours, and quenched with water. The aqueous layer was extracted with DCM. The combined organic layers were dried over $Na_2SO_4$, filtered, and concentrated in vacuo. The residue was purified by column chromatography on NH—$SiO_2$ (EtOAc to EtOAc:MeOH=97:3) to afford the (R)—N-(1-(4-(4-acetylpiperazin-1-yl)phenyl)ethyl)imidazo[1,2-a]pyridine-2-carboxamide (35 mg, 69%) as a white solid. $^1$H-NMR (DMSO-$d_6$, Varian, 400 MHz): δ 1.48 (3H, d, J=7.2 Hz), 2.03 (3H, s), 3.04-3.05 (2H, m), 3.09-3.11 (2H, m), 3.54-3.55 (4H, m), 5.07-5.11 (1H, m), 6.91 (2H, d, J=8.8 Hz), 6.97 (1H, t, J=6.4 Hz), 7.29 (2H, d, J=8.4 Hz), 7.34 (1H, t, J=8.2 Hz), 7.59 (1H, d, J=9.2 Hz), 8.34 (1H, s), 8.46 (1H, d, J=8.4 Hz), 8.57 (1H, d, J=7.2 Hz). MS Found: 392.2 [MH$^+$].

Example 21

This example is directed to a synthesis of N—((R)-1-(4-((2S,6R)-2,6-dimethylmorpholino)phenyl)ethyl)imidazo[1,2-a]pyridine-2-carboxamide.

To a solution of imidazo[1,2-a]pyridine-2-carboxylic acid (24.0 mg, 0.15 mmol) in DMF (2.0 mL) were added HATU (84.0 mg, 0.22 mmol) and DIPEA (77 μL, 0.44 mmol). The reaction mixture was stirred for 1 hour at room temperature. After addition of (R)-1-(4-((2S,6R)-2,6-dimethylmorpholino)phenyl)ehtylamine hydrochloride (intermediate 8, 60.0 mg, 0.22 mmol), the reaction mixture was stirred for 3 hours at room temperature. The reaction mixture was partitioned between water and EtOAc and the separated aqueous layer was extracted with EtOAc. The combined organic layers were washed with water and brine, dried over $Na_2SO_4$, filtered, and concentrated in vacuo. The residue was purified by column chromatography on NH—$SiO_2$ (Hexane:EtOAc=1:1 to 1:2) to afford the N—((R)-1-(4-((2S,6R)-2,6-dimethylmorpholino)phenyl)ethyl)imidazo[1,2-a]pyridine-2-carboxamide (32.0 mg, 57%) as a white solid. $^1$H-NMR (CDCl$_3$, Varian, 400 MHz): δ 1.23 (6H, d, J=6.0 Hz), 1.59 (3H, d, J=7.2 Hz), 2.34-2.40 (2H, m), 3.40 (2H, d, J=10.8 Hz), 3.74-3.81 (2H, m), 5.23-5.29 (1H, m), 7.20-7.24 (1H, m), 7.32 (2H, d, J=8.8 Hz), 7.53 (1H, d, J=9.2 Hz), 7.59 (1H, d, J=8.0 Hz), 8.11-8.13 (2H, m). MS: 379.2 [MH$^+$].

Example 22

This example is directed to a synthesis of N—((R)-1-(4-((R)-3-methylmorpholino)-phenyl)ethyl)imidazo[1,2-a]pyridine-2-carboxamide.

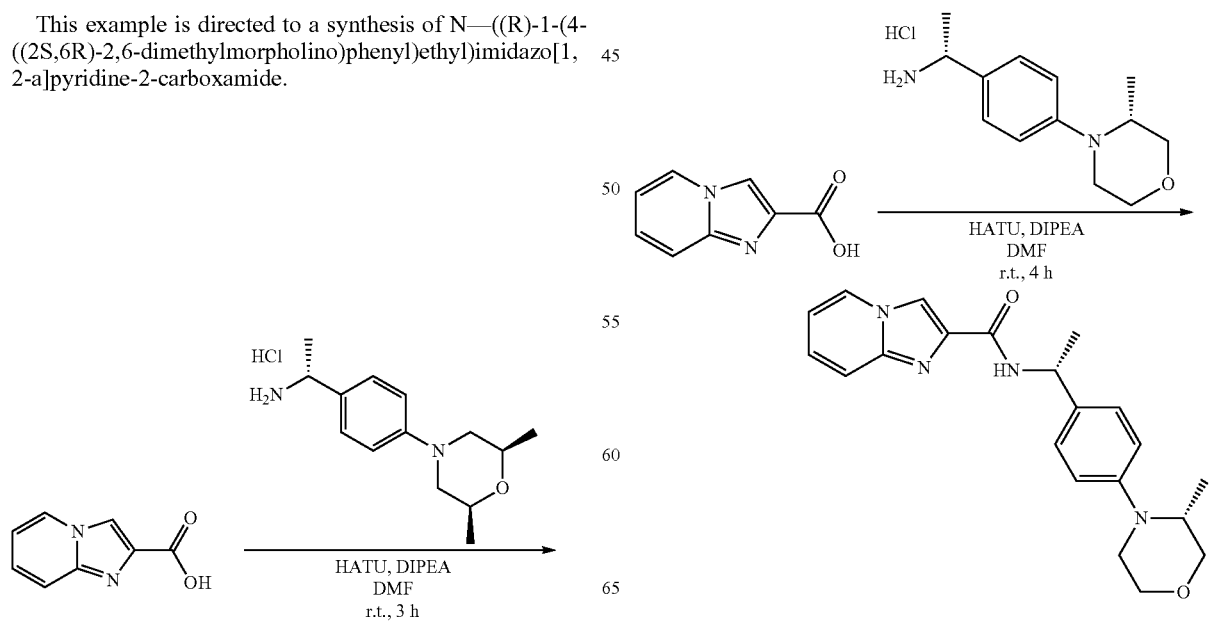

To a solution of imidazo[1,2-a]pyridine-2-carboxylic acid (21.0 mg, 0.13 mmol) in DMF (2.0 mL) were added HATU (74.0 mg, 0.19 mmol) and DIPEA (68 μL, 0.38 mmol). The reaction mixture was stirred for 1 hour at room temperature. After addition of (R)-1-(4-((R)-3-methylmorpholino)phenyl)ethanamine hydrochloride (intermediate 9, 50.0 mg, 0.19 mmol), the reaction mixture was stirred for 3 hours at room temperature. The reaction mixture was partitioned between water and EtOAc and the separated aqueous layer was extracted with EtOAc. The combined organic layers were washed with water and brine, dried over Na$_2$SO$_4$, filtered, and concentrated in vacuo. The residue was purified by column chromatography on SiO$_2$ (EtOAc) to afford the N—((R)-1-(4-((R)-3-methylmorpholino)phenyl)ethyl)imidazo[1,2-a]pyridine-2-carboxamide (16.0 mg, 33%) as a white solid. $^1$H-NMR (CDCl$_3$, Varian, 400 MHz): δ 1.05 (3H, d, J=6.8 Hz), 1.61 (3H, d, J=7.2 Hz), 3.06-3.16 (2H, m), 3.67-3.74 (3H, m), 3.83-3.86 (1H, m), 3.93-3.97 (1H, m), 5.28-5.32 (1H, m), 6.82-6.87 (3H, m), 7.21-7.23 (1H, m), 7.32 (2H, d, J=8.8 Hz), 7.54 (2H, d, J=9.6 Hz), 8.13-8.14 (2H, m). MS: 365.3 [MH$^+$].

Example 23

This example is directed to a synthesis of (R)—N-(1-(4-(2,2-dimethylmorpholino)phenyl)ethyl)imidazo[1,2-a]pyridine-2-carboxamide.

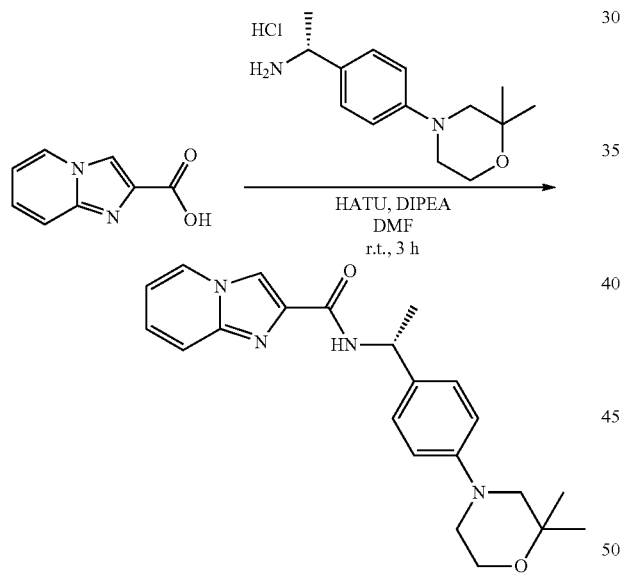

To a solution of imidazo[1,2-a]pyridine-2-carboxylic acid (40.0 mg, 0.24 mmol) in DMF (3.0 mL) were added HATU (140 mg, 0.36 mmol) and DIPEA (130 μL, 0.73 mmol). The reaction mixture was stirred for 3 hours at room temperature. After addition of (R)-1-(4-(2,2-dimethylmorpholino)phenyl)ethanamine hydrochloride (intermediate 10, 100 mg, 0.36 mmol), the reaction mixture was stirred for 3 hours at room temperature. The reaction mixture was partitioned between water and EtOAc and the separated aqueous layer was extracted with EtOAc. The combined organic layers were washed with water and brine, dried over Na$_2$SO$_4$, filtered, and concentrated in vacuo. The residue was purified by column chromatography on NH—SiO$_2$ (Hexane: EtOAc=1:1 to 1:2) to afford the (R)—N-(1-(4-(2,2-dimethylmorpholino)phenyl)ethyl)imidazo[1,2-a]pyridine-2-carboxamide (60.0 mg, 64%) as a white solid. $^1$H-NMR (CDCl$_3$, Varian, 400 MHz): δ 1.31 (6H, s), 1.60 (3H, d, J=6.8 Hz), 2.91 (2H, s), 3.86 (2H, t, J=4.8 Hz), 3.86 (2H, t, J=4.8 Hz), 5.26-5.30 (1H, m), 6.80-6.86 (3H, m), 7.20-7.24 (1H, m), 7.32 (2H, d, J=8.8 Hz), 7.53 (1H, d, J=9.2 Hz), 7.59 (1H, d, J=8.0 Hz), 8.11-8.13 (2H, m). MS: 379.2 [MH$^+$].

Example 24

This example is directed to a synthesis of N—((R)-1-(4-((S)-3-methylmorpholino)phenyl)ethyl)imidazo[1,2-a]pyridine-2-carboxamide.

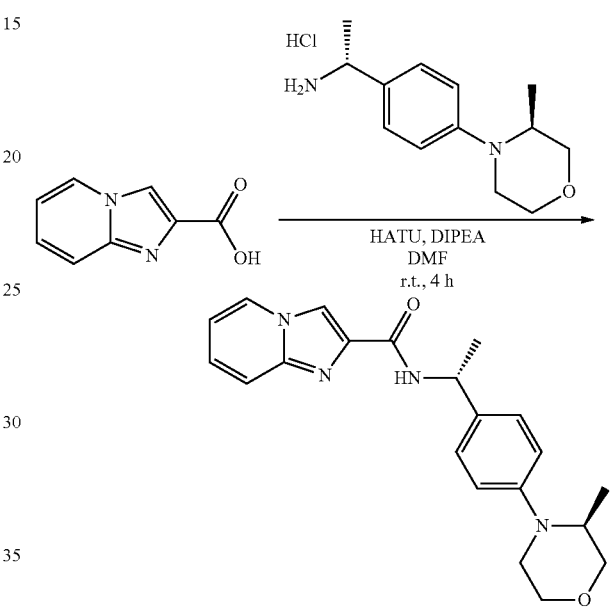

To a solution of imidazo[1,2-a]pyridine-2-carboxylic acid (46.0 mg, 0.28 mmol) in DMF (3.0 mL) were added HATU (163 mg, 0.43 mmol) and DIPEA (150 μL, 0.85 mmol). The reaction mixture was stirred for 1 hour at room temperature. After addition of (R)-1-(4-((S)-3-methylmorpholino)phenyl)ethanamine hydrochloride (intermediate 11, 110 mg, 0.42 mmol), the reaction mixture was stirred for 4 hours at room temperature. The reaction mixture was partitioned between water and EtOAc and the separated aqueous layer was extracted with EtOAc. The combined organic layers were washed with water and brine, dried over Na$_2$SO$_4$, filtered, and concentrated in vacuo. The residue was purified by column chromatography on NH—SiO$_2$ (Hexane: EtOAc=1:1 to EtOAc) to afford the N—((R)-1-(4-((S)-3-methylmorpholino)phenyl)ethyl)imidazo[1,2-a]pyridine-2-carboxamide (55.0 mg, 52%) as a white solid. $^1$H-NMR (CDCl$_3$, Varian, 400 MHz): δ 1.05 (3H, d, J=6.4 Hz), 1.61 (3H, d, J=6.4 Hz), 3.05-3.16 (2H, m), 3.66-3.73 (3H, m), 3.82-3.86 (1H, m), 3.93-3.98 (1H, m), 5.27-5.34 (1H, m), 6.82-6.87 (3H, m), 7.21-7.25 (1H, m), 7.33 (2H, d, J=8.8 Hz), 7.54 (1H, d, J=9.2 Hz), 7.59 (1H, d, J=8.0 Hz), 8.12-8.14 (2H, m). MS: 365.3 [MH$^+$].

Example 25

This example is directed to a synthesis of (R)—N-(1-(4-morpholinophenyl)ethyl)imidazo[1,2-a]pyrazine-2-carboxamide.

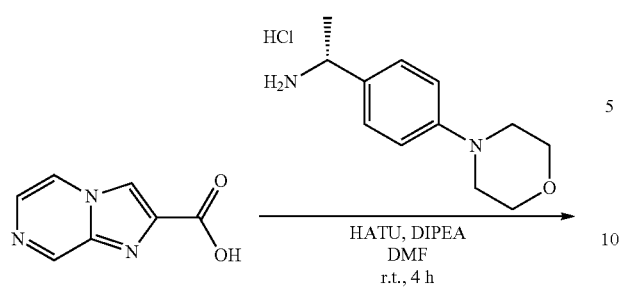

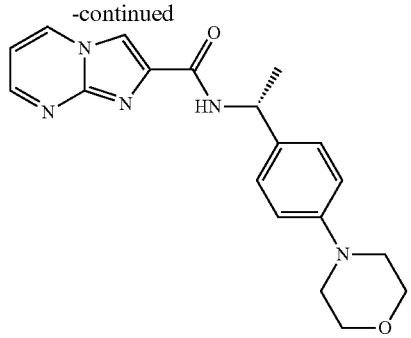

To a solution of imidazo[1,2-a]pyrimidine-2-carboxylic acid (100 mg, 0.61 mmol) in DMF (6.1 mL) was added (R)-1-(4-morpholinophenyl)ethanamine hydrochloride (intermediate 4, 149 mg, 0.61 mmol), HATU (350 mg, 0.92 mmol) and DIPEA (321 μL, 1.84 mmol) at room temperature. The reaction mixture was stirred at room temperature for 4 hours. After quenched by addition of water, the mixture was extracted with EtOAc. The separated organic layer was washed with brine, dried over $Na_2SO_4$, filtered, and concentrated in vacuo. The residue was purified by column chromatography on NH—$SiO_2$ (EtOAc) to afford the (R)—N-(1-(4-morpholinophenyl)ethyl)imidazo[1,2-a]pyrimidine-2-carboxamide (180 mg, 84%) as a white solid. $^1$H-NMR (400 MHz, DMSOd$_6$): δ 1.47 (3H, d, J=7.2 Hz), 3.03 (4H, t, J=5.0 Hz), 3.70 (4H, t, J=4.8 Hz), 5.05-5.12 (1H, m), 6.87 (2H, d, J=9.2 Hz), 7.11 (1H, dd, J=6.6 and 4.2 Hz), 7.27 (2H, d, J=8.8 Hz), 8.27 (1H, s), 8.62-8.64 (2H, m), 8.97 (1H, dd, J=6.8 and 2.0 Hz).

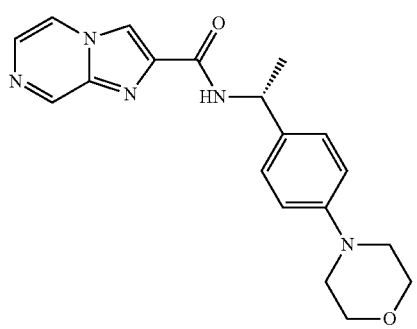

To a solution of imidazo[1,2-a]pyrazine-2-carboxylic acid (100 mg, 0.61 mmol) in DMF (6.1 mL) was added HATU (350 mg, 0.92 mmol), DIPEA (321 μL, 1.84 mmol) and (R)-1-(4-morpholinophenyl)ethanamine hydrochloride (intermediate 4,149 mg, 0.61 mmol) at room temperature. The reaction mixture was stirred at room temperature for 4 hours. After quenched by addition of water, the mixture was extracted with EtOAc. The separated organic layer was washed with brine, dried over $Na_2SO_4$, filtered, and concentrated in vacuo. The residue was purified by column chromatography on NH—$SiO_2$ (EtOAc) to afford the (R)—N-(1-(4-morpholinophenyl)ethyl)imidazo[1,2-a]pyrazine-2-carboxamide (190 mg, 88%) as a yellow solid. $^1$H-NMR (400 MHz, DMSOd$_6$): δ 1.46 (3H, d, J=7.2 Hz), 3.03 (4H, t, J=4.8 Hz), 3.70 (4H, t, J=4.8 Hz), 5.07-5.10 (1H, m), 6.87 (2H, d, J=8.8 Hz), 7.27 (2H, d, J=8.8 Hz), 7.94 (1H, d, J=4.4 Hz), 8.47 (1H, s), 8.59 (1H, dd, J=4.8 and 1.6 Hz), 8.68 (1H, d, J=8.4 Hz), 9.11 (1H, s).

Example 26

This example is directed to a synthesis of (R)—N-(1-(4-morpholinophenyl)ethyl)imidazo[1,2-a]pyrimidine-2-carboxamide.

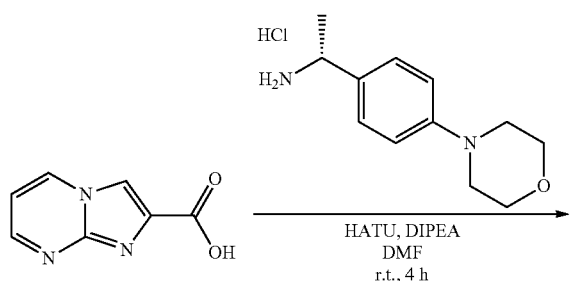

Example 27

This example is directed to a synthesis of (R)—N-(1-phenylethyl)pyrazolo[1,5-a]pyridine-2-carboxamide.

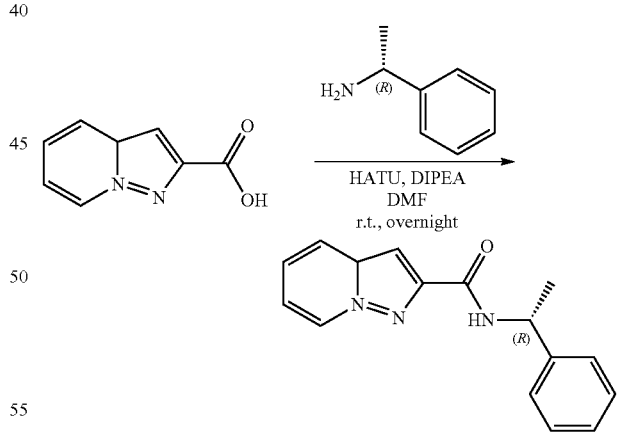

The mixture of pyrazolo[1,5-a]pyridine-2-carboxylic acid (100 mg, 0.62 mmol), (R)-1-phenylethanamine (79.0 μL, 0.62 mmol), HATU (258 mg, 0.68 mmol), and DIPEA (269 μL, 1.54 mmol) in DMF (3.0 mL) was stirred overnight at room temperature. The reaction mixture was partitioned between water and EtOAc and the aqueous layer was extracted with EtOAc. The combined organic layers were washed with water and brine, dried over $Na_2SO_4$, filtered, and concentrated in vacuo. The residue was purified by column chromatography on $SiO_2$ (Hexane:EtOAc=1:1) to afford the (R)—N-(1-phenylethyl)pyrazolo[1,5-a]pyridine-2-carboxamide (155 mg, 95%) as a yellow solid. ¹H-NMR (CDCl₃, Varian, 400 MHz): δ 1.64 (3H, d, J=6.8 Hz), 5.29-5.41 (1H, m), 6.84 (1H, t, J=6.8 Hz), 7.06 (1H, s), 7.11-7.15 (1H, m), 7.25-7.28 (1H, m), 7.35-7.37 (3H, m), 7.43 (2H, d, J=7.2 Hz), 7.57 (1H, d, J=9.2 Hz), 8.36 (1H, d, J=7.2). MS: 351.2 [MH⁺].

Example 28

This example is directed to a synthesis of (R)—N-(1-(4-morpholinophenyl)ethyl) pyrazolo[1,5-a]pyridine-2-carboxamide.

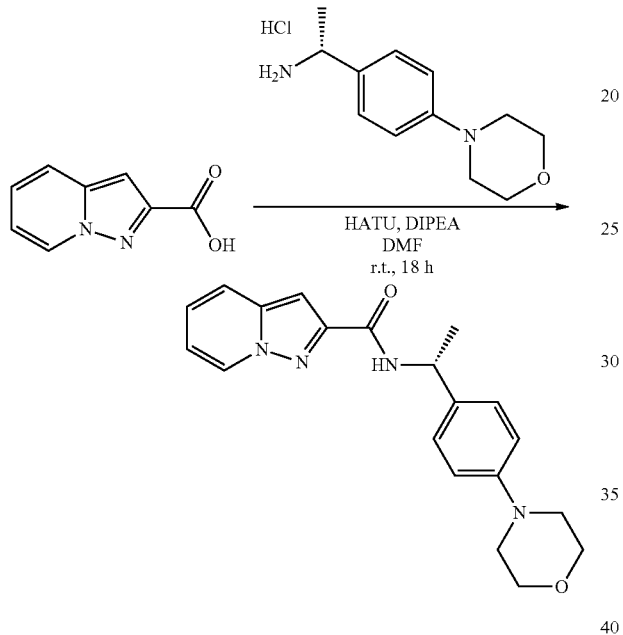

To a solution of pyrazolo[1,5-a]pyridine-2-carboxylic acid (100 mg, 0.617 mmol) in DMF (6.0 mL) were added HATU (305 mg, 0.80 mmol) and DIPEA (323 μL, 1.85 mmol). The reaction mixture was stirred at room temperature for 1 hour. After addition of (R)-1-(4-morpholinophenyl)ethanamine hydrochloride (intermediate 4, 165 mg, 0.80 mmol), the reaction mixture was stirred at room temperature for 18 hours. The reaction mixture was partitioned between water and EtOAc and the aqueous layer was extracted with EtOAc. The combined organic layers were washed with water and brine, dried over Na₂SO₄, filtered, and concentrated in vacuo. The residue was purified by column chromatography on NH—SiO₂ (Hexane:EtOAc=3:1 to 1:1) to afford the (R)—N-(1-(4-morpholinophenyl)ethyl)pyrazolo[1,5-a]pyridine-2-carboxamide (129 mg, 60%) as a white solid. ¹H-NMR (DMSO-d₆, Varian, 400 MHz): δ 1.47 (3H, d, J=7.2 Hz), 3.06 (4H, t, J=4.6 Hz), 3.72 (4H, t, J=4.4 Hz), 5.07-5.14 (1H, m), 6.89 (2H, d, J=8.8 Hz), 6.97 (1H, s), 7.02 (1H, t, J=6.8 Hz), 7.26-7.30 (3H, m), 7.76 (1H, d, J=8.8 Hz), 8.60 (1H, d, J=8.0 Hz), 8.68 (1H, d, J=7.2 Hz).

Example 29

This example is directed to a synthesis of (R)—N-(1-(4-(piperazin-1-yl)phenyl)ethyl)pyrazolo[1,5-a]pyridine-2-carboxamide.

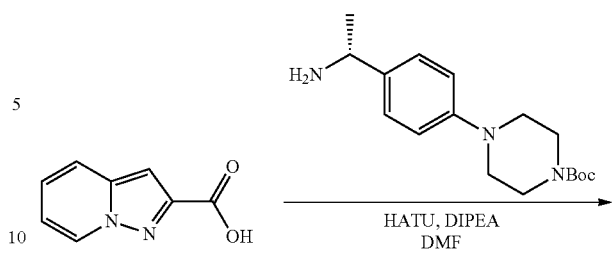

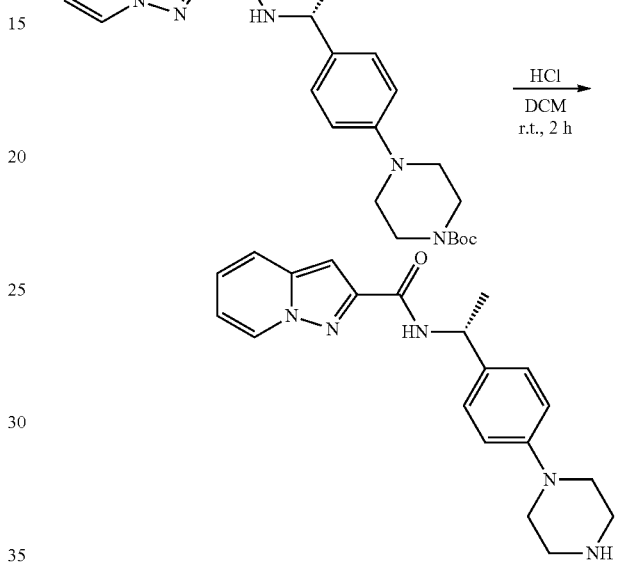

Step A: (R)-tert-butyl 4-(4-(1-(pyrazolo[1,5-a]pyridine-2-carboxamido)ethyl)phenyl)piperazine-1-carboxylate

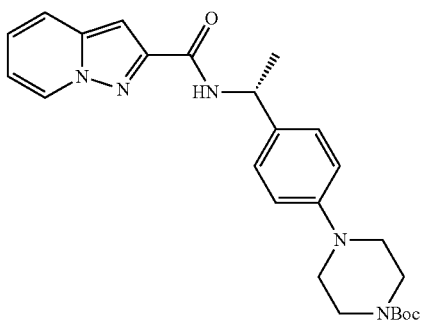 [SMILES: C[C@@H](NC(=O)c1cc2ccccn2n1)c1ccc(N2CCN(C(=O)OC(C)(C)C)CC2)cc1]

To a solution of pyrazolo[1,5-a]pyridine-2-carboxylic acid (173 mg, 1.07 mmol) in DMF (9.0 mL) were added HATU (610 mg, 1.60 mmol) and DIPEA (544 μL, 3.12 mmol). The reaction mixture was stirred at room temperature for 1 hour. After addition of (R)-tert-butyl 4-(4-(1-aminoethyl)phenyl)piperazine-1-carboxylate (intermediate 6, 270 mg, 0.981 mmol), the reaction mixture was stirred at room temperature for 18 hours. The reaction mixture was partitioned between water and EtOAc and the aqueous layer was extracted with EtOAc. The combined organic layers were washed with water and brine, dried over Na₂SO₄, filtered, and concentrated in vacuo. The residue was purified by column chromatography on SiO₂ (EtOAc:Hexane=1:1 to 3:1) to afford the (R)-tert-butyl 4-(4-(1-(pyrazolo[1,5-a]pyridine-2-carboxamido)ethyl)phenyl)piperazine-1-carboxylate (317 mg, 79%) as a white solid. ¹H-NMR (DMSO-d₆, Varian, 400 MHz): δ 1.41 (9H, s), 1.47 (3H, d, J=6.8 Hz), 3.04 (4H, t, J=5.2 Hz), 3.43-3.45 (4H, m), 5.08-5.15 (1H, m), 6.91 (2H, d, J=8.4 Hz), 6.98 (1H, s), 7.03 (1H, t, J=6.3 Hz), 7.26-7.30 (3H, m), 7.76 (1H, d, J=8.8 Hz), 8.64 (1H, d, J=8.8 Hz), 8.68 (1H, d, J=7.2 Hz).

Step B: (R)—N-(1-(4-(piperazin-1-yl)phenyl)ethyl)pyrazolo[1,5-a]pyridine-2-carboxamide

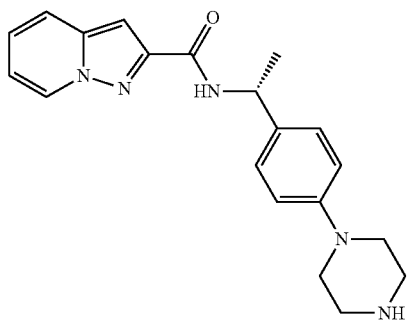 [SMILES: C[C@@H](NC(=O)c1cc2ccccn2n1)c1ccc(N2CCNCC2)cc1]

To a solution of (R)-tert-butyl 4-(4-(1-(pyrazolo[1,5-a]pyridine-2-carboxamido)ethyl)phenyl)piperazine-1-carboxylate (371 mg, 0.83 mmol) in DCM (8.3 mL) was added HCl (4 M in dioxane, 2.06 mL, 8.25 mmol). After stirred at room temperature for 2 hours, the reaction mixture was concentrated in vacuo. The residue was diluted with DCM and basified with 2 N NaOH, washed with water and brine. The separated organic layer was dried over Na₂SO₄, filtered, and concentrated in vacuo. The residue was purified by column chromatography on SiO₂ (EtOAc to EtOAc: MeOH=20:1) to afford the (R)—N-(1-(4-(piperazin-1-yl)phenyl)ethyl)pyrazolo[1,5-a]pyridine-2-carboxamide (126 mg, 44%) as a white solid. ¹H-NMR (DMSO-d₆, Varian, 400 MHz): δ 1.46 (3H, d, J=6.8 Hz), 2.33 (1H, s), 2.80 (4H, t, J=4.8 Hz), 2.98 (4H, t, J=4.6 Hz), 5.08-5.12 (1H, m), 6.86 (2H, d, J=8.4 Hz), 6.97 (1H, s), 7.03 (1H, t, J=6.8 Hz), 7.25-7.30 (3H, m), 7.76 (1H, d, J=9.2 Hz), 8.63 (1H, d, J=8.4 Hz), 8.69 (1H, d, J=7.2 Hz).

Example 30

This example is directed to a synthesis of (R)—N-(1-(4-(morpholine-4-carbonyl)phenyl)ethyl)pyrazolo[1,5-a]pyridine-2-carboxamide.

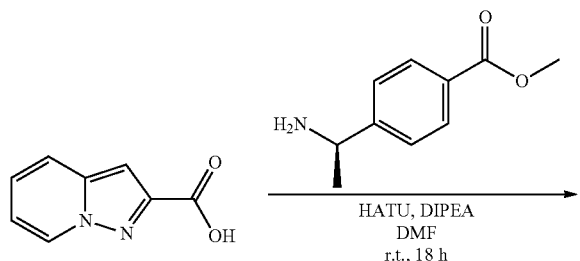

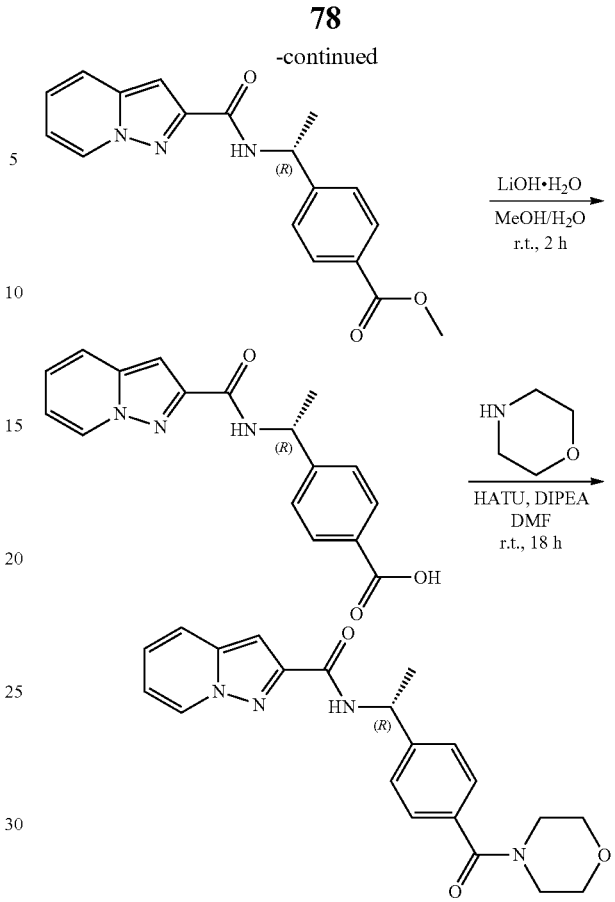

Step A: (R)-methyl 4-(1-(pyrazolo[1,5-a]pyridine-2-carboxamido)ethyl)benzoate

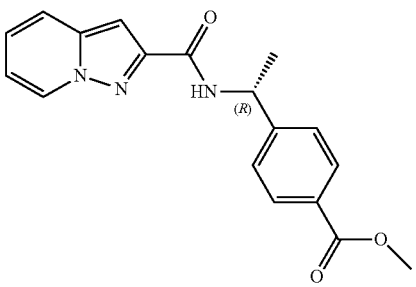

To a solution of pyrazolo[1,5-a]pyridine-2-carboxylic acid (100 mg, 0.62 mmol) in DMF (6.0 mL) were added HATU (305 mg, 0.80 mmol) and DIPEA (215 μL, 1.23 mmol). The reaction mixture was stirred at room temperature for 1 hour. After addition of (R)-methyl 4-(1-aminoethyl)benzoate (133 mg, 0.740 mmol), the reaction mixture was stirred at room temperature for 18 hours. The reaction mixture was partitioned between water and EtOAc and the aqueous layer was extracted with EtOAc. The combined organic layers were washed with water and brine, dried over Na₂SO₄, filtered, and concentrated in vacuo. The residue was purified by column chromatography on SiO₂ (EtOAc: Hexane=1:1 to 2:1) to afford the (R)-methyl 4-(1-(pyrazolo[1,5-a]pyridine-2-carboxamido)ethyl)benzoate (160 mg, 80%) as a yellow solid. ¹H-NMR (CDCl₃, Varian, 400

MHz): δ 1.64 (3H, d, J=7.2 Hz), 3.91 (3H, s), 5.37-5.44 (1H, m), 6.87 (1H, t, J=6.8 Hz), 7.06 (1H, s), 7.15 (1H, t, J=7.8 Hz), 7.39 (1H, d, J=7.6 Hz), 7.49 (2H, d, J=8.4 Hz), 7.59 (1H, d, J=8.8 Hz), 8.02 (2H, d, J=8.4 Hz), 8.38 (1H, d, J=7.2 Hz).

Step B: (R)-4-(1-(pyrazolo[1,5-a]pyridine-2-carboxamido)ethyl)benzoic acid

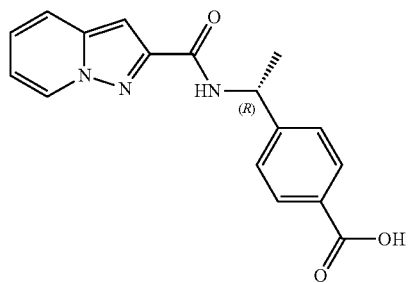

To a solution of (R)-methyl 4-(1-(pyrazolo[1,5-a]pyridine-2-carboxamido)ethyl)benzoate (160 mg, 0.50 mmol) in MeOH (3.0 mL) and water (1.0 mL) was added LiOH.H$_2$O (119 mg, 4.95 mmol) at room temperature. The reaction mixture was stirred for 1 hour at room temperature and concentrated in vacuo. The residue was diluted with DCM and acidified with 2 N HCl, washed with water and brine. The separated organic layer was dried over Na$_2$SO$_4$, filtered, and concentrated in vacuo to afford the (R)-4-(1-(pyrazolo[1,5-a]pyridine-2-carboxamido)ethyl)benzoic acid (131 mg, 86%) as a white solid which was used for the next step without further purification. $^1$H-NMR (DMSO-d$_6$, Varian, 400 MHz): δ 1.52 (3H, d, J=7.2 Hz), 5.22-5.25 (1H, m), 6.90 (1H, s), 7.04 (1H, t, J=7.0 Hz), 7.29 (1H, t, J=7.8 Hz), 7.54 (2H, d, J=8.4 Hz), 7.77 (1H, d, J=8.8 Hz), 7.90 (2H, d, J=8.0 Hz), 8.70 (1H, d, J=6.8 Hz), 9.95 (1H, d, J=8.4 Hz), 12.8 (1H, s).

Step C: (R)—N-(1-(4-(morpholine-4-carbonyl)phenyl)ethyl)pyrazolo[1,5-a]pyridine-2-carboxamide

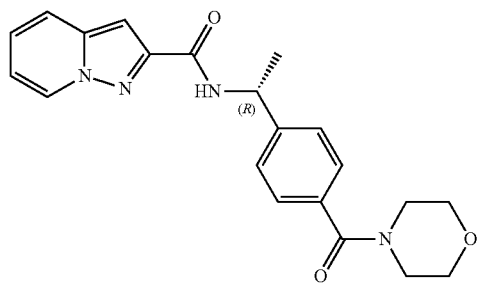

To a solution of (R)-4-(1-(pyrazolo[1,5-a]pyridine-2-carboxamido)ethyl)benzoic acid (131 mg, 0.42 mmol) in DMF (4.0 mL) were added HATU (209 mg, 0.55 mmol) and DIPEA (148 μL, 0.85 mmol). The reaction mixture was stirred at room temperature for 1 hour. After addition of morphorine (37 μL, 0.42 mmol), the reaction mixture was stirred at room temperature for 18 hours. The reaction mixture was partitioned between water and EtOAc and the aqueous layer was extracted with EtOAc. The combined organic layers were washed with water and brine, dried over Na$_2$SO$_4$, filtered, and concentrated in vacuo. The residue was purified by column chromatography on SiO$_2$ (EtOAc: Hexane=1:1 to 2:1) to afford the (R)—N-(1-(4-(morpholine-4-carbonyl)phenyl)ethyl)pyrazolo[1,5-a]pyridine-2-carboxamide (130 mg, 81%) as a white solid. $^1$H-NMR (DMSO-d$_6$, Varian, 400 MHz): δ 1.52 (3H, d, J=7.2 Hz), 3.36-3.41 (2H, m), 6.59-3.61 (6H, m), 5.18-5.25 (1H, m), 6.99 (1H, s), 7.04 (1H, t, J=7.0 Hz), 7.29 (1H, t, J=8.0 Hz), 7.37 (2H, d, J=8.0 Hz), 7.49 (2H, d, J=8.4 Hz), 7.78 (1H, d, J=8.4 Hz), 8.70 (1H, d, J=6.8 Hz), 8.94 (1H, d, J=8.8 Hz).

Example 31

This example is directed to a synthesis of (R)—N-(1-(4-(1H-pyrrol-1-yl)phenyl)ethyl)pyrazolo[1,5-a]pyridine-2-carboxamide.

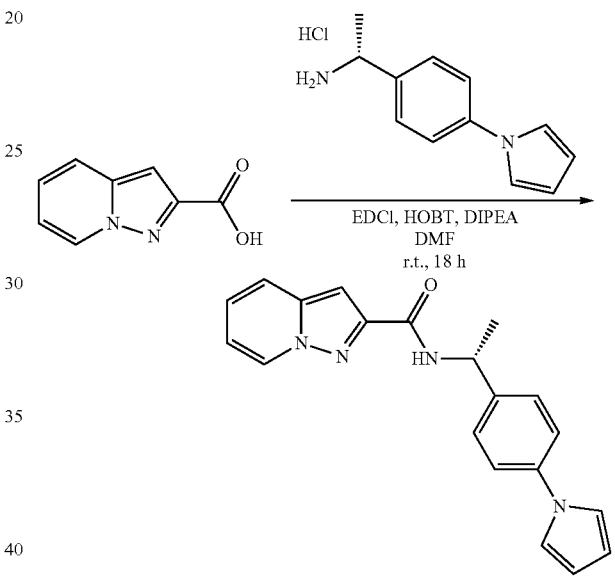

To a mixture of pyrazolo[1,5-a]pyridine-2-carboxylic acid (58.0 mg, 0.36 mmol), hydroxybenzotriazole (HOBt) (96.0 mg, 0.71 mmol), DIPEA (217 μL, 1.24 mmol), EDCI (1-ethyl-3-(3-dimethylaminopropyl)carbodiimide) (132 mg, 0.85 mmol) in DMF (5 mL) was added (R)-1-(4-(1H-pyrrol-1-yl)phenyl)ethanamine hydrochloride (intermediate 12, 95.0 mg, 0.427 mmol) and then the reaction mixture was stirred at room temperature for 18 hours. The reaction mixture was dissolved with EtOAc and washed with water and brine. The separated organic layer was dried over Na$_2$SO$_4$, filtered off and concentrated in vacuo. The residue was purified by column chromatography on SiO$_2$ (Hexane: EtOAc=5:1) to afford the (R)—N-(1-(4-(1H-pyrrol-1-yl)phenyl)ethyl)pyrazolo[1,5-a]pyridine-2-carboxamide (57.0 mg, 48%) as a white solid. $^1$H-NMR (400 MHz, CDCl$_3$): δ 1.66 (3H, d, J=6.8 Hz), 5.37-5.41 (1H, m), 6.34 (2H, s), 6.86 (1H, t, J=6.8 Hz), 7.07 (2H, s), 7.15 (1H, t, J=8.0 Hz), 7.36-7.38 (3H, m), 7.48 (2H, d, J=8.0 Hz), 7.59 (1H, d, J=9.2 Hz), 8.38 (1H, d, J=8.4 Hz). *1 H form NH was not observed Example 32

This example is directed to a synthesis of N—((R)-1-(4-(2-methylmorpholino)phenyl)ethyl)pyrazolo[1,5-a]pyridine-2-carboxamide.

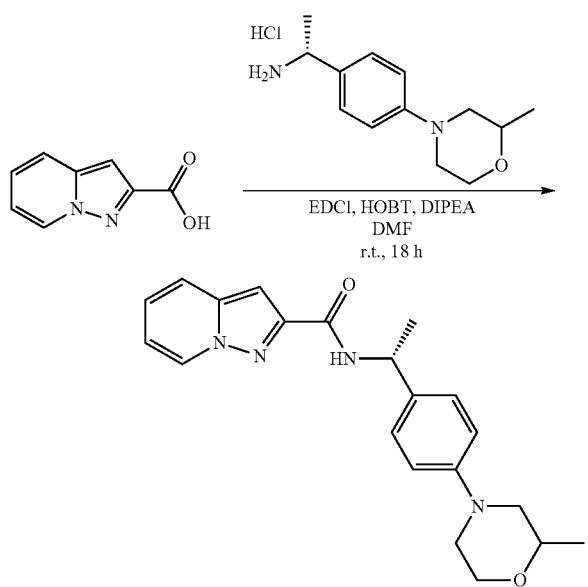

To a mixture of pyrazolo[1,5-a]pyridine-2-carboxylic acid (67.0 mg, 0.41 mmol), HOBt (111 mg, 0.824 mmol), DIPEA (251 μL, 1.443 mmol), EDCI (154 mg, 0.99 mmol) in DMF (5 mL) was added (R)-1-(4-(2-methylmorpholino)phenyl) ethanamine hydrochloride (intermediate 13, 127 mg, 0.495 mmol) and then stirred at room temperature for 18 hours. The reaction mixture was dissolved with EtOAc and washed with aq 0.5 M citric acid solution, aq NaHCO$_3$ solution, and brine. The organic layer was dried over Na$_2$SO$_4$, filtered off, and concentrated in vacuo. The residue was purified by column chromatography on SiO$_2$ (MeOH:DCM=40:1) to afford the N—((R)-1-(4-(2-methylmorpholino)phenyl) ethyl)pyrazolo[1,5-a]pyridine-2-carboxamide (94.0 mg, 62%) as a white solid. $^1$H-NMR (400 MHz, CDCl$_3$): δ 1.24 (3H, d, J=6.0 Hz), 1.62 (3H, d, J=6.8 Hz), 2.47 (1H, t, J=11.2 Hz), 2.81 (1H, td, J=11.8 Hz), 3.38-3.46 (2H, m), 3.73-3.82 (2H, m), 3.99-4.02 (1H, m), 5.30-5.33 (1H, m), 6.84 (1H, t, J=7.0 Hz), 6.90 (2H, d, J=8.8 Hz), 7.06 (1H, s), 7.14 (1H, t, J=7.4 Hz), 2.26-7.35 (1H, m), 7.34 (2H, d, J=8.4 Hz), 7.58 (1H, d, J=8.8 Hz), 8.35 (1H, d, J=6.8 Hz).

Example 33

This example is directed to a synthesis of (R)—N-(1-(4-(piperidin-1-yl)phenyl)ethyl)pyrazolo[1,5-a]pyridine-2-carboxamide.

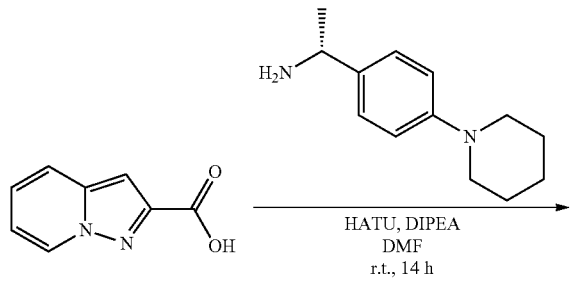

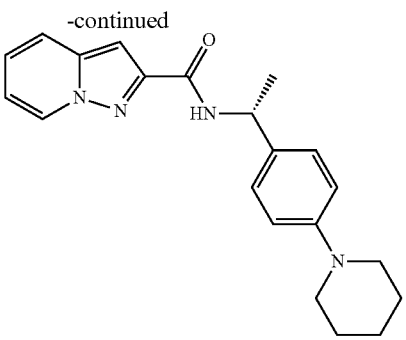

To a solution of pyrazolo[1,5-a]pyridine-2-carboxylic acid (80.0 mg, 0.49 mmol) in DMF (5 mL) were added HATU (281 mg, 0.740 mmol) and DIPEA (259 μL, 1.480 mmol) at room temperature. After 10 min, the (R)-1-(4-(piperidin-1-yl)phenyl)ethanamine hydrochloride (intermediate 14, 121 mg, 0.59 mmol) was added to the mixture and stirred for 14 hours at room temperature. The mixture was diluted with EtOAc and washed with water and brine. The separated organic layer was dried over Na$_2$SO$_4$, filtered, and concentrated in vacuo. The residue was purified by column chromatography on NH SiO$_2$ (EtOAc:Hexane=2:1) to afford the (R)—N-(1-(4-(piperidin-1-yl)phenyl)ethyl)pyrazolo[1,5-a]pyridine-2-carboxamide (50.0 mg, 29%) as a yellow solid. $^1$H-NMR (400 MHz, DMSO-d$_6$): δ 1.47 (3H, d, J=6.8 Hz), 1.49-1.53 (2H, m), 1.57-1.62 (4H, m), 3.08 (4H, t, J=5.2 Hz), 5.08-5.13 (1H, m), 6.87 (2H, d, J=8.4 Hz), 6.97 (1H, s), 7.02 (1H, dt, J=6.9 Hz), 7.25 (2H, d, J=8.4 Hz), 7.29 (1H, d, J=6.4 Hz), 7.76 (1H, d, J=9.2 Hz), 8.58 (1H, d, J=8.8 Hz), 8.68 (1H, d, J=6.8 Hz).

Example 34

This example is directed to a synthesis of (R)—N-(1-(4-morpholinophenyl)ethyl)pyrazolo[1,5-a]pyrimidine-2-carboxamide.

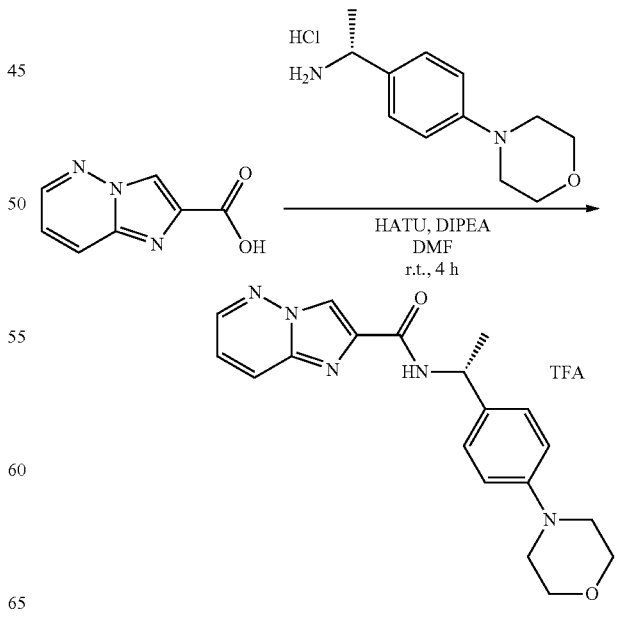

To a solution of pyrazolo[1,5-a]pyrimidine-2-carboxylic acid (100 mg, 0.61 mmol) in DMF (6.1 mL) was added HATU (350 mg, 0.92 mmol), DIPEA (321 μL, 1.84 mmol) and (R)-1-(4-morpholinophenyl)ethanamine hydrochloride (intermediate 2, 149 mg, 0.61 mmol) at room temperature. The reaction mixture was stirred at room temperature for 4 hours. After quenched by addition of water, the mixture was extracted with EtOAc. The separated organic layer was washed with brine, dried over Na$_2$SO$_4$, filtered, and concentrated in vacuo. The residue was purified by prep-HPLC to afford the (R)—N-(1-(4-morpholinophenyl)ethyl)pyrazolo[1,5-a]pyrimidine-2-carboxamide (150 mg, 54%) as a white solid. $^1$H-NMR (400 MHz, DMSOd$_6$): δ 1.48 (3H, d, J=7.2 Hz), 3.08 (4H, t, J=4.6 Hz), 3.73 (4H, t, J=4.6 Hz), 5.09-5.16 (1H, m), 6.92 (2H, d, J=8.8 Hz), 7.07 (1H, s), 7.18 (1H, dd, J=7.0 and 3.8 Hz), 7.29 (2H, d, J=8.4 Hz), 8.62-8.66 (1H, m), 8.74 (1H, d, J=8.0 Hz), 9.12 (1H, d, J=6.8 Hz).

Example 35

This example is directed to a synthesis of (R)—N-(1-(4-morpholinophenyl)ethyl)-1H-benzo[d]imidazole-2-carboxamide.

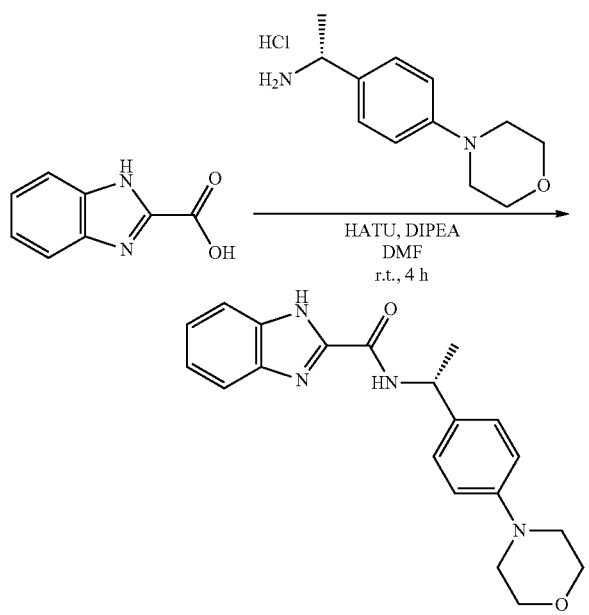

To a mixture of 1H-benzo[d]imidazole-2-carboxylic acid (100 mg, 0.62 mmol), HOBt (167 mg, 1.23 mmol), DIPEA (376 μL, 2.15 mmol), EDCI (230 mg, 1.48 mmol) in DMF (5 mL) was added (R)-1-(4-morpholinophenyl)ethanamine hydrochloride (intermediate 4, 180 mg, 0.74 mmol) and then stirred at room temperature for 4 hours. The reaction mixture was dissolved with EtOAc and washed with aq 0.5 M citric acid solution, aq NaHCO$_3$ solution and brine. The organic layer was dried over Na$_2$SO$_4$, filtered, and concentrated in vacuo. The residue was purified by column chromatography on SiO$_2$ (DCM:MeOH=1:20) to afford the (R)—N-(1-(4-morpholinophenyl)ethyl)-1H-benzo[d]imidazole-2-carboxamide (137 mg, 63%) as a white solid. $^1$H-NMR (400 MHz, DMSOd$_6$): δ 1.50 (3H, d, J=6.8 Hz), 3.06 (4H, t, J=4.8 Hz), 3.71-3.72 (4H, m), 5.20-5.30 (1H, m), 6.90 (2H, d, J=8.8 Hz), 7.29 (1H, brs), 7.50-7.70 (2H, m), 9.15 (1H, brs). *2H from NH was not observed.

Example 36

This example demonstrates an enzymatic assay for measuring IDO/TDO activity.

Figure 15:
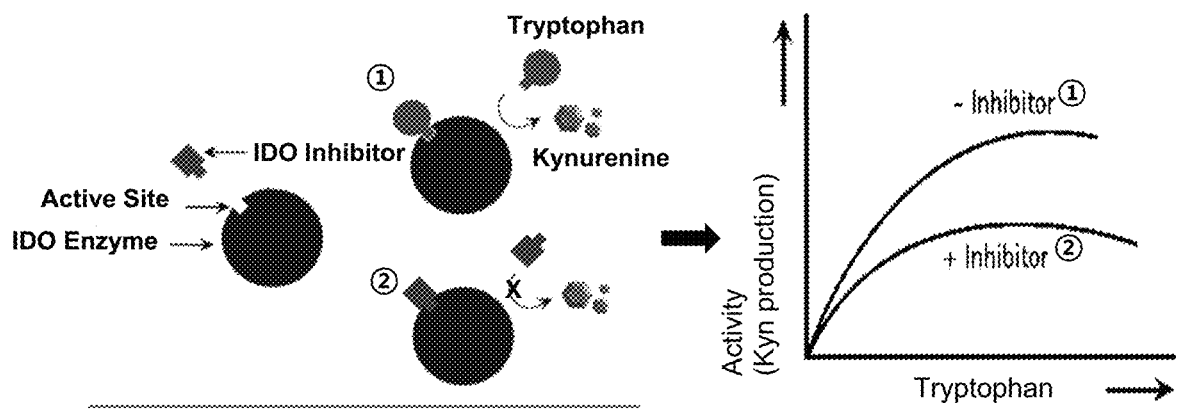
FIG. 15 is a schematic of an enzyme assay, in which IDO/TDO inhibitor compound or IDO/TDO enzyme was competitively reacted to L-tryptophan substrate.

The biological activity of indoleamine 2,3-dioxygenase (IDO) and tryptophan 2,3-dioxygenase (TDO) was measured by an IDO/TDO inhibitor screening assay kit (BPS Bioscience, San Diego, Calif.). IDO/TDO inhibitor or IDO/TDO enzyme was competitively reacted to L-tryptophan substrate. See FIG. 15. Each sample was prepared at a variety of concentration to analyze the enzyme kinetics. The enzyme reaction solution (180 μl) was placed in each well and added 10 μl of IDO/TDO inhibitor to the each well containing L-tryptophan substrate. Next, 40 ng/ml of His-tagged IDO or 50 ng/ml His-tagged TDO was added and incubated for 3 h at room temperature. The activity was measured by the absorbance at 320 nm on Multiskan FC Microplate Photometer (Thermo Scientific, Rockford, Ill., USA). The dissociation constant, Ki value, for enzyme-inhibitor complex for IDO/TDO inhibitor compound was determined on GraphPad software 'Enzyme Kinetics panel of equations' (Table 1).

TABLE 1

| IDO/TDO inhibitor | IDO Enzyme Ki (μM) | TDO Enzyme Ki (μM) |
|---|---|---|
| CB-510 | 100 | 32.2 |
| CB-511 | 18.9 | 2.5 |
| CB-512 | 3.5 | 6.7 |
| CB-516 | N.D. | 0.5 |
| CB-517 | 5.4 | 0.3 |
| CB-518 | 3.1 | 0.1 |
| CB-532 | 1.9 | 35 |
| CB-533 | 1.2 | 68.6 |
| CB-534 | 1.4 | 8.1 |
| CB-539 | 3.4 | 4.0 |
| CB-540 | 3.0 | N.D. |
| CB-548 | 2.6 | 17.1 |
| CB-549 | 1.6 | 2.7 |
| CB-550 | 3.8 | 1.8 |
| CB-556 | 5.2 | 17.9. |

N.D.: Not Detected

The human colorectal adenocarcinoma HT-29, human brain glioblastoma A172, murine colon carcinoma CT26, and murine mammary carcinoma 4T1 cell lines were obtained from American Type Culture Collection (Manassas, Va., USA). The cells were cultured in RPMI-1640 medium (Thermo Scientific, Waltham, Mass., USA) supplemented with 10% fetal bovine serum and 1% penicillin and streptomycin solution. The cells were maintained in a humidified atmosphere of 5% CO$_2$ and 95% air at 37° C.

A variety of human and murine cells (1×10$^5$) were plated in 12-well cultured plates and incubated for 48 h. IDO/TDO inhibitors dissolved in dimethylsulfoxide (DMSO) were serially treated at concentrations of 0, 0.4, 2, 10, 50, 250 nM. After 24 h, the supernatant of the treated cells was collected and measured by Kynurenine ELISA kit (Antibodies-online Inc., Atlanta, Ga., USA). All standards or the culture supernatant (100 μl) were placed in the antibody pre-coated microtiter plate, and 50 μl of conjugate was added to each well. The mixed samples were incubated for 1 h at 37° C. and washed several times. To the washed plates, 100 μl of substrate containing 3,3',5,5'-tetramethylbenzidine (TMB) and incubated in the dark for 15 min at 37° C. After mixing with 50 μl of stop solution, the products of the reaction were measured at 450 nm on MULTISKAN™ FC microplate photometer (Thermo Scientific, Waltham, Mass., USA).

Figure 16:
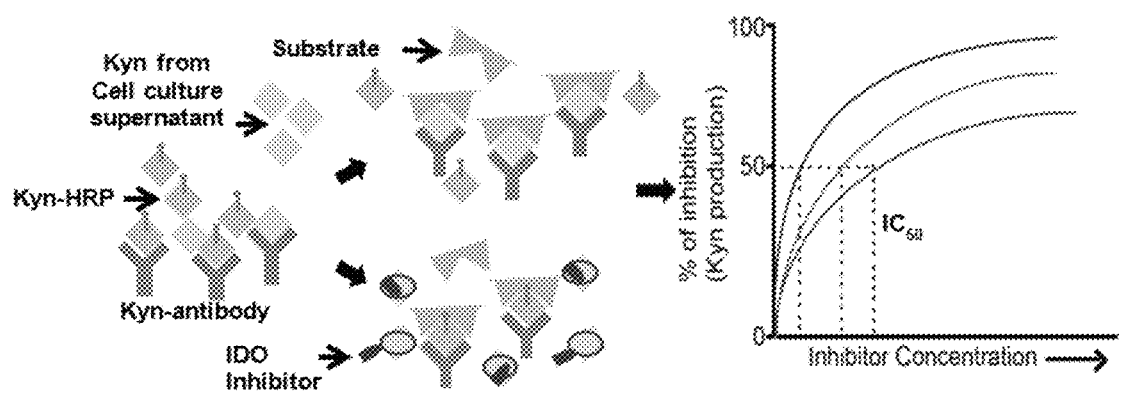
FIG. 16 is a schematic of a cell assay for the inhibition of kynurenine by an IDO/TDO inhibitor compound.

Based on the optimal density value of reference standard, the percentage of kynurenine inhibition was calculated and the IDO/TDO inhibitor $IC_{50}$ value was determined on GraphPad software 'Dose-Response-inhibition' (Table 2). See FIG. 16.

TABLE 2

| IDO/TDO inhibitor | HT-29 h-colon | A172 h-glioma | CT-26 m-colon | 4T1 m-breast |
|---|---|---|---|---|
| | | $IC_{50}$(nM) | | |
| CB-510 | 18.3 | 18.9 | 1.1 | 84.5 |
| CB-511 | 164.7 | N.D. | 47.3 | 31.3 |
| CB-512 | 2.2 | 30.5 | 52.2 | 8.9 |
| CB-516 | 112.8 | 48 | N.D. | N.D. |
| CB-517 | 43.7 | 61.9 | 13.53 | 20.9 |
| CB-518 | 9.5 | 106.4 | 15.1 | 44.7 |
| CB-532 | 91.2 | 12.6 | 15.6 | N.D. |
| CB-533 | 4.1 | 16.1 | 8.05 | 31.5 |
| CB-534 | 79.5 | N.D. | 30.3 | 22.4 |
| CB-539 | 23.6 | 90.3 | 21.5 | 47.2 |
| CB-540 | 45.01 | 6.4 | 11.6 | N.D. |
| CB-548 | 58.4 | 13.7 | 13.6 | 12.4 |
| CB-549 | N.D. | 47.4 | 29.2 | 82.1 |
| CB-550 | 105.6 | 10.8 | 18.8 | 29.6 |
| CB-556 | 211 | N.D. | 75.3 | N.D. |

N.D.: Not Detected

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula (Ia):

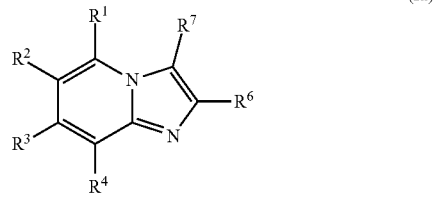

(Ia)

wherein
$R^1$, $R^2$, $R^3$, and $R^4$ are each independently H, alkyl, haloalkyl, halogen, or CN;
$R^6$ is

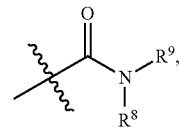

wherein
$R^8$ is selected from H and alkyl, and
$R^9$ is a group of the following formula:

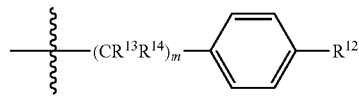

wherein
$R^{12}$ is $(CH_2)_oNR^{15'}R^{16'}$ or $(CH_2)_oC(=O)NR^{15'}R^{16'}$,
$R^{13}$ is H,
$R^{14}$ is alkyl,
m is 0 to 6,
o is 0 to 4,
$R^{15}$ and $R^{16}$ combine, along with the N to which they are bonded, to form morpholinyl or piperazinyl, each of which is optionally substituted with one or more substituents selected from alkyl, acetyl, and methylsulfonyl,
$R^{15'}$ and $R^{16'}$ are the same or different and are each H or alkyl, or combine, along with the N to which they are bonded, to form morpholinyl or piperazinyl, each of which is optionally substituted with one or more substituents selected from alkyl, acetyl, and methylsulfonyl, and
$R^7$ is H, $C_1$-$C_6$ alkyl, or cycloalkyl,
or a pharmaceutically acceptable salt thereof.

2. The compound of claim 1, wherein
$R^{12}$ is $(CH_2)_oNR^{15'}R^{16'}$,
$R^{15}$ and $R^{16}$ combine, along with the N to which they are bonded, to form morpholinyl or piperazinyl, each of which is optionally substituted with one or more substituents selected from alkyl, acetyl, and methylsulfonyl, and o is 0 or 1, or a pharmaceutically acceptable salt thereof.

3. The compound of claim 2, wherein $R^{13}$ is H and $R^{14}$ is methyl, or a pharmaceutically acceptable salt thereof.

4. The compound of claim 2, wherein m is 1, or a pharmaceutically acceptable salt thereof.

5. The compound of claim 2, wherein o is 0, or a pharmaceutically acceptable salt thereof.

6. The compound of claim 1, wherein $R^{12}$ is $(CH_2)_oC(=O)NR^{15'}R^{16'}$ and $R^{15'}$ and $R^{16'}$ are each alkyl.

7. The compound of claim 1, wherein one of $R^1$, $R^2$, $R^3$, and $R^4$ is alkyl, haloalkyl, halogen, or CN and the remaining three substituents are H, or a pharmaceutically acceptable salt thereof.

8. The compound of claim 1, wherein each of $R^1$, $R^2$, $R^3$, and $R^4$ is H, or a pharmaceutically acceptable salt thereof.

9. The compound of claim 1 that is selected from:

(CB539)

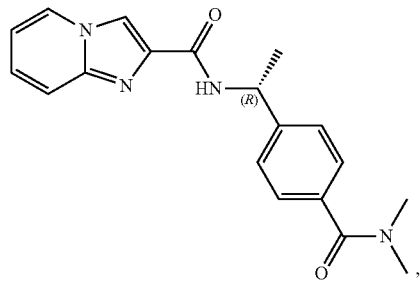

(CB540)

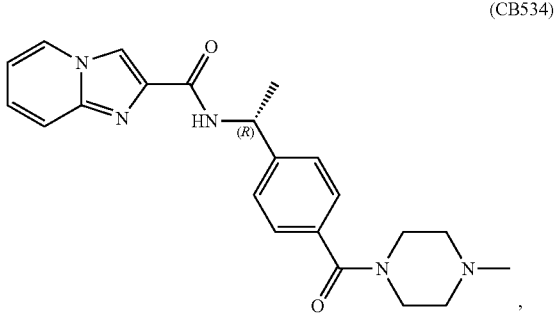

(CB533)

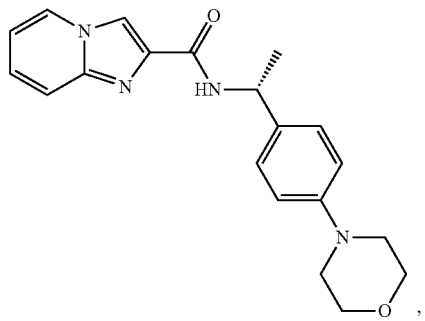

-continued (CB532)

(CB534)

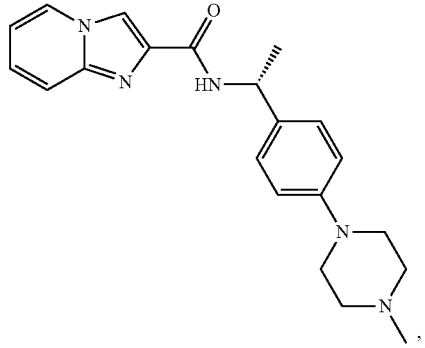

(CB548)

(CB549)

(CB550)

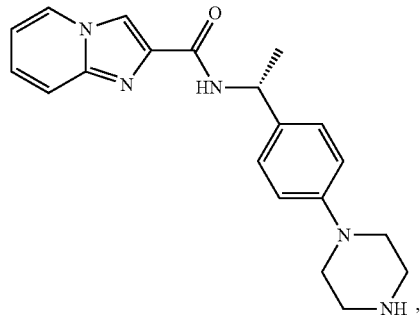

-continued
(CB581)
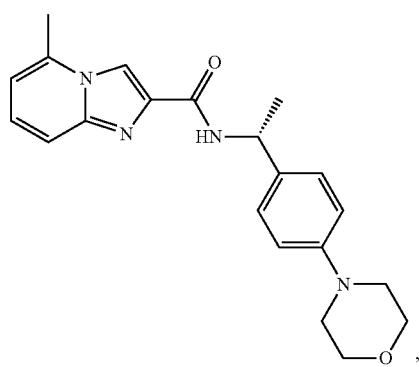
(CB585)
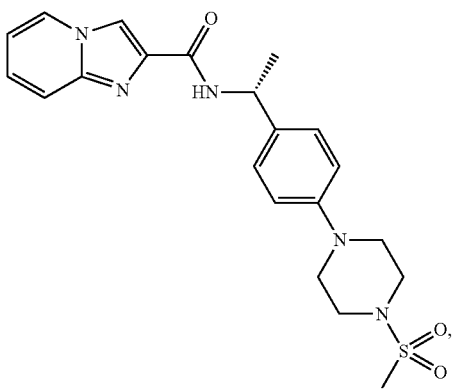
(CB582)
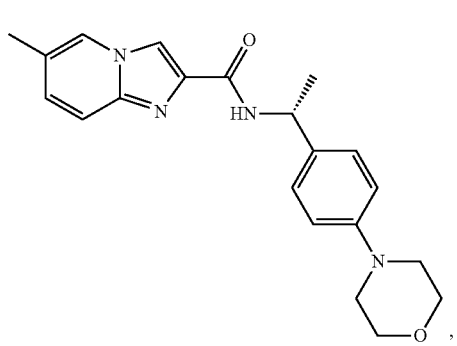
(CB586)
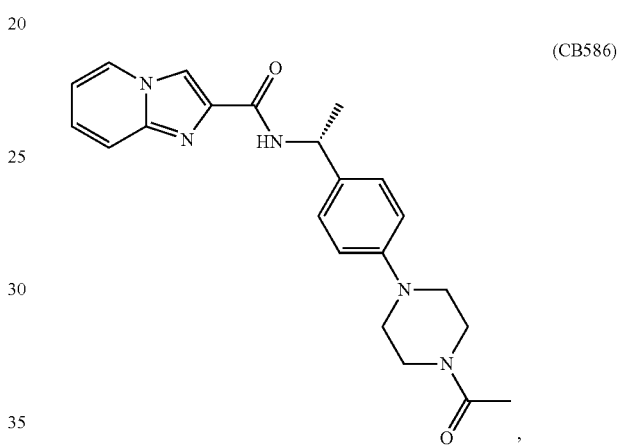
(CB583)
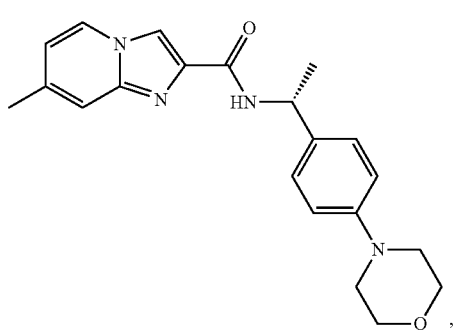
(CB590)
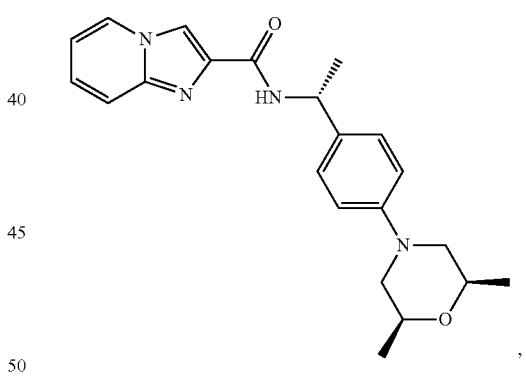
(CB584)
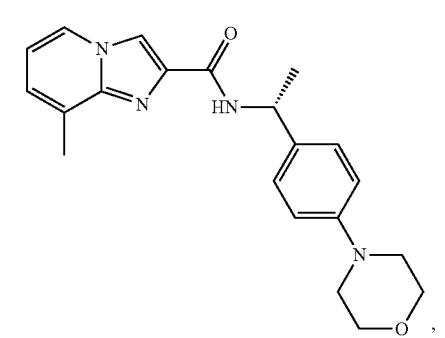
(CB595)
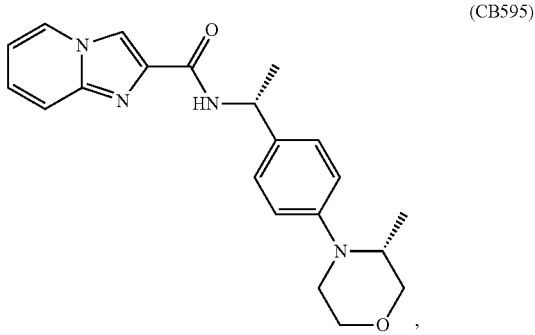

-continued

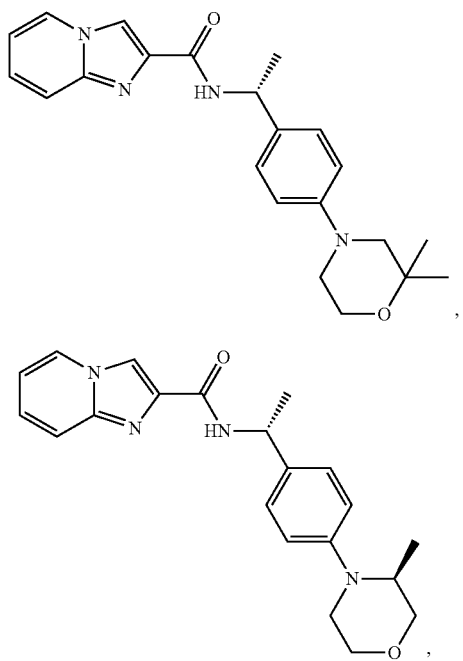

(CB596)

(CB597)

or a pharmaceutically acceptable salt thereof.

10. A pharmaceutical composition comprising at least one compound or pharmaceutically acceptable salt of claim 1 and a pharmaceutically acceptable carrier.

11. A method of inhibiting an indoleamine 2,3-dioxygenase (IDO) and/or tryptophan 2,3-dioxygenase (TDO) enzyme in a cell, the method comprising:
contacting an effective amount of the compound of claim 1 or a pharmaceutically acceptable salt thereof to a cell in need of such inhibition.

12. A method of treating an IDO- and/or TDO-mediated disease in a subject, wherein the disease is selected from the group consisting of colon cancer, breast cancer, and brain cancer the method comprising:
administering a pharmaceutically effective amount of the compound of claim 1 or a pharmaceutically acceptable salt thereof to a subject in need of such treatment.

13. The compound of claim 1, wherein
$R^{12}$ is $(CH_2)_oC(=O)NR^{15'}R^{16'}$,
$R^{15'}$ and $R^{16'}$ combine, along with the N to which they are bonded, to form morpholinyl or piperazinyl, each of which is optionally substituted with one or more substituents selected from alkyl, acetyl, and methylsulfonyl, and
o is 0 or 1,
or a pharmaceutically acceptable salt thereof.

14. The compound of claim 13, wherein
$R^{13}$ is H and $R^{14}$ is methyl,
or a pharmaceutically acceptable salt thereof.

15. The compound of claim 13, wherein m is 1, or a pharmaceutically acceptable salt thereof.

16. The compound of claim 13, wherein o is 0, or a pharmaceutically acceptable salt thereof.

17. The compound of claim 8, wherein $R^7$ is H, or a pharmaceutically acceptable salt thereof.

18. The compound of claim 17, wherein $R^8$ is H, or a pharmaceutically acceptable salt thereof.

19. The compound of claim 18, wherein
$R^{13}$ is H,
$R^{14}$ is methyl,
m is 1, and
o is 0 or 1,
or a pharmaceutically acceptable salt thereof.

* * * * *